United States Patent
Fletcher et al.

(10) Patent No.: US 10,464,861 B2
(45) Date of Patent: Nov. 5, 2019

(54) ASYMMETRIC ADDITION REACTIONS

(71) Applicant: Oxford University Innovation Limited, Oxford (GB)

(72) Inventors: Stephen P. Fletcher, Oxford (GB); Mireia Sidera Portela, Oxford (GB)

(73) Assignee: Oxford University Innovation Limited (GB)

( * ) Notice: Subject to any disclaimer, the term of this patent is extended or adjusted under 35 U.S.C. 154(b) by 4 days.

(21) Appl. No.: 15/580,838

(22) PCT Filed: Jun. 1, 2016

(86) PCT No.: PCT/GB2016/051612
§ 371 (c)(1),
(2) Date: Dec. 8, 2017

(87) PCT Pub. No.: WO2016/198836
PCT Pub. Date: Dec. 15, 2016

(65) Prior Publication Data
US 2018/0334414 A1     Nov. 22, 2018

(30) Foreign Application Priority Data

Jun. 9, 2015 (GB) .................................. 1510033.2

(51) Int. Cl.
| | |
|---|---|
| *C07D 213/86* | (2006.01) |
| *C07C 1/32* | (2006.01) |
| *C07B 37/04* | (2006.01) |
| *C07B 53/00* | (2006.01) |
| *C07C 201/12* | (2006.01) |
| *C07D 211/70* | (2006.01) |
| *C07C 67/343* | (2006.01) |
| *C07C 41/30* | (2006.01) |
| *C07D 309/18* | (2006.01) |
| *C07D 309/20* | (2006.01) |
| *C07D 309/22* | (2006.01) |
| *C07D 333/08* | (2006.01) |
| *C07D 231/56* | (2006.01) |
| *C07D 209/08* | (2006.01) |
| *C07F 5/02* | (2006.01) |
| *C07F 7/18* | (2006.01) |
| *C07D 213/61* | (2006.01) |
| *C07C 17/263* | (2006.01) |
| *C07D 307/79* | (2006.01) |

(52) U.S. Cl.
CPC .............. *C07C 1/321* (2013.01); *C07B 37/04* (2013.01); *C07B 53/00* (2013.01); *C07C 17/263* (2013.01); *C07C 41/30* (2013.01); *C07C 67/343* (2013.01); *C07C 201/12* (2013.01); *C07D 209/08* (2013.01); *C07D 211/70* (2013.01); *C07D 213/61* (2013.01); *C07D 231/56* (2013.01); *C07D 307/79* (2013.01); *C07D 309/18* (2013.01); *C07D 309/20* (2013.01); *C07D 309/22* (2013.01); *C07D 333/08* (2013.01); *C07F 5/025* (2013.01); *C07F 7/1804* (2013.01); *C07F 7/1892* (2013.01); *C07B 2200/07* (2013.01); *C07C 2531/22* (2013.01); *C07C 2531/24* (2013.01); *C07C 2601/10* (2017.05); *C07C 2601/16* (2017.05); *C07C 2601/18* (2017.05)

(58) Field of Classification Search
CPC ....... C07B 37/04; C07B 53/00; C07C 17/263; C07C 41/306; C07C 67/343; C07C 201/12; C07D 209/08; C07D 211/70; C07D 213/61; C07D 231/56; C07D 307/79; C07D 309/18; C07D 309/20; C07D 309/22; C07D 333/08; C07F 5/025; C07F 7/1804; C07F 7/1892
USPC ........................................................ 546/325
See application file for complete search history.

(56) References Cited

FOREIGN PATENT DOCUMENTS

WO    WO-2016/198836 A1    12/2016

OTHER PUBLICATIONS

Lee et al , Highly Site- and Enantioselective Cu-Catalyzed Allylic Alkylation Reactions with Easily Accessible Vinylaluminum Reagents,J. Am. Chem. Soc. 2008, 130, p. 446-447 (Year: 2008).*
Chung et al., "Nickel (0)-catalyzed asymmetric cross-coupling reactions of allylic compounds with arylboronic acids," J Chem Soc, Perk T 1, 1(16):2725-2729 (2000).
Hayashi, "Rhodium-catalyzed asymmetric addition of organo-boron and-titanium reagents to electron-deficient olefins," B Chem Soc Jpn, 77(1):13-21 (2004).
International Search Report and Written Opinion for International Application No. PCT/GB2016/051612 dated Aug. 23, 2016.
Kiuchi et al., "Rhodium-catalyzed asymmetric coupling reaction of allylic ethers with arylboronic acids," Org Lett, 4(17):4502-4505 (2012).
Langlois et al., "Copper☐Catalyzed Asymmetric Allylic Alkylation of Racemic Cyclic Substrates: Application of Dynamic Kinetic Asymmetric Transformation (DYKAT)," Adv Synth Catal, 352(Issue 2-3):447-457 (2010).
Menard et al., "Rhodium-catalyzed asymmetric allylic substitution with boronic acid nucleophiles," Org Lett, 8(20):4569-4572 (2006).
Polet et al., "Enantioselective Iridiu☐Catalyzed Allylic Arylation," Chemistry, 15(5):1205-1216 (2009).
Search Report issued by Intellectual Property Office in corresponding Application No. GB1510033.2, dated Mar. 9, 2016.

* cited by examiner

*Primary Examiner* — Taylor V Oh
(74) *Attorney, Agent, or Firm* — Foley Hoag LLP

(57) ABSTRACT

Processes of forming $C_{sp2}$—$C_{sp3}$ bonds at the allylic carbon of a cyclic allylic compound starting material are disclosed, in which a racemic mixture of a cyclic allylic compound having a leaving group attached to the allylic carbon is reacted with a compound having a nucleophilic carbon atom in the presence of a Rh(I), Pd(II) or Cu(I) pre-catalyst and a chiral ligand. The reaction products containing the newly-formed $C_{sp2}$—$C_{sp3}$ bond are generated in high stereoisomeric excess, and may therefore serve as important organic building blocks in the preparation of new agrochemicals and pharmaceuticals.

20 Claims, No Drawings

ASYMMETRIC ADDITION REACTIONS

RELATED APPLICATIONS

This application is a § 371 national-stage application based on Patent Cooperation Treaty Application serial number PCT/GB2016/051612, filed Jun. 1, 2016, which claims the benefit of priority to GB 1510033.2, filed Jun. 9, 2015.

INTRODUCTION

The present invention relates to asymmetric addition reactions. More particularly, the present invention relates to a process for the preparation of compounds in a stereoisomeric excess, the process involving the use of a catalyst.

BACKGROUND OF THE INVENTION

Catalytic asymmetric methods for organic synthesis provide access to single enantiomers of three-dimensional chiral molecules that serve as the basis of new medicines, materials and catalysts. $C_{sp2}$—$C_{sp2}$ cross-coupling reactions between arylboronic acid and aryl halides are widely used in both academia and industry and are strategically important in the development of new agrochemicals and pharmaceuticals.

One of the most widely used approaches to carbon-carbon bond formation in the fine chemical, pharmaceutical, and agrochemical industries, as well as in the synthesis of organic materials, is $sp^2$-$sp^2$ cross-coupling[1]. In particular the Suzuki-Miyaura reaction (see Scheme 1) is robust, convenient and widely used in the synthesis of lead compounds for the development of new medicines as it is well-suited to producing libraries of compounds[2-4].

Scheme 1

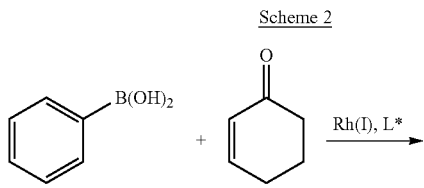

The development of robust and widely applicable methods that form single enantiomer chiral products is a major contemporary research goal[5]. Hayashi developed rhodium-catalyzed asymmetric conjugate addition reactions of boronic acid nucleophiles to prochiral α,β-unsaturated ketones with excellent yield and enantioselectivity[6,7] (see Scheme 2) and many related protocols have since been developed[8].

Scheme 2

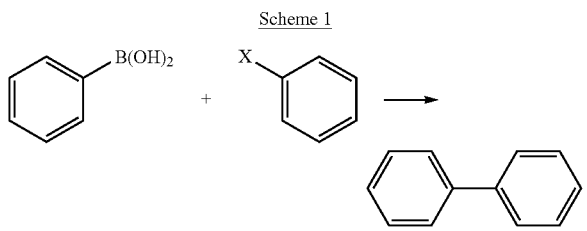

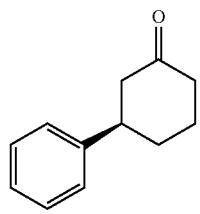

Evans reported that alkylations with stabilized nucleophiles[9,10] and arylations with non-stabilized aryl zinc nucleophiles[11] are highly stereospecific processes; overall retention of configuration is observed using stabilized nucleophiles and overall inversion occurs with arylzinc compounds, so that highly enantiomerically enriched compounds can be obtained by starting from single enantiomer allylic coupling partners (see Scheme 3).

Scheme 3

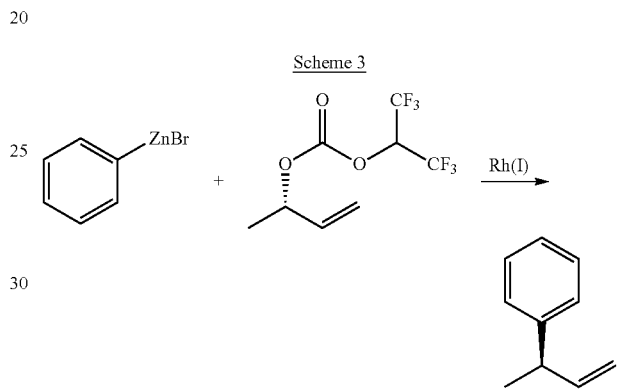

A particularly powerful class of asymmetric allylic alkylation (AAA) reactions allow the conversion of racemic starting materials into single enantiomer products[12,13] rather than starting from single enantiomer or prochiral starting materials. Pd-catalyzed processes that convert a racemic mixture of starting materials into a new single enantiomer product are commonly referred to as dynamic kinetic asymmetric transformations (DYKATs) as originally developed by Trost (see Scheme 4). DYKATs can now be used with a wide variety of stabilized nucleophiles and an array of metal catalysts[14] and several non-stabilized $sp^3$-hybridized nucleophiles can now be used in certain related procedures[15-18].

Scheme 4

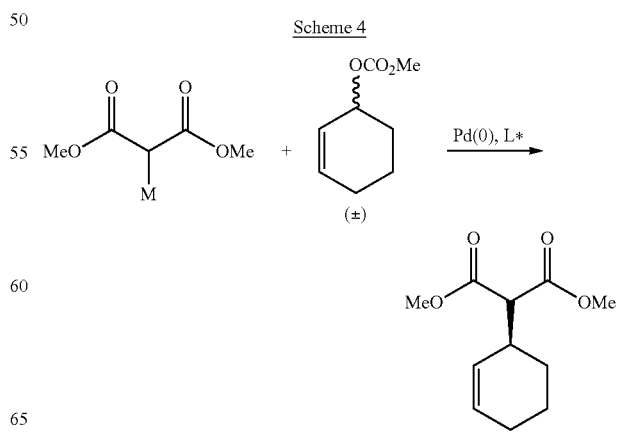

In spite of the advancements discussed above, there remains a need for alternative or more effective means of realising asymmetric allylic addition reactions.

The present invention was devised with the foregoing in mind.

SUMMARY OF THE INVENTION

According to a first aspect of the present invention there is provided a process for the formation of a $C_{sp3}$—$C_{sp2}$ bond at the allylic carbon of a cyclic allylic compound, the process comprising the step of:
   a) reacting a racemic mixture of a cyclic allylic compound having a leaving group attached to the allylic carbon with a compound having a nucleophilic carbon atom, wherein step a) is conducted in the presence of:
      i) a pre-catalyst based on Rh(I), Pd(II) or Cu(I); and
      ii) a chiral ligand
and wherein the formation of the $C_{sp3}$—$C_{sp2}$ bond results in the generation of a product compound in a stereoisomeric excess.

According to a second aspect of the present invention, there is provided a product compound in a stereoisomeric excess obtainable, obtained or directly obtained by a process defined herein.

DETAILED DESCRIPTION OF THE INVENTION

Definitions

Unless otherwise stated, the following terms used in the specification and claims have the following meanings set out below.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo [2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkyl" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from: a benzene ring fused to a 5- or 6-membered ring containing 1, 2 or 3 ring heteroatoms; a pyridine ring fused to a 5- or 6-membered ring containing 1, 2 or 3 ring heteroatoms; a pyrimidine ring fused to a 5- or 6-membered ring containing 1 or 2 ring heteroatoms; a pyrrole ring fused to a 5- or 6-membered ring containing 1, 2 or 3 ring heteroatoms; a pyrazole ring fused to a 5- or 6-membered ring containing 1 or 2 ring heteroatoms; a pyrazine ring fused to a 5- or 6-membered ring containing 1 or 2 ring heteroatoms; an imidazole ring fused to a 5- or 6-membered ring containing 1 or 2 ring heteroatoms; an oxazole ring fused to a 5- or 6-membered ring containing 1 or 2 ring heteroatoms; an isoxazole ring fused to a 5- or 6-membered ring containing 1 or 2 ring heteroatoms; a thiazole ring fused to a 5- or 6-membered ring containing 1 or 2 ring heteroatoms; an isothiazole ring fused to a 5- or 6-membered ring containing 1 or 2 ring heteroatoms; a thiophene ring fused to a 5- or 6-membered ring containing 1, 2 or 3 ring heteroatoms; a furan ring fused to a 5- or 6-membered ring containing 1, 2 or 3 ring heteroatoms; a cyclohexyl ring fused to a 5- or 6-membered heteroaromatic ring containing 1, 2 or 3 ring heteroatoms; and a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The terms "cyclic allylic compound" or "cyclic allylic substrate" synonymously refer to a cyclic compound having an allylic moiety (i.e. —C=C—C—) forming part of the ring. Given the level of generality to which the process of the present invention is applicable, it will be appreciated by one of ordinary skill in the art that the cyclic allylic compound may contain a variety of substitution patterns and/or be fused to other cyclic systems.

The term "allylic carbon" or "allylic site" synonymously refer to the saturated carbon of the allylic moiety.

The term "pre-catalyst based on M" refers to a metallic complex containing metal M that functions in conjunction with the chiral ligand to catalyse the process of the invention. For the purpose of this invention, the terms "pre-catalyst" and "catalyst" may be used interchangeably.

Processes of the Invention

As described hereinbefore, the present invention provides a process for the formation of a $C_{sp3}$—$C_{sp2}$ bond at the allylic carbon of a cyclic allylic compound, the process comprising the step of:
  a) reacting a racemic mixture of a cyclic allylic compound having a leaving group attached to the allylic carbon with a compound having a nucleophilic carbon atom, wherein step a) is conducted in the presence of:
    i) a pre-catalyst based on Rh(I), Pd(II) or Cu(I); and
    ii) a chiral ligand
and wherein the formation of the $C_{sp3}$—$C_{sp2}$ bond results in the generation of a product compound in a stereoisomeric excess.

In spite of the prior art's focus on asymmetric allylic alkylation reactions, the inventors have now surprising found that $sp^2$-hybridised nucleophiles (e.g. alkenyl or aryl) can be coupled to $sp^3$ carbons of cyclic allylic compounds in high yield and stereoisomeric excess using metallic complex based on Rh(I), ), Pd(II) or Cu(I), together with a chiral ligand. These DYKATs can be conducted in mild and robust reaction conditions, and are widely applicable to a variety of substrates and nucleophiles. In particular, the presence of electron-withdrawing groups or electron-donating groups on the nucleophile does not hamper the observed high yields and stereoisomeric excesses. Similarly, the ring moiety of the cyclic allylic substrate may be wholly carbon, or one or more heteroatoms may be incorporated into it without compromising the reaction's applicability. In addition, results generated show that the process can be easily scaled up, and the quantity of catalyst can be significantly reduced, without an attendant drop off in yield and stereoisomeric excess. It is anticipated that the process will allow for the preparation of a wide variety of enantiomerically pure building blocks for synthetic, medicinal (notably pharmaceutical) and materials chemistry.

Those of skill in the art will—having regard to the diverse exemplification provided herein—appreciate the broad applicability of the process of the invention in terms of the structures of the cyclic allylic compound and the compound having a nucleophilic carbon atom. In particular, it will be understood from the diverse exemplification provided herein that the $C_{sp3}$—$C_{sp2}$ bond formation at the allylic carbon of the cyclic allyl compound proceeds in a high yield and stereoisomeric excess for a variety of different substrates and nucleophiles. Hence, providing that the reagents possess the essential chemical elements of the present process (namely the allyl carbon of the cyclic allylic compound and the nuceophilic carbon of the compound having a nucleophilic carbon), a variety of structural modifications (including one or more different substituents, and the presence of fused cyclic moieties and spiro-linked moieties) are conceivable.

In an embodiment, the product compound formed in a stereoisomeric excess has a structure according to formula I shown below:

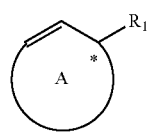

(I)

wherein
ring A is a 4-8 membered carbocyclyl or heterocyclyl ring optionally fused to one or more rings B, wherein rings A and B are each independently optionally substituted with one or more groups selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl(1-3C) alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-8C)alkyl, (2-8C)alkenyl, (2-8C)alkynyl, halo, trifluoromethyl, trifluoromethoxy, cyano, nitro, hydroxyl, amino, (1-8C) haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl(1-3C)alkyl, 4-6 membered carbocyclyl(1-3C) alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy;
$R_1$ is selected from aryl or heteroaryl, either of which may be optionally fused to one or more rings C, and/or optionally substituted with one or more substituents selected from oxo, (1-8C)alkyl, (2-8C)alkenyl, (2-8C) alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl(1-3C)alkyl, 4-6 membered carbocyclyl(1-3C) alkoxy, 4-6 membered heterocyclyl, 4-6 membered heterocyclyl(1-3C)alkyl, 4-6 membered heterocyclyl (1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy
  each ring C is monocyclic or bicyclic aryl or heteroaryl, either of which is optionally substituted with one or more groups selected from oxo, (1-8C)alkyl, (2-8C) alkenyl, (2-8C)alkynyl, halo, trifluoromethyl, trifluoromethoxy, cyano, nitro, hydroxyl, amino, (1-8C) haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy;

or $R_1$ is a group

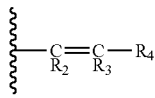

wherein $R_2$, $R_3$ and $R_4$ are independently selected from i) H, (1-8C)alkyl, (2-8C)alkenyl, (2-8C)alkynyl, halo, trifluoromethyl, trifluoromethoxy, cyano, nitro, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3) or $(O)_zSi(R_a)_3$ or $(O)_zSi(OR_a)_3$ (wherein z is 0 or 1); or ii) 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C)alkoxy, the cyclic moieties of which may be optionally substituted with one or more substituents selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy;

and wherein each of $R_a$ and $R_b$ are independently selected from H or (1-6C)alkyl, (2-6C)alkenyl or (2-6C)alkynyl.

Pre-Catalyst

The pre-catalyst based on Rh(I), Pd(II) or Cu(I) is any metallic complex based on Rh(I), Pd(II) or Cu(I) that is capable of releasably binding the chiral ligand and thereby acting as a catalyst for the process of the invention. It will be understood by one of orginary skill in the art that a variety of different metallic complexes based on Rh(I), Pd(II) or Cu(I) could be effectively used as part of the present invention.

In an embodiment, the pre-catalyst is based on Rh(I) or Pd(II). Suitably, the pre-catalyst is based on Rh(I).

It will be appreciated that a broad spectrum of Rh(I) metal complex could be effectively employed as pre-catalysts as part of the present invention. In an embodiment, the Rh(I) pre-catalyst may take the form of a monomer (e.g. Rh(acac)$(C_2H_4)_2$, Rh(acac)(COD) or Rh(acac)(norbornadiene)), a dimer (e.g. $[Rh(COD)(OH)]_2$, $[Rh(COD)(Cl)]_2$ or [Rh(2-phenylpyridine)(Cl)]$_2$ or an oligomer.

In another embodiment, the Rh(I) pre-catalyst comprises two or more ligands selected from halo, OH, $OR_x$ (wherein $R_x$ is (1-8C)alkyl), (1-10C)alkenyl or $R_yCHC(O)R_z$ (wherein $R_y$ is (1-6C)alkyl and $R_z$ is (1-6C)alkyl or acetyl).

In another embodiment, the Rh(I) pre-catalyst is selected from Rh(acac)$(C_2H_4)_2$, Rh(acac)(COD), $[Rh(COD)(Cl)]_2$) or $[Rh(COD)(OH)]_2$). Suitably, the Rh(I) pre-catalyst is $[Rh(COD)(OH)]_2$.

In another embodiment, the quantity of pre-catalyst used is greater than 0.25 mol %. Suitably, the quantity of pre-catalyst used is greater than or equal to 0.3 mol %. More suitably, the quantity of pre-catalyst used is greater than 0.5 mol %.

Chiral Ligand

It will be appreciated that any suitable chiral ligand may be effectively employed in the present process. Suitably, the chiral ligand is non-racemic (i.e. it is present in a stereoisomeric excess).

In an embodiment, the chiral ligand is a monodentate, bidentate or tridentate ligand. Suitably, the chiral ligand is a phosphorus-containing ligand or a diene ligand.

In another embodiment, the chiral ligand is selected from monophosphines, monophosphites, monophosphinites, monophosphonites, bisphosphines, bisphosphites, bisphosphinites, bisphosphonites, phosphoramidites or dienes. Suitably, the chiral ligand is selected from monophosphines, bisphosphines, monophosphinite, bisphosphinite, phosphoramidite and dienes.

Exemplary phosphine ligands include, but are not limited to, the following compounds:

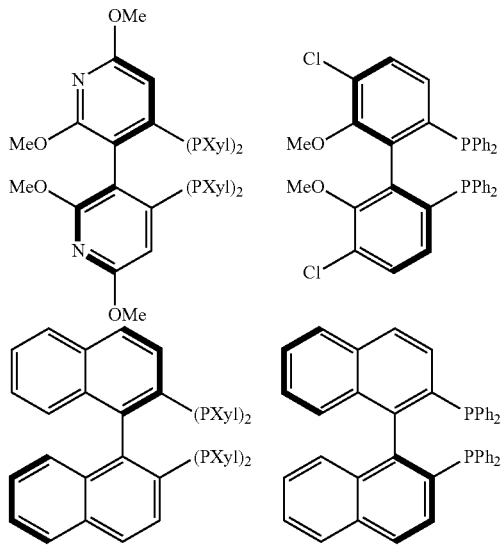

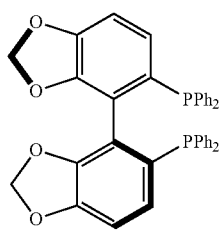

Exemplary phosphoramidite ligands include, but are not limited to, the following compound:

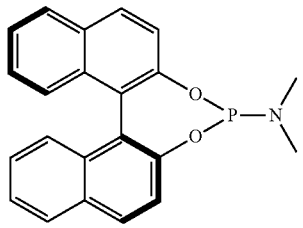

Exemplary diene ligands include, but are not limited to, the following compounds:

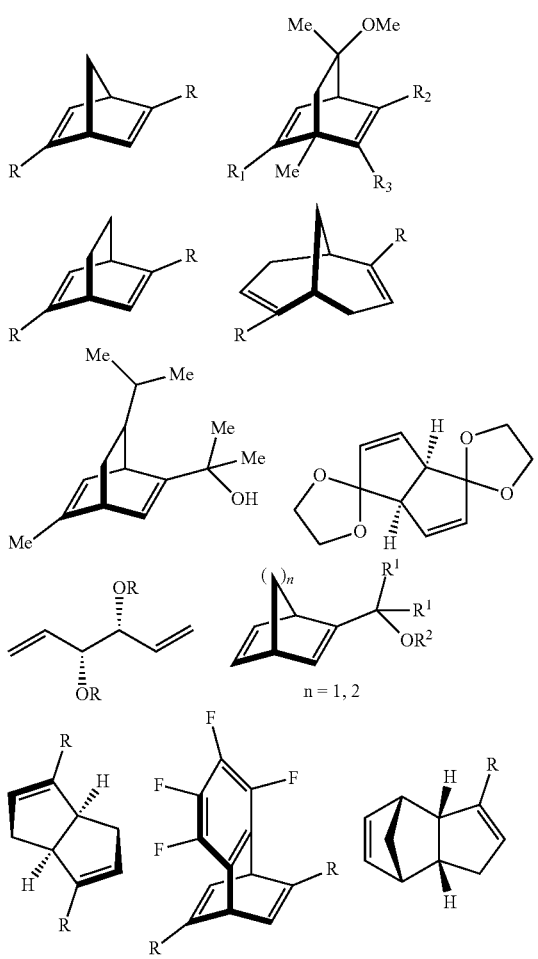

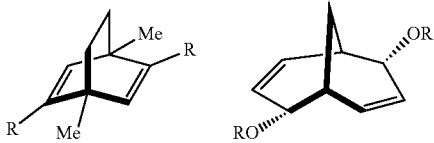

In a particular embodiment, the chiral ligand is (S)-Xyl-P—PHOS shown below:

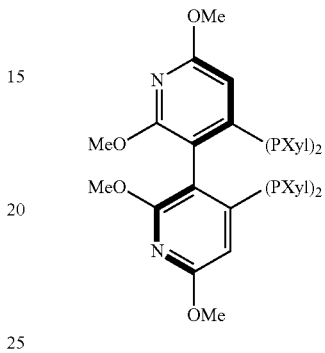

Cyclic Allylic Compound

As discussed hereinbefore, it will be understood that the terms "cyclic allylic compound" or "cyclic allylic substrate" synonymously refer to a cyclic compound having an allylic moiety (i.e. —C=C—C—) forming part of the ring. In this sense, the cyclic allylic compounds forming part of the present invention cannot be considered allylic solely by the presence of an allylic substituent present on the ring. The cyclic allylic compounds possess a leaving group bonded to the allylic carbon. For illustrative purposes only, generalised cyclic allylic compounds useful as part of the present invention include the following moieties:

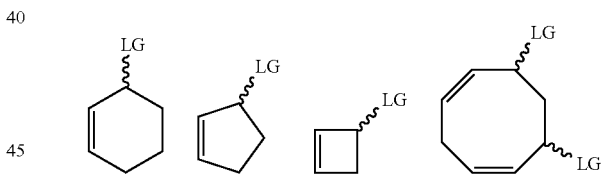

Given the general level of applicability of the present invention, it will be appreciated by one of ordinary skill in the art that the cyclic allylic compound may contain a variety of substitution patterns and/or be fused to other cyclic systems. Hence, it will be understood that the illustrative moieties outlined above are highly generalised, and may therefore additionally include, for example, one or more ring heteroatoms, one or more ring substituents, one or more additional cyclic systems fused to the cyclic allylic compound, and/or one or more spiro moieties, providing that such modifications are chemically feasible. The cyclic allylic compound is presented as a racemate having regard to the chiral allylic carbon. Other stereocentres may also be present and stereoisomers may be present in any ratio.

In an embodiment, the $sp^3$ ayllic carbon of the cyclic allylic compound is bonded to a leaving group and a hydrogen atom.

In another embodiment, the leaving group is any suitable leaving group. Suitably, the leaving group is selected from halo, phosphate, sulfonate, sulfinate, sulphonamide, carboxylate, carbonate, thiolate and nitrate. Suitably, the leaving group is halo, selected from Cl, Br and I.

In another embodiment, the cyclic allylic compound has a structure according to formula (II) shown below:

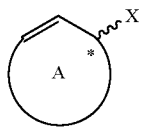

(II)

wherein
ring A is a 4-8 membered carbocyclyl or heterocyclyl ring optionally fused to one or more rings B, wherein rings A and B are each independently optionally substituted with one or more groups selected from oxo, (1-8C) alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-8C)alkyl, (2-8C)alkenyl, (2-8C)alkynyl, halo, trifluoromethyl, trifluoromethoxy, cyano, nitro, hydroxyl, amino, (1-8C) haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl (1-3C)alkyl, 4-6 membered carbocyclyl(1-3C) alkoxy, 4-6 membered heterocyclyl, 4-6 membered heterocyclyl(1-3C)alkyl, 4-6 membered heterocyclyl (1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl (1-3C)alkoxy;
X is a leaving group;
and wherein each of $R_a$ and $R_b$ are independently selected from H or (1-6C)alkyl, (2-6C)alkenyl or (2-6C)alkynyl.

In another embodiment, the cyclic allylic compound has a structure according to formula (II), wherein
ring A is a 4-8 membered carbocyclyl or heterocyclyl ring (containing one or more heteroatoms selected from N, S and O) optionally fused to one or more rings B, wherein rings A and B are each independently optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;
X is a leaving group;
and wherein each of $R_a$ and $R_b$ are independently selected from H or (1-6C)alkyl, (2-6C)alkenyl or (2-6C)alkynyl.

In another embodiment, the cyclic allylic compound has a structure according to formula (II), wherein
ring A is a 5-7 membered carbocyclyl or heterocyclyl ring (containing one or more heteroatoms selected from N, S and O) optionally fused to one or more rings B, wherein rings A and B are each independently optionally substituted with one or more groups selected from oxo, (1-6C)alkyl, (2-6C)alkenyl, (2-6C)alkynyl, halo, trifluoromethyl, cyano, nitro, hydroxyl, amino, (1-6C) alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-6C)alkyl, (2-6C)alkenyl, (2-6C)alkynyl, halo, trifluoromethyl, cyano, nitro, hydroxyl, amino, (1-6C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;
X is a leaving group;
and wherein each of $R_a$ and $R_b$ are independently selected from H or (1-6C)alkyl, (2-6C)alkenyl or (2-6C)alkynyl.

In another embodiment, the cyclic allylic compound has a structure according to formula (II), wherein
ring A is a 5-7 membered carbocyclyl or heterocyclyl ring (containing 1, 2 or 3 heteroatoms selected from N, S and O) optionally fused to one or more rings B, wherein rings A and B are each independently optionally substituted with one or more groups selected from oxo, (1-6C)alkyl, (2-6C)alkenyl, (2-6C)alkynyl, halo, trifluoromethyl, nitro, hydroxyl, amino, (1-6C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or (O)$_z$Si(OR$_a$)$_3$ (wherein z is 0 or 1), 4-6 membered carbocyclyl, 4-6 membered heterocyclyl, phenyl or 5-6 membered heteroaryl;
wherein
each ring B is independently 5-6 membered carbocyclyl, 6 membered aryl, 5-6 membered heterocyclyl or 5-6 membered heteroaryl, any of which may be optionally substituted with one or more groups selected from oxo, (1-6C)alkyl, (2-6C)alkenyl, (2-6C)alkynyl, halo, trifluoromethyl, hydroxyl, amino, (1-6C)alkoxy, carboxyl, NR$_a$R$_b$, OR$_a$, C(O)R$_a$, C(O)OR$_a$, OC(O)R$_a$, (CH$_2$)$_y$NR$_a$R$_b$ (where y is 1, 2 or 3), (O)$_z$Si(R$_a$)$_3$ or (O)$_z$Si(OR$_a$)$_3$ (wherein z is 0 or 1), 4-6 membered carbocyclyl, 4-6 membered heterocyclyl, phenyl or 5-6 membered heteroaryl;
X is a leaving group;
and wherein each of R$_a$ and R$_b$ are independently selected from H or (1-6C)alkyl, (2-6C)alkenyl or (2-6C)alkynyl.

In another embodiment, the cyclic allylic compound has a structure according to formula (II), wherein
ring A is a 5-7 membered carbocyclyl or heterocyclyl ring (containing 1, 2 or 3 heteroatoms selected from N, S and O) optionally fused to one or more rings B, wherein rings A and B are each independently optionally substituted with one or more groups selected from oxo, (1-6C)alkyl, (2-6C)alkenyl, (2-6C)alkynyl, halo, amino, (1-6C)alkoxy, carboxyl, NR$_a$R$_b$, OR$_a$, C(O)OR$_a$, OC(O)R$_a$, (CH$_2$)$_y$NR$_a$R$_b$ (where y is 1, 2 or 3), (O)$_z$Si(R$_a$)$_3$ (wherein z is 0 or 1), phenyl or 5-6 membered heteroaryl;
wherein
each ring B is independently 5-6 membered carbocyclyl, 6 membered aryl, 5-6 membered heterocyclyl or 5-6 membered heteroaryl, any of which may be optionally substituted with one or more groups selected from oxo, (1-6C)alkyl, (2-6C)alkenyl, (2-6C)alkynyl, halo, amino, (1-6C)alkoxy, NR$_a$R$_b$, OR$_a$, C(O)OR$_a$, OC(O)R$_a$, (CH$_2$)$_y$NR$_a$R$_b$ (where y is 1, 2 or 3), (O)$_z$Si(R$_a$)$_3$ (wherein z is 0 or 1), phenyl or 5-6 membered heteroaryl;
X is a leaving group selected from Cl or Br;
and wherein each of R$_a$ and R$_b$ are independently selected from H or (1-6C)alkyl, (2-6C)alkenyl or (2-6C)alkynyl.

In another embodiment, the cyclic allylic compound has a structure according to formula (II), wherein
ring A is a 5-7 membered carbocyclyl or heterocyclyl ring (containing 1 or 2 heteroatoms selected from N and O) optionally fused to one or more rings B, wherein rings A and B are each independently optionally substituted with one or more groups selected from oxo, (1-6C) alkyl, (2-6C)alkenyl, (2-6C)alkynyl, halo, amino, (1-6C)alkoxy, NR$_a$R$_b$, (CH$_2$)$_y$NR$_a$R$_b$ (where y is 1, 2 or 3), (O)$_z$Si(R$_a$)$_3$ (wherein z is 0 or 1), phenyl or 5-6 membered heteroaryl;
wherein
each ring B is independently 5-6 membered carbocyclyl, 6 membered aryl, 5-6 membered heterocyclyl or 5-6 membered heteroaryl, any of which may be optionally substituted with one or more groups selected from oxo, (1-6C)alkyl, (2-6C)alkenyl, (2-6C)alkynyl, halo, amino, (1-6C)alkoxy, NR$_a$R$_b$, (CH$_2$)$_y$NR$_a$R$_b$ (where y is 1, 2 or 3), (O)$_z$Si(R$_a$)$_3$ (wherein z is 0 or 1), phenyl or 5-6 membered heteroaryl;
X is a leaving group selected from Cl or Br;
and wherein each of R$_a$ and R$_b$ are independently selected from H or (1-6C)alkyl, (2-6C)alkenyl or (2-6C)alkynyl.

In another embodiment, the cyclic allylic compound has a structure according to formula (II), wherein
ring A is a 5-7 membered carbocyclyl or heterocyclyl ring (containing 1 or 2 heteroatoms selected from N and O) optionally fused to one or more rings B, wherein rings A and B are each independently optionally substituted with one or more groups selected from oxo, (1-6C)alkyl, (2-6C)alkenyl, (2-6C)alkynyl, halo, amino, (1-6C)alkoxy, C(O)OR$_a$, NR$_a$R$_b$, (CH$_2$)$_y$NR$_a$R$_b$ (where y is 1, 2 or 3), (O)$_z$Si(R$_a$)$_3$ (wherein z is 0 or 1), phenyl or 5-6 membered heteroaryl;
wherein
each ring B is independently 5-6 membered carbocyclyl, 6 membered aryl, 5-6 membered heterocyclyl or 5-6 membered heteroaryl, any of which may be optionally substituted with one or more groups selected from, (1-6C)alkyl, (2-6C)alkenyl, (2-6C)alkynyl, halo, amino, (1-6C)alkoxy, NR$_a$R$_b$, (CH$_2$)$_y$NR$_a$R$_b$ (where y is 1, 2 or 3), (O)$_z$Si(R$_a$)$_3$ (wherein z is 0 or 1), phenyl or 5-6 membered heteroaryl;
X is a leaving group selected from Cl or Br;
and wherein each of R$_a$ and R$_b$ are independently selected from H or (1-6C)alkyl, (2-6C)alkenyl or (2-6C)alkynyl.

Compound Having a Nucleophilic Carbon

It will be understood that the term "compound having a nucleophilic carbon" refers to any suitable compound having a nucleophilic carbon. Given the level of generality at which the present invention may operate, the person of ordinary skill in the art will appreciate that the compound having a nucleophilic carbon may take a variety of forms, including linear and cyclic compounds (including fused and spiro derivatives), and substituted and unsubstituted compounds. The compound having a nucleophilic carbon may take the form of a reagent, said reagent then reacting directly with the cyclic allylic compound in the manner described herein. Alternatively, the compound having a nucleophilic carbon may take the form of an intermediate compound that is formed in-situ prior to reaction with the cyclic allylic compound in the manner described herein.

In an embodiment, the nucleophilic carbon of the compound having a nucleophilic carbon is an sp$^2$ carbon.

In another embodiment, the compound having a nucleophilic carbon is not a zirconocene compound (e.g. an alkenyl zirconocene).

In another embodiment, the compound having a nucleophilic carbon atom has a structure according to formula (III) shown below:

$$Z-R_1 \qquad (III)$$

wherein
R$_1$ is selected from aryl or heteroaryl, either of which may be optionally fused to one or more rings C, and/or optionally substituted with one or more substituents selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, NR$_a$R$_b$, OR$_a$, C(O)R$_a$, C(O)OR$_a$, OC(O)R$_a$, C(O)N(R$_b$)R$_a$, N(R$_b$)C(O)R$_a$, S(O)$_x$R$_a$ (where x is 0, 1 or 2), SO$_2$N(R$_b$)R$_a$, N(R$_b$)SO$_2$R$_a$, (CH$_2$)$_y$NR$_a$R$_b$ (where y is 1, 2 or 3), (O)$_z$Si(R$_a$)$_3$ or (O)$_z$Si(OR$_a$)$_3$ (wherein z is 0 or 1), 4-6 membered carbocyclyl, 4-6 membered carbocyclyl(1-3C)alkyl, 4-6 membered carbocyclyl(1-3C)

alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy each ring C is monocyclic or bicyclic aryl or heteroaryl, either of which is optionally substituted with one or more groups selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy;

or $R_1$ is a group

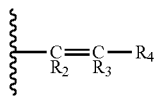

wherein $R_2$, $R_3$ and $R_4$ are independently selected from i) H, (1-8C)alkyl, (2-8C)alkenyl, (2-8C)alkynyl, halo, trifluoromethyl, trifluoromethoxy, cyano, nitro, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3) or $(O)_zSi(R_a)_3$ or $(O)_zSi(OR_a)_3$ (wherein z is 0 or 1); or ii) 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C)alkoxy, the cyclic moieties of which may be optionally substituted with one or more substituents selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$ (where x is 0, 1 or 2), $SO_2N(R_b)R_a$, $N(R_b)SO_2R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, or 5-6 membered heteroaryl(1-3C)alkoxy;

each of $R_a$ and $R_b$ are independently selected from H or (1-6C)alkyl, (2-6C)alkenyl or (2-6C)alkynyl; and Z is selected from one of the following options:
(i) Z is H;
(ii) when taken with $R_1$, Z forms a boronic acid, or a boronic acid derivative;
(iii) Z is a metal selected from Si, Zn, Bi, Mg, Ti or Sn, said metal being optionally associated with one or more groups selected from halo, hydroxyl, (1-4C)alkyl, (1-4C)alkoxy, or aryl, such that the compound of formula III is an organometallic nucleophile; or
(iv) Z is a group $B(Y_3)_3^- M^+$, wherein $Y_3$ is selected from halo or (1-4C)alkoxy and M is a cation selected from $Na^+$, $K^+$ and $Li^+$.

The term "boronic acid derivative" will be readily understood by the person of ordinary skill in the art. Notable boronic acid derivative, including methods for their preparation, are discussed extensively in Boronic Acids: Preparation and Applications in Organic Synthesis, Medicine and Materials, Dennis G. Hall[19].

In another embodiment, the compound having a nucleophilic carbon atom has a structure according to formula (III), wherein $R_1$ is selected from aryl or heteroaryl, either of which may be optionally fused to one or more rings C, and/or optionally substituted with one or more substituents selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl, phenyl(1-3C)alkyl, phenyl(1-3C)alkoxy or 5-6 membered heteroaryl;

each ring C is monocyclic or bicyclic aryl or heteroaryl, either of which is optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;

or $R_1$ is a group

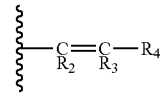

wherein $R_2$, $R_3$ and $R_4$ are independently selected from
i) H, (1-8C)alkyl, (2-8C)alkenyl, (2-8C)alkynyl, halo, trifluoromethyl, cyano, nitro, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3) or $(O)_zSi(R_a)_3$ or $(O)_zSi(OR_a)_3$ (wherein z is 0 or 1); or
ii) 4-6 membered carbocyclyl, 4-6 membered heterocyclyl, phenyl, phenyl(1-3C)alkyl and 5-6 membered heteroaryl, the cyclic moieties of which may be optionally substituted with one or more substituents selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl; and each of $R_a$ and $R_b$ are independently selected from H or (1-6C)alkyl, (2-6C)alkenyl or (2-6C)alkynyl.

In another embodiment, the compound having a nucleophilic carbon atom has a structure according to formula (III), wherein $R_1$ is selected from phenyl or 5-6 membered heteroaryl, either of which may be optionally fused to one or more rings C, and/or optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl, phenyl(1-3C)alkyl, phenyl(1-3C)alkoxy or 5-6 membered heteroaryl;

each ring C is monocyclic or bicyclic aryl or heteroaryl, either of which is optionally substituted with one or more groups selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;

or $R_1$ is a group

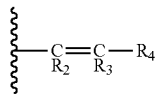

wherein $R_2$, $R_3$ and $R_4$ are independently selected from
i) H, (1-6C)alkyl, (2-6C)alkenyl, (2-6C)alkynyl, halo, trifluoromethyl, cyano, nitro, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3) or $(O)_zSi(R_a)_3$ or $(O)_zSi(OR_a)_3$ (wherein z is 0 or 1); or
ii) 4-6 membered carbocyclyl, 4-6 membered heterocyclyl, phenyl, phenyl(1-3C)alkyl and 5-6 membered heteroaryl, the cyclic moieties of which may be optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl; and
each of $R_a$ and $R_b$ are independently selected from H or (1-6C)alkyl, (2-6C)alkenyl or (2-6C)alkynyl.

In another embodiment, the compound having a nucleophilic carbon atom has a structure according to formula (III), wherein $R_1$ is selected from phenyl or 5-6 membered heteroaryl (containing 1, 2 or 3 heteroatoms selected from N, O and S), either of which may be optionally fused to one or more rings C, and/or optionally substituted with one or more substituents selected from oxo, (1-6C)alkyl, (2-6C)alkenyl, (2-6C)alkynyl, halo, trifluoromethyl, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl, phenyl(1-3C)alkyl, phenyl(1-3C)alkoxy or 5-6 membered heteroaryl;

each ring C is monocyclic or bicyclic aryl or heteroaryl, either of which is optionally substituted with one or more groups selected from oxo, (1-6C)alkyl, (2-6C)alkenyl, (2-6C)alkynyl, halo, trifluoromethyl, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;

or $R_1$ is a group

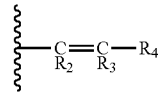

wherein $R_2$, $R_3$ and $R_4$ are independently selected from
i) H, (1-6C)alkyl, (2-6C)alkenyl, (2-6C)alkynyl, halo, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3) or $(O)_zSi(R_a)_3$ or $(O)_zSi(OR_a)_3$ (wherein z is 0 or 1); or
ii) 4-6 membered carbocyclyl, 4-6 membered heterocyclyl, phenyl, phenyl(1-3C)alkyl and 5-6 membered heteroaryl, the cyclic moieties of which may be optionally substituted with one or more substituents selected from oxo, (1-6C)alkyl, (2-6C)alkenyl, (2-6C)alkynyl, halo, trifluoromethyl, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl; and
each of $R_a$ and $R_b$ are independently selected from H or (1-6C)alkyl, (2-6C)alkenyl or (2-6C)alkynyl.

In another embodiment, the compound having a nucleophilic carbon atom has a structure according to formula (III), wherein $R_1$ is selected from phenyl or 5-6 membered heteroaryl (containing 1, 2 or 3 heteroatoms selected from N, O and S), either of which may be optionally fused to one or more rings C, and/or optionally substituted with one or more substituents selected from oxo, (1-6C)alkyl, (2-6C)alkenyl, (2-6C)alkynyl, halo, trifluoromethyl, nitro, hydroxyl, amino, (1-8C)alkoxy, $C(O)R_a$, $C(O)OR_a$, $OC(O)R_a$, $(CH_2)_yNR_aR_b$ (where y is 1, 2 or 3), (O)$_z$Si(R$_a$)$_3$ (wherein z is 0 or 1), 4-6 membered heterocyclyl, phenyl, phenyl(1-3C)alkyl, phenyl(1-3C)alkoxy or 5-6 membered heteroaryl;

each ring C is monocyclic or bicyclic aryl or heteroaryl, either of which is optionally substituted with one or more groups selected from oxo, (1-6C)alkyl, (2-6C)alkenyl, (2-6C)alkynyl, halo, trifluoromethyl, hydroxyl, amino, (1-8C)alkoxy, C(O)OR$_a$, OC(O)R$_a$, (CH$_2$)$_y$NR$_a$R$_b$ (where y is 1, 2 or 3), (O)$_z$Si(R$_a$)$_3$ (wherein z is 0 or 1), phenyl or 5-6 membered heteroaryl;

or R$_1$ is a group

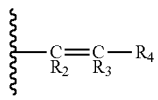

wherein

R$_2$, R$_3$ and R$_4$ are independently selected from
  i) H, (1-6C)alkyl, (2-6C)alkenyl, (2-6C)alkynyl, halo, (1-8C)alkoxy, C(O)OR$_a$, OC(O)R$_a$, (CH$_2$)$_y$NR$_a$R$_b$ (where y is 1, 2 or 3) or (O)$_z$Si(R$_a$)$_3$ (wherein z is 0 or 1); or
  ii) phenyl, phenyl(1-3C)alkyl and 5-6 membered heteroaryl, the cyclic moieties of which may be optionally substituted with one or more substituents selected from oxo, (1-6C)alkyl, (2-6C)alkenyl, (2-6C)alkynyl, halo, amino, (1-8C)alkoxy, carboxyl, NR$_a$R$_b$, OR$_a$, C(O)OR$_a$, OC(O)R$_a$, (CH$_2$)$_y$NR$_a$R$_b$ (where y is 1, 2 or 3), (O)$_z$Si(R$_a$)$_3$ (wherein z is 0 or 1), phenyl or 5-6 membered heteroaryl; and
    each of R$_a$ and R$_b$ are independently selected from H or (1-6C)alkyl, (2-6C)alkenyl or (2-6C)alkynyl.

In another embodiment, the compound having a nucleophilic carbon atom has a structure according to formula (III), wherein Z is selected from one of the following options:
  (i) Z is H;
  (ii) when taken with R$_1$, Z forms a boronic acid, or a boronic acid derivative;
  (iii) Z is a metal selected from Si, Zn, Bi, Mg, Ti or Sn, said metal being optionally associated with one or more groups selected from Cl, Br, hydroxyl, (1-4C)alkyl, (1-4C)alkoxy, or phenyl, such that the compound of formula III is an organometallic nucleophile; or
  (iv) Z is a group B(Y$_3$)$_3^-$ M$^+$, wherein Y$_3$ is selected from Cl, Br or (1-4C)alkoxy and M is a cation selected from K$^+$ and Li$^+$.

In another embodiment, the compound having a nucleophilic carbon atom has a structure according to formula (III), wherein when taken with R$_1$, Z forms a boronic acid, or a boronic acid derivative.

In a particular embodiment, the compound having a nucleophilic carbon atom has a structure according to formula (III), wherein when taken with R$_1$, Z forms a boronic acid, R$_1$—B(OH)$_2$.

Reaction Conditions

In an embodiment of the process of the present invention, the process is performed in the presence of a base. A base may be necessary depending on the nature of the leaving group present on the cyclic allylic compound. Suitably, where the leaving group is halo, the process is carried out in the presence of a base.

Any suitable base may be used. Exemplary bases include, but are not limited to, Cs$_2$CO$_3$, CsOH, K$_2$CO$_3$, NaHCO$_3$, NaOtBu, MTBD (7-Methyl-1,5,7-triazabicyclo(4.4.0)dec-5-ene), KOH, NaOH, LiOH, Ba(OH)$_2$, Et$_3$N and K$_3$PO$_4$. Suitably, the base is Cs$_2$CO$_3$.

In another embodiment, the stereoisomeric excess of the product compound is not substantially increased by performing the process at cryogenic temperatures. Suitably, the stereoisomeric excess of the product compound is not substantially increased by performing the process at a temperature between 0 and −50° C. More suitably, the stereoisomeric excess of the product compound is not substantially increased by performing the process at a temperature between 25 and −50° C. Hence, in another embodiment, the process is not performed at any one of these temperatures.

The skilled person will appreciate that any suitable solvent may be used as part of the present process. In an embodiment, the solvent is selected from THF, dioxane, toluene, dimethoxyethane, H$_2$O (for example when the leaving group present on the cyclic allylic compound is other than halo), benzene, 2-methyl-THF, MeOH, Et$_2$O and Me-O-cyclopentane. Suitably, the process is performed in THF as a solvent.

Other suitable reaction conditions (e.g. pressures, etc) will be readily determinable by one of ordinary skill in the art.

Particular Embodiments

Particular embodiments of the invention are outlined in the following numbered paragraphs (1)-(11):

(1) A process as described herein, wherein
  the pre-catalyst is based on Rh(I) or Pd(II);
  the chiral ligand is non-racemic; and
  the process is optionally additionally performed in the presence of a base.

(2) A process as described herein, wherein
  the pre-catalyst is based on Rh(I);
  the chiral ligand is a non-racemic phosphorus-containing or diene ligand; and
  the process is optionally additionally performed in the presence of a base.

(3) A process as described herein, wherein
  the pre-catalyst is based on Rh(I) and takes the form of a monomer, dimer or oligomer;
  the chiral ligand is a non-racemic ligand selected from monophosphines, monophosphites, monophosphinites, monophosphonites, bisphosphines, bisphosphites, bisphosphinites, bisphosphonites, phosphoramidites or dienes; and
  the process is optionally additionally performed in the presence of a base.

(4) A process as described herein, wherein
  the pre-catalyst is based on Rh(I) and comprises two or more ligands selected from halo, OH, OR$_x$ (wherein R$_x$ is (1-8C)alkyl), (1-10C)alkenyl or R$_y$CHC(O)R$_z$ (wherein R$_y$ is (1-6C)alkyl and R$_z$ is (1-6C)alkyl or acetyl);
  the chiral ligand is a non-racemic ligand selected from monophosphines, monophosphites, monophosphinites, monophosphonites, bisphosphines, bisphosphites, bisphosphinites, bisphosphonites, phosphoramidites or dienes; and the process is optionally additionally performed in the presence of a base.

(5) A process as described herein, wherein
the cyclic allylic compound has a structure according to formula (II), wherein ring A and X have any of the definitions recited herein;
the pre-catalyst is based on Rh(I) and comprises two or more ligands selected from halo, OH, $OR_x$ (wherein $R_x$ is (1-8C)alkyl), (1-10C)alkenyl or $R_yCHC(O)R_z$ (wherein $R_y$ is (1-6C)alkyl and $R_z$ is (1-6C)alkyl or acetyl);
the chiral ligand is a non-racemic ligand selected from monophosphines, monophosphites, monophosphinites, monophosphonites, bisphosphines, bisphosphites, bisphosphinites, bisphosphonites, phosphoramidites or dienes; and
the process is optionally additionally performed in the presence of a base.

(6) A process as described herein, wherein
the cyclic allylic compound has a structure according to formula (II),
wherein
ring A is a 4-8 membered carbocyclyl or heterocyclyl ring (containing one or more heteroatoms selected from N, S and O) optionally fused to one or more rings B, wherein rings A and B are each independently optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroary
X has any of the definitions recited herein;
the pre-catalyst is based on Rh(I) and comprises two or more ligands selected from halo, OH, $OR_x$ (wherein $R_x$ is (1-8C)alkyl), (1-10C)alkenyl or $R_yCHC(O)R_z$ (wherein $R_y$ is (1-6C)alkyl and $R_z$ is (1-6C)alkyl or acetyl);
the chiral ligand is a non-racemic ligand selected from monophosphines, monophosphites, monophosphinites, monophosphonites, bisphosphines, bisphosphites, bisphosphinites, bisphosphonites, phosphoramidites or dienes; and the process is optionally additionally performed in the presence of a base.

(7) A process as described herein, wherein
the cyclic allylic compound has a structure according to formula (II),
wherein
ring A is a 4-8 membered carbocyclyl or heterocyclyl ring (containing one or more heteroatoms selected from N, S and O) optionally fused to one or more rings B, wherein rings A and B are each independently optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroary;
wherein each of $R_a$ and $R_b$ are independently selected from H or (1-6C)alkyl, (2-6C)alkenyl or (2-6C)alkynyl
X has any of the definitions recited herein;
the pre-catalyst is based on Rh(I) and comprises two or more ligands selected from halo, OH, $OR_x$ (wherein $R_x$ is (1-8C)alkyl), (1-10C)alkenyl or $R_yCHC(O)R_z$ (wherein $R_y$ is (1-6C)alkyl and $R_z$ is (1-6C)alkyl or acetyl);
the chiral ligand is a non-racemic ligand selected from monophosphines, monophosphites, monophosphinites, monophosphonites, bisphosphines, bisphosphites, bisphosphinites, bisphosphonites, phosphoramidites or dienes; and the process is optionally additionally performed in the presence of a base.

(8) A process as described herein, wherein
the cyclic allylic compound has a structure according to formula (II), wherein ring A and X have any of the definitions recited herein;
the compound having a nucleophilic carbon has a structure according to formula (III), wherein Z and $R_1$ have any of the definitions recited herein;
the pre-catalyst is based on Rh(I) and comprises two or more ligands selected from halo, OH, $OR_x$ (wherein $R_x$ is (1-8C)alkyl), (1-10C)alkenyl or $R_yCHC(O)R_z$ (wherein $R_y$ is (1-6C)alkyl and $R_z$ is (1-6C)alkyl or acetyl);
the chiral ligand is a non-racemic ligand selected from monophosphines, monophosphites, monophosphinites, monophosphonites, bisphosphines, bisphosphites, bisphosphinites, bisphosphonites, phosphoramidites or dienes; and
the process is optionally additionally performed in the presence of a base.

(9) A process as described herein, wherein
the cyclic allylic compound has a structure according to formula (II), wherein ring A and X have any of the definitions recited herein;
the compound having a nucleophilic carbon has a structure according to formula (III), wherein
$R_1$ is selected from phenyl or 5-6 membered heteroaryl, either of which may be optionally fused to one or more rings C, and/or optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl, phenyl(1-3C)alkyl, phenyl (1-3C)alkoxy or 5-6 membered heteroaryl;

each ring C is monocyclic or bicyclic aryl or heteroaryl, either of which is optionally substituted with one or more groups selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;

or $R_1$ is a group

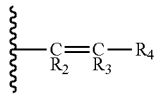

wherein $R_2$, $R_3$ and $R_4$ are independently selected from
i) H, (1-6C)alkyl, (2-6C)alkenyl, (2-6C)alkynyl, halo, trifluoromethyl, cyano, nitro, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3) or $(O)_zSi(R_a)_3$ or $(O)_zSi(OR_a)_3$ (wherein z is 0 or 1); or
ii) 4-6 membered carbocyclyl, 4-6 membered heterocyclyl, phenyl, phenyl(1-3C)alkyl and 5-6 membered heteroaryl, the cyclic moieties of which may be optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;

each of $R_a$ and $R_b$ are independently selected from H or (1-6C)alkyl, (2-6C)alkenyl or (2-6C)alkynyl;

Z is selected from one of the following options:
(i) Z is H;
(ii) when taken with $R_1$, Z forms a boronic acid, or a boronic acid derivative;
(iii) Z is a metal selected from Si, Zn, Bi, Mg, Ti or Sn, said metal being optionally associated with one or more groups selected from Cl, Br, hydroxyl, (1-4C)alkyl, (1-4C)alkoxy, or phenyl, such that the compound of formula III is an organometallic nucleophile; or
(iv) Z is a group $B(Y_3)_3^- M^+$, wherein $Y_3$ is selected from Cl, Br or (1-4C)alkoxy and M is a cation selected from $K^+$ and $Li^+$.

the pre-catalyst is based on Rh(I) and comprises two or more ligands selected from halo, OH, $OR_x$ (wherein $R_x$ is (1-8C)alkyl), (1-10C)alkenyl or $R_yCHC(O)R_z$ (wherein $R_y$ is (1-6C)alkyl and $R_z$ is (1-6C)alkyl or acetyl);

the chiral ligand is a non-racemic ligand selected from monophosphines, monophosphites, monophosphinites, monophosphonites, bisphosphines, bisphosphites, bisphosphinites, bisphosphonites, phosphoramidites or dienes; and the process is optionally additionally performed in the presence of a base.

(10) A process as described herein, wherein
the cyclic allylic compound has a structure according to formula (II), wherein ring A and X have any of the definitions recited herein;

the compound having a nucleophilic carbon has a structure according to formula (III), wherein
$R_1$ is selected from phenyl or 5-6 membered heteroaryl, either of which may be optionally fused to one or more rings C, and/or optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl, phenyl(1-3C)alkyl, phenyl (1-3C)alkoxy or 5-6 membered heteroaryl;

each ring C is monocyclic or bicyclic aryl or heteroaryl, either of which is optionally substituted with one or more groups selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;

or $R_1$ is a group

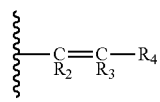

wherein $R_2$, $R_3$ and $R_4$ are independently selected from
i) H, (1-6C)alkyl, (2-6C)alkenyl, (2-6C)alkynyl, halo, trifluoromethyl, cyano, nitro, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3) or $(O)_zSi(R_a)_3$ or $(O)_zSi(OR_a)_3$ (wherein z is 0 or 1); or
ii) 4-6 membered carbocyclyl, 4-6 membered heterocyclyl, phenyl, phenyl(1-3C)alkyl and 5-6 membered heteroaryl, the cyclic moieties of which may be optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$ (where y is 1, 2 or 3), $(O)_zSi(R_a)_3$ or $(O)_zSi(OR_a)_3$ (wherein z is 0 or 1), 4-6 membered carbocyclyl, 4-6 membered heterocyclyl, phenyl or 5-6 membered heteroaryl;

each of $R_a$ and $R_b$ are independently selected from H or (1-6C)alkyl, (2-6C)alkenyl or (2-6C)alkynyl;

Z, when taken in combination with $R_1$, forms a boronic acid or a boronic acid derivative;

the pre-catalyst is based on Rh(I) and comprises two or more ligands selected from halo, OH, $OR_x$ (wherein $R_x$ is (1-8C)alkyl), (1-10C)alkenyl or $R_y CHC(O)R_z$ (wherein $R_y$ is (1-6C)alkyl and $R_z$ is (1-6C)alkyl or acetyl);

the chiral ligand is a non-racemic ligand selected from monophosphines, monophosphites, monophosphinites, monophosphonites, bisphosphines, bisphosphites, bisphosphinites, bisphosphonites, phosphoramidites or dienes; and the process is optionally additionally performed in the presence of a base.

(11) A process as described herein, wherein the cyclic allylic compound has a structure according to formula (II), wherein ring A is a 5-7 membered carbocyclyl or heterocyclyl ring (containing 1, 2 or 3 heteroatoms selected from N, S and O) optionally fused to one or more rings B, wherein rings A and B are each independently optionally substituted with one or more groups selected from oxo, (1-6C)alkyl, (2-6C)alkenyl, (2-6C)alkynyl, halo, trifluoromethyl, nitro, hydroxyl, amino, (1-6C)alkoxy, carboxyl, $NR_a R_b$, $OR_a$, $C(O)R_a$, $C(O)OR_a$, $OC(O)R_a$, $(CH_2)_y NR_a R_b$ (where y is 1, 2 or 3), $(O)_z Si(R_a)_3$ or $(O)_z Si(OR_a)_3$ (wherein z is 0 or 1), 4-6 membered carbocyclyl, 4-6 membered heterocyclyl, phenyl or 5-6 membered heteroaryl;

wherein each ring B is independently 5-6 membered carbocyclyl, 6 membered aryl, 5-6 membered heterocyclyl or 5-6 membered heteroaryl, any of which may be optionally substituted with one or more groups selected from oxo, (1-6C)alkyl, (2-6C)alkenyl, (2-6C)alkynyl, halo, trifluoromethyl, hydroxyl, amino, (1-6C)alkoxy, carboxyl, $NR_a R_b$, $OR_a$, $C(O)R_a$, $C(O)OR_a$, $OC(O)R_a$, $(CH_2)_y NR_a R_b$ (where y is 1, 2 or 3), $(O)_z Si(R_a)_3$ or $(O)_z Si(OR_a)_3$ (wherein z is 0 or 1), 4-6 membered carbocyclyl, 4-6 membered heterocyclyl, phenyl or 5-6 membered heteroaryl;

X is a leaving group selected from Br and Cl;

and wherein each of $R_a$ and $R_b$ are independently selected from H or (1-6C)alkyl, (2-6C)alkenyl or (2-6C)alkynyl the compound having a nucleophilic carbon has a structure according to formula (III), wherein $R_1$ is selected from phenyl or 5-6 membered heteroaryl, either of which may be optionally fused to one or more rings C, and/or optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_a R_b$, $OR_a$, $C(O)R_a$, $C(O)OR_a$, $OC(O)R_a$, $(CH_2)_y NR_a R_b$ (where y is 1, 2 or 3), $(O)_z Si(R_a)_3$ or $(O)_z Si(OR_a)_3$ (wherein z is 0 or 1), 4-6 membered carbocyclyl, 4-6 membered heterocyclyl, phenyl, phenyl(1-3C)alkyl, phenyl(1-3C)alkoxy or 5-6 membered heteroaryl;

each ring C is monocyclic or bicyclic aryl or heteroaryl, either of which is optionally substituted with one or more groups selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_a R_b$, $OR_a$, $C(O)R_a$, $C(O)OR_a$, $OC(O)R_a$, $(CH_2)_y NR_a R_b$ (where y is 1, 2 or 3), $(O)_z Si(R_a)_3$ or $(O)_z Si(OR_a)_3$ (wherein z is 0 or 1), 4-6 membered carbocyclyl, 4-6 membered heterocyclyl, phenyl or 5-6 membered heteroaryl;

or $R_1$ is a group

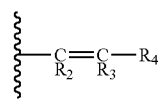

wherein $R_2$, $R_3$ and $R_4$ are independently selected from i) H, (1-6C)alkyl, (2-6C)alkenyl, (2-6C)alkynyl, halo, trifluoromethyl, cyano, nitro, (1-8C)alkoxy, carboxyl, $NR_a R_b$, $OR_a$, $C(O)R_a$, $C(O)OR_a$, $OC(O)R_a$, $(CH_2)_y NR_a R_b$ (where y is 1, 2 or 3) or $(O)_z Si(R_a)_3$ or $(O)_z Si(OR_a)_3$ (wherein z is 0 or 1); or ii) 4-6 membered carbocyclyl, 4-6 membered heterocyclyl, phenyl, phenyl(1-3C)alkyl and 5-6 membered heteroaryl, the cyclic moieties of which may be optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_a R_b$, $OR_a$, $C(O)R_a$, $C(O)OR_a$, $OC(O)R_a$, $(CH_2)_y NR_a R_b$ (where y is 1, 2 or 3), $(O)_z Si(R_a)_3$ or $(O)_z Si(OR_a)_3$ (wherein z is 0 or 1), 4-6 membered carbocyclyl, 4-6 membered heterocyclyl, phenyl or 5-6 membered heteroaryl;

each of $R_a$ and $R_b$ are independently selected from H or (1-6C)alkyl, (2-6C)alkenyl or (2-6C)alkynyl;

Z, when taken in combination with $R_1$, forms a boronic acid or a boronic acid derivative;

the pre-catalyst is based on Rh(I) and comprises two or more ligands selected from halo, OH, $OR_x$ (wherein $R_x$ is (1-8C)alkyl), (1-10C)alkenyl or $R_y CHC(O)R_z$ (wherein $R_y$ is (1-6C)alkyl and $R_z$ is (1-6C)alkyl or acetyl);

the chiral ligand is a non-racemic ligand selected from monophosphines, monophosphites, monophosphinites, monophosphonites, bisphosphines, bisphosphites, bisphosphinites, bisphosphonites, phosphoramidites or dienes; and the process is optionally additionally performed in the presence of a base, preferably being $Cs_2 CO_3$.

EXAMPLES

General Information

Procedures using oxygen- and/or moisture-sensitive materials were performed with anhydrous solvents (vide infra) under an atmosphere of anhydrous argon in flame-dried flasks, using standard Schlenk techniques. Analytical thin-layer chromatography was performed on precoated glass-backed plates (Silica Gel 60 F254; Merck) and visualised using a combination of UV light (254 nm) and aqueous ceric ammonium molybdate (CAM), aqueous basic potassium permanganate stains or vanillin solution. Flash column chromatography was carried out using Apollo Scientific silica gel 60 (0.040-0.063 nm), Merck 60 Å silica gel, VWR (40-63 µm) silica gel and Sigma Aldrich silica gel. Pressure was applied at the column head via a flow of nitrogen with the solvent system used in parentheses.

Reactions at 0° C. were performed using an ice-water bath, which was covered with cotton and foil if overnight stirring is required. Other temperatures were obtained using a Julabo FT902 immersion cooler or the heating plate of the stirrer.

Unless stated otherwise, solution NMR spectra were recorded at room temperature; $^1$H and $^{13}$C NMR experiments were carried out using Bruker AVG-400 (400/100 MHz), AVF-400 (400/100 MHz) or AVC-500 (500/125 MHz) spectrometers. Chemical shifts are reported in ppm from the residual solvent peak. Chemical shifts (δ) are given in ppm and coupling constants (J) are quoted in hertz (Hz). Resonances are described as s (singlet), d (doublet), t (triplet), q (quartet) and m (multiplet). Labels H and H' refer to diastereotopic protons attached to the same carbon and impart no stereochemical information. Assignments were made with the assistance of gCOSY, gHSQC, gHMBC or NOESY NMR spectra.

Chiral HPLC separations were achieved using an Agilent 1230 Infinity series normal phase HPLC unit and HP Chemstation software. Chiralpak® columns (250×4.6 mm), fitted with matching Chiralpak® Guard Cartridges (10×4 mm), were used as specified in the text. Solvents used were of HPLC grade (Fisher Scientific, Sigma Aldrich or Rathburn); all eluent systems were isocratic.

Chiral GC measurements were conducted on a HP6890 ($H_2$ as vector gas) or HP6850 ($H_2$ as vector gas) with the stated column in the characterization. Temperature programs are described as follows: initial temperature (° C.)–initial time (min)–temperature gradient (° C./min)–[certain temperature–holding time–temperature gradient (° C./min)]–final temperature (° C.)–holding time. Retention times (RT) are given in min.

Low-resolution mass spectra were recorded using a Walters LCT premier XE. High-resolution mass spectra (EI and ESI) were recorded using a Bruker MicroTOF spectrometer by the internal service at the University of Oxford.

Infrared measurements (neat, thin film) were carried out using a Bruker Tensor 27 FT-IR with internal calibration in the range 600-4000 cm$^{-1}$.

Optical rotations were recorded on a Perkin-Elmer 241 polarimeter at 20° C. in a 10 cm cell in the stated solvent; $[\alpha]_D$ values are given in 10$^{-1}$ deg·cm$^2$ g$^{-1}$ (concentration c given as g/100 mL).

General Chemicals

Dry THF and $CH_2Cl_2$ were collected fresh from an mBraun SPS-800 solvent purification system having been passed through anhydrous alumina columns. Dry 1,2-dichloroethane ether was purchased from Acros with an AcroSeal® respectively.

Unless stated otherwise, commercially available reagents were purchased from Sigma-Aldrich, Fisher Scientific, Apollo Scientific, Acros Organics, Strem Chemicals, Alfa Aesar or TCI UK and were used without purification. Deuterated solvents were purchased from Sigma-Aldrich ($CD_2Cl_2$, $CDCl_3$).

The cyclic allylic chlorides (1), 3-chloro-3,6-dihydro-2H-pyran (2) and 3-chloro-5-phenylcyclohex-1-ene were prepared according to reported methods. 3-bromocyclohex-1-ene was purchased from ACROS and used without further purification.

Example 1—Preparation of (−)-(S)-Cyclohex-2-enylbenzene 2

Using 3-chlorocyclohexene, [Rh(cod)(OH)]$_2$ and (S)-Xyl-P—PHOS 1

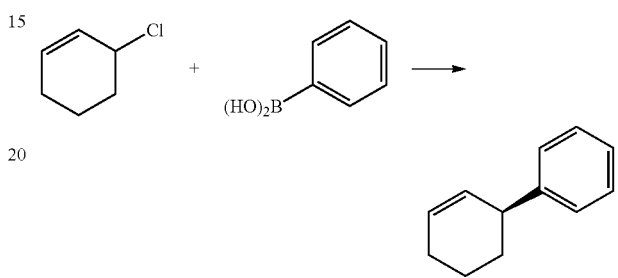

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and $Cs_2CO_3$ (130.3 mg, 0.40 mmol, 1.00 eq) were stirred in THF (2 mL) at 60° C. for 30 min. A solution of phenylboronic acid (97.5 mg, 0.80 mmol, 2.00 eq) and 3-chlorocyclohexene (45 µL, 0.40 mmol, 1.00 eq) in THF (1.5 mL) was then added via syringe and the flask rinsed with THF (0.5 mL). The resulting mixture was then stirred for 1 h at 60° C. before the addition of $SiO_2$ (20 mg). The solvent was then carefully evaporated and the solid directly loaded onto the top of a flash chromatography column. The column was eluted with pentane to obtain the pure product in 99% yield (62.0 mg, 0.39 mmol) as a colorless oil.

Enantiomeric excess of 99% was determined by HPLC [Chiralpak® ID; flow: 0.6 mL/min; hexane/i-PrOH: 99.9:0.1; λ=210 nm; major enantiomer $t_R$=8.3 min; minor enantiomer $t_R$=8.9 min].

$^1$H NMR (400 MHz, CDCl$_3$) $\delta_H$/ppm: 7.31 (m, 3H), 7.27-7.17 (m, 2H), 5.90 (dq, J=9.8, 3.4 Hz, 1H), 5.73 (dq, J=10.0, 2.4 Hz, 1H), 3.42 (m, 1H), 2.15-1.95 (m, 3H), 1.85-1.70 (m, 1H), 1.70-1.51 (m, 2H).

$^{13}$C NMR (100 MHz, CDCl$_3$) $\delta_C$/ppm: 146.8, 130.3, 128.5, 128.4 (2C), 127.9 (2C), 126.1, 42.0, 32.8, 25.2, 21.3.

HRMS (EI/FI) m/z calcd for $C_{12}H_{14}[M]^+$: 158.1094, found: 158.1096.

IR (ATR) v (cm$^{-1}$, CHCl$_3$): 1233, 1748, 2117, 2857, 2930, 3022.

$[\alpha]^{20}_{589}$=−134.6 (c 0.55 CHCl$_3$) for 99% ee [lit. $[\alpha]^{20}_{589}$=−121.9 (c 1.00 CHCl$_3$) for 96% ee]

Using 3-chlorocyclohexene, [Rh(cod)(OH)]$_2$ and (S)—Cl-MeO-BIPHEP

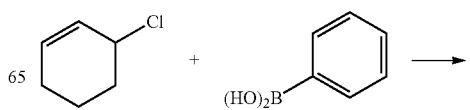

-continued

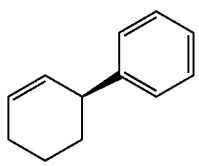

In a 10 mL round bottomed flask [Rh(cod)(OH)]$_2$ (4.6 mg, 0.01 mmol, 0.025 eq), (S)—Cl-MeO-BIPHEP 2 (15.6 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of benzeneboronic acid (97.5 mg, 0.80 mmol, 2.00 eq) and 3-chlorocyclohexene (45 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into a chromatographic column eluting with hexane to obtain the pure product in 99% yield (63.0 mg, 0.39 mmol) as a colorless oil.

Enantiomeric excess of 99% was determined by HPLC [Chiralpak® ID; flow: 0.6 mL/min; hexane/i-PrOH: 99.9: 0.1; λ=210 nm; major enantiomer $t_R$=7.7 min; minor enantiomer $t_R$=8.9 min].

Using 3-chlorocyclohexene, [Rh(cod)(OH)]$_2$ and (R)-Xyl-BINAP

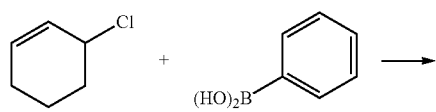

In a 10 mL round bottomed flask [Rh(cod)(OH)]$_2$ (4.6 mg, 0.01 mmol, 0.025 eq), (R)-Xyl-BINAP 3 (17.6 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of benzeneboronic acid (97.5 mg, 0.80 mmol, 2.00 eq) and 3-chlorocyclohexene (45 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into a chromatographic column eluting with hexane to obtain the pure product in 52% yield (33.0 mg, 0.21 mmol) as a colorless oil.

Enantiomeric excess of 96% was determined by HPLC [Chiralpak® ID; flow: 0.6 mL/min; hexane/i-PrOH: 99.9: 0.1; λ=210 nm; minor enantiomer $t_R$=7.7 min; minor enantiomer $t_R$=8.9 min].

Using 3-bromocyclohexene, [Rh(cod)(OH)]$_2$ and (S)-BINAP

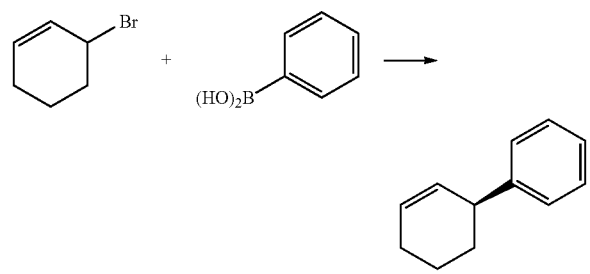

In a 10 mL round bottomed flask [Rh(cod)(OH)]$_2$ (4.6 mg, 0.01 mmol, 0.025 eq), (S)-BINAP 4 (14.9 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of benzeneboronic acid (97.5 mg, 0.80 mmol, 2.00 eq) and 3-bromocyclohexene (46 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into a chromatographic column eluting with hexane to obtain the pure product in 59% yield (37.2 mg, 0.24 mmol) as a colorless oil.

Enantiomeric excess of 98% was determined by HPLC [Chiralpak® ID; flow: 0.6 mL/min; hexane/i-PrOH: 99.9: 0.1; λ=210 nm; major enantiomer $t_R$=7.8 min; minor enantiomer $t_R$=8.8 min].

Using 3-bromocyclohexene, Rh(acac)(C$_2$H$_4$)$_2$ and (S)-BINAP

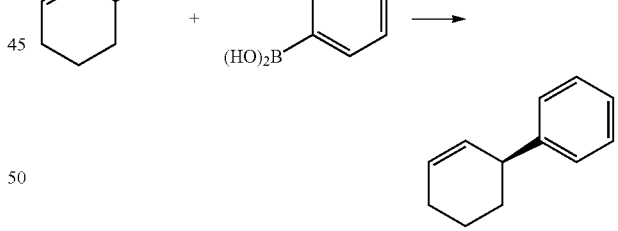

In a 10 mL round bottomed flask Rh(acac)(C$_2$H$_4$)$_2$ (5.2 mg, 0.02 mmol, 0.10 eq), (S)-BINAP 4 (14.9 mg, 0.024 mmol, 0.12 eq) and Cs$_2$CO$_3$ (130.3 mg, 0.20 mmol, 1.00 eq) were stirred in THF (1.0 mL) at 60° C. for 30 min. A solution of benzeneboronic acid (47.6 mg, 0.40 mmol, 2.00 eq) and 3-bromocyclohexene (23 µL, 0.40 mmol, 1.00 eq) in THF (0.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into a chromatographic column eluting with hexane to obtain the pure product in 72% yield (22.8 mg, 0.14 mmol) as a colorless oil.

Enantiomeric excess of 86% was determined by HPLC [Chiralpak® ID; flow: 0.6 mL/min; hexane/i-PrOH: 99.9:0.1; λ=210 nm; major enantiomer $t_R$=7.8 min; minor enantiomer $t_R$=8.8 min].

Using 3-bromocyclohexene, [Rh(cod)(OH)]$_2$ and (R)-MonoPHOS

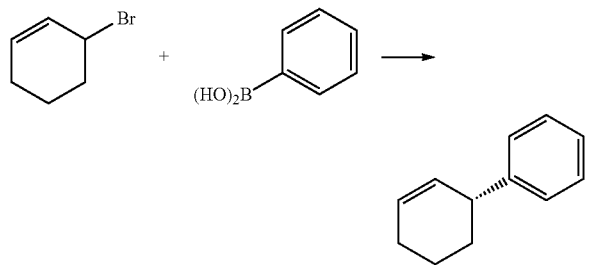

In a 10 mL round bottomed flask [Rh(cod)(OH)]$_2$ (4.6 mg, 0.01 mmol, 0.025 eq), (R)-MonoPHOS (18.0 mg, 0.05 mmol, 0.13 eq) and Cs$_2$CO$_3$ (130.3 mg, 0.40 mmol, 1.00 eq) were stirred in THF (2 mL) at 60° C. for 30 min. A solution of benzeneboronic acid (97.5 mg, 0.80 mmol, 2.00 eq) and 3-bromocyclohexene (46 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into a chromatographic column eluting with hexane to obtain the pure product in 61% yield (38.9 mg, 0.24 mmol) as a colorless oil.

Enantiomeric excess of 89% was determined by HPLC [Chiralpak® ID; flow: 0.6 mL/min; hexane/i-PrOH: 99.9:0.1; λ=210 nm; minor enantiomer $t_R$=7.7 min; major enantiomer $t_R$=8.3 min].

Using 3-bromocyclohexene, [Rh(cod)(OH)]$_2$ and (S)-SegPHOS

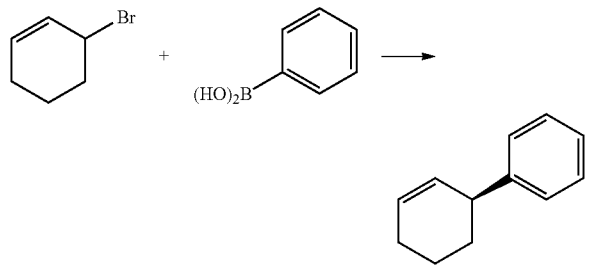

In a 10 mL round bottomed flask [Rh(cod)(OH)]$_2$ (4.6 mg, 0.01 mmol, 0.025 eq), (S)-SegPHOS (14.7 mg, 0.024 mmol, 0.13 eq) and Cs$_2$CO$_3$ (130.3 mg, 0.40 mmol, 1.00 eq) were stirred in THF (2 mL) at 60° C. for 30 min. A solution of benzeneboronic acid (97.5 mg, 0.80 mmol, 2.00 eq) and 3-bromocyclohexene (46 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into a chromatographic column eluting with hexane to obtain the pure product in 99% yield (63.0 mg, 0.40 mmol) as a colorless oil.

Enantiomeric excess of 98% was determined by HPLC [Chiralpak® ID; flow: 0.6 mL/min; hexane/i-PrOH: 99.9:0.1; λ=210 nm; major enantiomer $t_R$=7.6 min; minor enantiomer $t_R$=8.8 min].

$^1$H NMR (400 MHz, CDCl$_3$) $\delta_H$/ppm: 7.31 (m, 3H), 7.27-7.17 (m, 2H), 5.90 (dq, J=9.8, 3.4 Hz, 1H), 5.73 (dq, J=10.0, 2.4 Hz, 1H), 3.42 (m, 1H), 2.15-1.95 (m, 3H), 1.85-1.70 (m, 1H), 1.70-1.51 (m, 2H).

$^{13}$C NMR (100 MHz, CDCl$_3$) $\delta_C$/ppm: 146.8, 130.3, 128.5, 128.4 (2C), 127.9 (2C), 126.1, 42.0, 32.8, 25.2, 21.3.

HRMS (EI/FI) m/z calcd for C$_{12}$H$_{14}$[M]$^+$: 158.1094, found: 158.1096.

IR (ATR) ν (cm$^{-1}$, CHCl$_3$): 1233, 1748, 2117, 2857, 2930, 3022.

$[\alpha]^{20}_{589}$=−134.6 (c 0.55 CHCl$_3$) for 98% ee [lit. $[\alpha]^{20}_{589}$=−121.9 (c 1.00 CHCl$_3$) for 96% ee].

Example 2—Preparation of (−)-(S)-2-(Cyclohex-2-en-1-yl)naphthalene 3

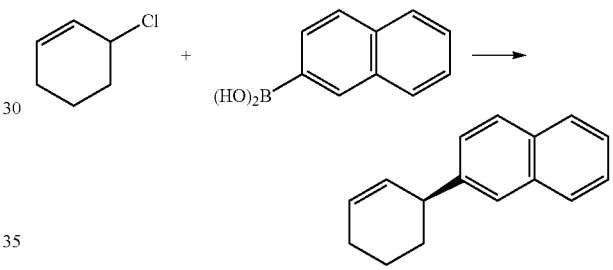

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 2-naphtaleneboronic acid (137.6 mg, 0.80 mmol, 2.00 eq) and 3-chlorocyclohexene (45 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain (−)-(S)-2-(cyclohex-2-en-1-yl)naphthalene in 96% yield (79.8 mg, 0.38 mmol) as a white solid.

Enantiomeric excess of 89% was determined by HPLC [Chiralpak® IA; flow: 0.6 mL/min; hexane 100; λ=210 nm; minor enantiomer $t_R$=10.8 min; major enantiomer $t_R$=11.4 min].

$^1$H NMR (400 MHz, CDCl$_3$) $\delta_H$/ppm: 7.81 (m, 3H), 7.67 (m, 1H), 7.57-7.35 (m, 3H), 5.98 (m, 1H), 5.84 (dq, J=10.1, 2.4 Hz, 1H), 3.60 (m, 1H), 2.27-1.99 (m, 3H), 1.80 (s, 1H), 1.68 (m, 2H).

$^{13}$C NMR (100 MHz, CDCl$_3$) δC/ppm: 144.1, 133.6, 132.2, 130.1, 128.7, 127.9, 127.6, 127.6, 126.8, 125.9, 125.8, 125.2, 42.0, 32.5, 25.1, 21.2.

HRMS (EI/FI) m/z calcd for C$_{16}$H$_{16}$[M]$^+$: 208.1252, found: 208.1254.

IR (ATR) ν (cm$^{-1}$, CHCl$_3$): 1235, 1748, 2120, 2860, 2935, 3017, 3052.

$[\alpha]^{20}_{589}$=−221.1 (c 0.91 CHCl$_3$) for 89% ee.

Example 3—Preparation of (−)-(S)-3-(3-Methylphenyl)cyclohexene 4

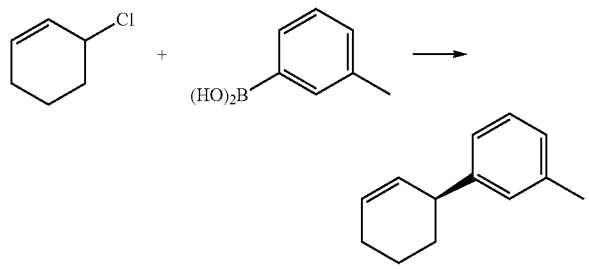

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 3-methylphenylboronic acid (108.8 mg, 0.80 mmol, 2.00 eq) and 3-chlorocyclohexene (45 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 96% yield (65.9 mg, 0.38 mmol) as a colorless oil.

Enantiomeric excess of 97% was determined by HPLC [Chiralpak® IB; flow: 0.5 mL/min; hexane 100; λ=210 nm; minor enantiomer t$_R$=9.1 min; major enantiomer t$_R$=9.4 min].

$^1$H NMR (400 MHz, CDCl$_3$) δ$_H$/ppm: 7.24-7.15 (m, 1H), 7.03 (d, J=7.7 Hz, 3H), 5.94-5.84 (m, 1H), 5.71 (dq, J=10.0, 2.4 Hz, 1H), 3.37 (m, 1H), 2.35 (s, 3H), 2.19-2.03 (m, 2H), 2.03-1.95 (m, 1H), 1.82-1.72 (m, 1H), 1.60 (m, 2H).

$^{13}$C NMR (100 MHz, CDCl$_3$) δ$_C$/ppm: 146.8, 138.0, 130.5, 128.6, 128.4, 128.3, 126.9, 124.9, 42.0, 32.8, 25.2, 21.6, 21.4.

HRMS (EI/FI) m/z calcd for C$_{13}$H$_{16}$ [M]$^+$: 172.1252, found: 172.1255.

IR (ATR) ν (cm$^{-1}$, CHCl$_3$): 1446, 1488, 1607, 2836, 2857, 2928, 3020.

[α]$^{20}_{589}$=−117.0 (c 0.96 CHCl$_3$) for 97% ee.

Example 4—Preparation of (−)-(S)-3-(4-Methylphenyl)cyclohexene 5

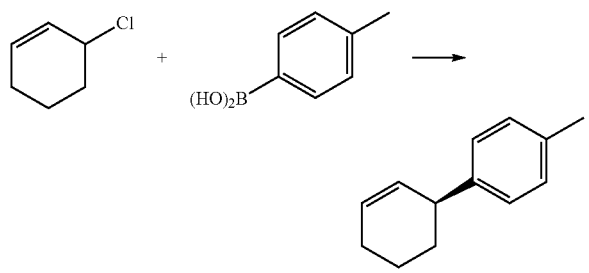

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 4-methylphenylboronic acid (108.8 mg, 0.80 mmol, 2.00 eq) and 3-chlorocyclohexene (45 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 58% yield (40.0 mg, 0.23 mmol) as a colorless oil.

Enantiomeric excess of >94% was determined by HPLC [Chiralpak® IC; flow: 0.7 mL/min; hexane 100; λ=210 nm; minor enantiomer t$_R$=6.4 min; major enantiomer t$_R$=6.8 min].

$^1$H NMR (400 MHz, CDCl$_3$) δ$_H$/ppm: 7.13 (s, 4H), 5.89 (dq, J=9.8, 2.5 Hz, 1H), 5.71 (dq, J=10.2, 2.5 Hz, 1H), 3.38 (m, 1H), 2.34 (s, 3H), 2.09 (s, 2H), 2.01 (m, 1H), 1.75 (m, 1H), 1.71-1.48 (m, 2H).

$^{13}$C NMR (100 MHz, CDCl$_3$) δ$_C$/ppm: 143.8, 135.6, 130.5, 129.1 (2C), 128.3, 127.8 (2C), 41.6, 32.8, 25.2, 21.4, 21.2.

HRMS (EI/FI) m/z calcd for C$_{13}$H$_{16}$[M]$^+$: 172.1252, found: 172.1254.

IR (ATR) ν (cm$^{-1}$, CHCl$_3$): 766, 1445, 1511, 2857, 2928, 3019.

[α]$^{20}_{589}$=−128.0 (c 0.47 CHCl$_3$) for >94% ee [lit. [α]$^{20}_{589}$=−129.3 (c 1.10 CHCl$_3$) for 94% ee].

Example 5—Preparation of (−)-(S)-3-(4-Methoxyphenyl)cyclohexene 6

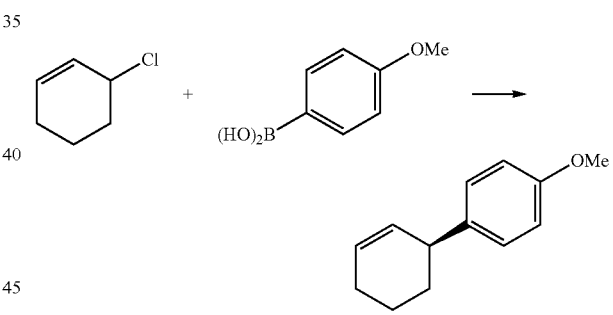

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 4-methoxyphenylboronic acid (121.6 mg, 0.80 mmol, 2.00 eq) and 3-chlorocyclohexene (45 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 77% yield (58.0 mg, 0.31 mmol) as a colorless oil.

Enantiomeric excess of 97% was determined by HPLC [Chiralpak® IB; flow: 0.6 mL/min; hexane 100; λ=210 nm; minor enantiomer t$_R$=8.8 min; major enantiomer t$_R$=8.3 min].

$^1$H NMR (400 MHz, CDCl$_3$) δ$_H$/ppm: 7.15 (dd, J=7.8, 1.4 Hz, 2H), 6.93-6.76 (m, 2H), 5.88 (dt, J=10.2, 3.2 Hz, 1H), 5.78-5.61 (m, 1H), 3.80 (s, 3H), 3.37 (m, 1H), 2.14-2.05 (m, 2H), 2.05-1.95 (m, 1H), 1.74 (m, 1H), 1.69-1.45 (m, 2H).

$^{13}$C NMR (100 MHz, CDCl$_3$) $\delta_C$/ppm: 158.0, 138.9, 130.6, 128.8 (2C), 128.3, 113.8 (2C), 55.4, 41.1, 32.9, 25.2, 21.3.

HRMS (EI/FI) m/z calcd for C$_{13}$H$_{16}$O [M]$^+$: 188.1201, found: 188.1204.

IR (ATR) ν (cm$^{-1}$, CHCl$_3$): 1243, 1444, 1509, 2834, 2929, 3019.

$[\alpha]^{20}_{589}$=−134.6 (c 1.40 CHCl$_3$) for 97% ee [lit. ent. $[\alpha]^{20}_{589}$=+145.8 (c 1.00 Benzene) for 99.9% ee]

Example 6—Preparation of (−)-(S)-3-(4-Trifluoromethylphenyl)cyclohexene 7

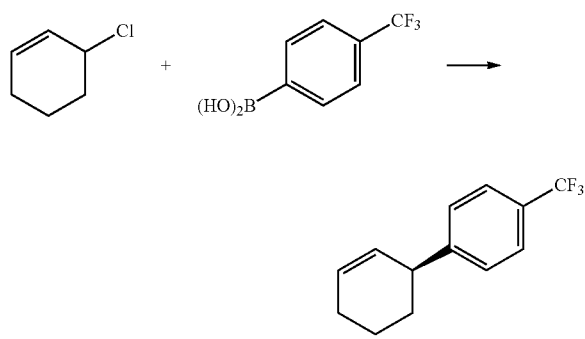

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 4-trifluoromethylphenylboronic acid (151.9 mg, 0.80 mmol, 2.00 eq) and 3-chlorocyclohexene (45 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 60% yield (54.0 mg, 0.24 mmol) as a colorless oil.

Enantiomeric excess of 96% was determined by HPLC [Chiralpak® IA; flow: 0.6 mL/min; hexane 100; λ=210 nm; minor enantiomer t$_R$=6.2 min; major enantiomer t$_R$=6.5 min].

$^1$H NMR (400 MHz, CDCl$_3$) $\delta_H$/ppm: 7.55 (d, J=8.0 Hz, 2H), 7.33 (d, J=8.0 Hz, 2H), 5.94 (dq, J=9.9, 2.3 Hz, 1H), 5.68 (dq, J=9.9, 2.3 Hz, 1H), 3.47 (m, 1H), 2.16-1.91 (m, 3H), 1.81-1.66 (m, 1H), 1.67-1.59 (m, 1H), 1.59-1.41 (m, 1H).

$^{13}$C NMR (100 MHz, CDCl$_3$) $\delta_C$/ppm: 150.9, 129.3, 129.2, 128.2 (2C), 125.4, 125.4, 125.3, 125.2 (q, J=3.8 Hz, 1C), 41.8, 32.6, 25.1, 21.1.

HRMS (EI/FI) m/z calcd for C$_{13}$H$_{13}$F$_3$[M]$^+$: 226.0969, found: 226.0970.

IR (ATR) ν (cm$^{-1}$, CHCl$_3$): 1122, 1324, 1619, 2834, 2932, 3019.

$[\alpha]^{20}_{589}$=−98.9 (c 1.60 CHCl$_3$) for 96% ee.

Example 7—Preparation of (−)-(S)-3-(3-Methoxycarbonylphenyl)cyclohexene 8

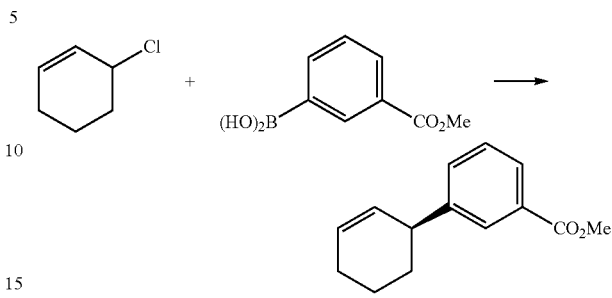

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 3-methoxycarbonylphenylboronic acid (144.0 mg, 0.80 mmol, 2.00 eq) and 3-chlorocyclohexene (45 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with hexane: EtOAc (92:8) to obtain the pure product in 86% yield (74.0 mg, 0.34 mmol) as a colorless oil.

Enantiomeric excess of 99.9% was determined by HPLC [Chiralpak® ID; flow: 1.0 mL/min; hexane:IPA 99:1 100; λ=210 nm; major enantiomer t$_R$=5.6 min; minor enantiomer t$_R$=6.1 min].

$^1$H NMR (400 MHz, CDCl$_3$) $\delta_H$/ppm: 7.93-7.84 (m, 2H), 7.47-7.32 (m, 2H), 5.98-5.88 (m, 1H), 5.70 (m, 1H), 3.91 (s, 3H), 3.46 (m, 1H), 2.10 (m, 2H), 2.06-1.97 (m, 1H), 1.81-1.48 (m, 3H).

$^{13}$C NMR (101 MHz, CDCl$_3$) $\delta_C$/ppm: 167.5, 147.2, 132.6, 130.3, 129.6, 129.1, 129.0, 128.4, 127.4, 5.20, 41.8, 32.7, 25.1, 21.2.

HRMS (EI/FI) m/z calcd for C$_{14}$H$_{16}$O$_2$[M]$^+$: 216.1150, found: 216.1148.

IR (ATR) ν (cm$^{-1}$, CHCl$_3$): 3020, 2930, 2857, 1721.

$[\alpha]^{20}_{589}$=−101.0 (c 1.12 CHCl$_3$) for 99.9% ee.

Example 8—Preparation of (−)-(S)-3-(4-Fluorophenyl)cyclohexene 9

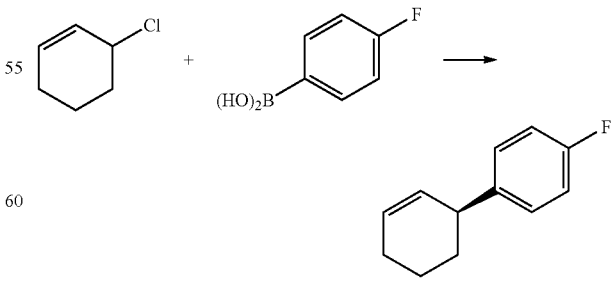

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq)

were stirred in THF (2 mL) at 60° C. for 30 min. A solution of 4-fluorophenylboronic acid (111.9 mg, 0.80 mmol, 2.00 eq) and 3-chlorocyclohexene (45 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 54% yield (38.4 mg, 0.22 mmol) as a colorless oil.

Enantiomeric excess of 99.5% was determined by HPLC [Chiralpak® ID; flow: 0.4 mL/min; hexane 100; λ=210 nm; minor enantiomer $t_R$=11.4 min; major enantiomer $t_R$=11.8 min].

$^1$H NMR (500 MHz, CDCl$_3$) δ$_H$/ppm: 7.17 (dd, J=8.3, 5.5 Hz, 2H), 6.98 (t, J=8.5 Hz, 2H), 5.89 (dq, J=9.9, 3.4 Hz, 1H), 5.68 (dd, J=10.1, 2.5 Hz, 1H), 3.39 (m, 1H), 2.08 (m, 2H), 2.00 (m, 1H), 1.79-1.44 (m, 3H).

$^{13}$C NMR (126 MHz, CDCl$_3$) δ$_C$/ppm: 161.3 (d, J=243.3 Hz, 1C), 142.4 (d, J=3.2 Hz, 1C), 130.1, 129.2 (d, J=7.8 Hz, 2C), 128.7, 115.0 (d, J=21.0 Hz, 2C), 41.2, 32.9, 25.1, 21.2.

HRMS (EI/FI) m/z calcd for C$_{12}$H$_{13}$F [M]$^+$: 176.1001, found: 176.1003.

IR (ATR) ν (cm$^{-1}$, CHCl$_3$): 1220, 1507, 1601, 2856, 2930, 3020.

$[α]^{20}_{589}$=–112.4 (c 1.09 CHCl$_3$) for 99.5% ee.

Example 9—Preparation of (–)-(S)-3-(4-Chlorophenyl)cyclohexene 10

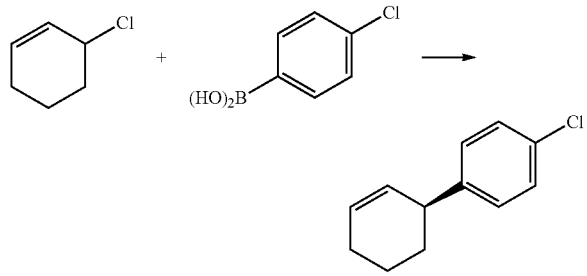

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 4-chlorophenylboronic acid (111.9 mg, 0.80 mmol, 2.00 eq) and 3-chlorocyclohexene (45 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 81% yield (62.7 mg, 0.32 mmol) as a colorless oil.

Enantiomeric excess of 99.8% was determined by HPLC [Chiralpak® ID; flow: 1.0 mL/min; hexane 100; λ=210 nm; minor enantiomer $t_R$=4.7 min; major enantiomer $t_R$=5.4 min].

$^1$H NMR (400 MHz, CDCl$_3$) δ$_H$/ppm: 7.23-7.14 (m, 2H), 7.14-7.04 (m, 2H), 5.83 (dq, J=9.9, 2.3 Hz, 1H), 5.59 (dq, J=10.0, 2.3 Hz, 1H), 3.30 (m, 1H), 2.01 (m, J=3.5, 1.7 Hz, 2H), 1.97-1.87 (m, 1H), 1.64 (m, 1H), 1.59-1.50 (m, 1H), 1.43 (m, 1H).

$^{13}$C NMR (100 MHz, CDCl$_3$) δ$_C$/ppm: 145.3, 131.8, 129.8, 129.3 (2C), 129.0, 128.6 (2C), 41.4, 32.8, 25.2, 21.2.

HRMS (EI/FI) m/z calcd for C$_{12}$H$_{13}$Cl [M]$^+$: 192.0706, found: 192.0708.

IR (ATR) ν (cm$^{-1}$, CHCl$_3$): 1091, 1489, 2836, 2858, 2930, 3020.

$[α]^{20}_{589}$=–139.0 (c 1.45 CHCl$_3$) for 99.8% ee.

Example 10—Preparation of (–)-(S)-3-(3-Chlorophenyl)cyclohexene 11

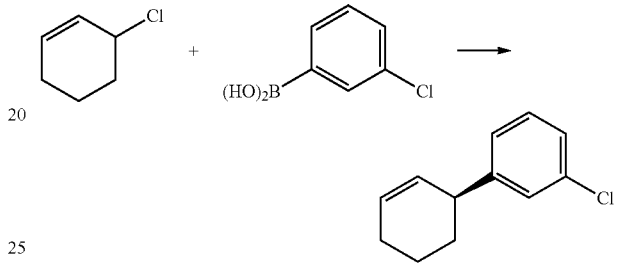

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 3-chlorophenylboronic acid (125.1 mg, 0.80 mmol, 2.00 eq) and 3-chlorocyclohexene (45 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 70% yield (54.0 mg, 0.28 mmol) as a colorless oil.

Enantiomeric excess of 99% was determined by HPLC [Chiralpak® ID; flow: 1.0 mL/min; hexane 100; λ=210 nm; major enantiomer $t_R$=4.9 min; minor enantiomer $t_R$=6.6 min].

$^1$H NMR (400 MHz, CDCl$_3$) δ$_H$/ppm: 7.25-7.14 (m, 3H), 7.10 (dt, J=7.2, 1.6 Hz, 1H), 5.92 (dq, J=9.8, 2.3 Hz, 1H), 5.76-5.54 (m, 1H), 3.38 (m, 1H), 2.18-1.94 (m, 3H), 1.73 (m, 1H), 1.68-1.45 (m, 2H).

$^{13}$C NMR (100 MHz, CDCl$_3$) δ$_C$/ppm: 148.9, 134.2, 129.6, 129.4, 129.2, 128.0, 126.3, 126.1, 41.7, 32.6, 25.1, 21.1.

HRMS (EI/FI) m/z calcd for C$_{12}$H$_{13}$Cl [M]$^+$: 192.0706, found: 192.0708.

IR (ATR) ν (cm$^{-1}$, CHCl$_3$): 1096, 1475, 1650, 2836, 2857, 2930, 3020, 3059.

$[α]^{20}_{589}$=–132.2 (c 1.18 CHCl$_3$) for 99% ee.

Example 11—Preparation of (–)-(S)-3-(3-Bromophenyl)cyclohexene 12

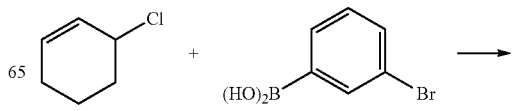

-continued

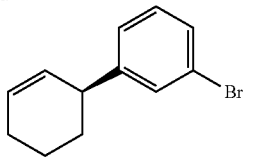

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 3-bromophenylboronic acid (125.1 mg, 0.80 mmol, 2.00 eq) and 3-chlorocyclohexene (45 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into a chromatographic column eluting with hexane to obtain the pure product in 56% yield (53.0 mg, 0.22 mmol) as a colorless oil.

Enantiomeric excess of 96% was determined by HPLC [Chiralpak® ID; flow: 1.0 mL/min; hexane 100; λ=210 nm; major enantiomer $t_R$=5.1 min; minor enantiomer $t_R$=7.6 min].

$^1$H NMR (400 MHz, CDCl$_3$) δ$_H$/ppm: 7.25-7.15 (m, 3H), 7.10 (dt, J=7.2, 1.6 Hz, 1H), 5.92 (dq, J=9.8, 2.3 Hz, 1H), 5.76-5.59 (m, 1H), 3.38 (m, 1H), 2.20-1.94 (m, 3H), 1.73 (m, 1H), 1.69-1.45 (m, 2H).

$^{13}$C NMR (100 MHz, CDCl$_3$) δ$_C$/ppm: 149.2, 131.0, 130.0, 129.4, 129.2 (2C), 126.6, 122.5, 41.7, 32.6, 25.1, 21.1.

HRMS (EI/FI) m/z calcd for C$_{12}$H$_{13}$Br [M]$^+$: 236.0208, found: 236.0203.

IR (ATR) ν (cm$^{-1}$, CHCl$_3$): 1096, 1477, 1651, 2835, 2857, 2930, 3020, 3057.

[α]$^{20}_{589}$=−104.5 (c 1.17 CHCl$_3$) for 96% ee.

Example 12—Preparation of (−)-(S)-Cyclopent-2-enylbenzene 13

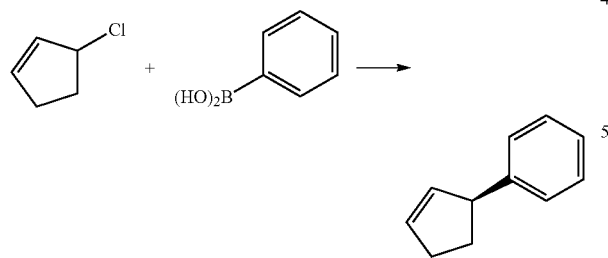

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of phenylboronic acid (97.5 mg, 0.80 mmol, 2.00 eq) and 3-chlorocyclopentene (52 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 24% yield (16.8 mg, 0.11 mmol) as a colorless oil.

Enantiomeric excess of 80% was determined by HPLC [Chiralpak® ID; flow: 0.6 mL/min; hexane 100; λ=210 nm; major enantiomer $t_R$=8.0 min; minor enantiomer $t_R$=8.5 min].

$^1$H NMR (400 MHz, CDCl$_3$) δ$_H$/ppm: 7.36-7.24 (m, 3H), 7.24-7.12 (m, 2H), 5.94 (m, 1H), 5.79 (m, 1H), 4.02-3.79 (m, 1H), 2.61-2.28 (m, 3H), 1.81-1.65 (m, 1H).

$^{13}$C NMR (101 MHz, CDCl$_3$) δ$_C$/ppm: 146.7, 134.4, 132.1, 128.5 (2C), 127.4 (2C), 126.1, 51.5, 34.0, 32.7.

HRMS (EI/FI) m/z calcd for C$_{11}$H$_{12}$[M]$^+$: 144.0939, found: 144.0932.

IR (ATR) ν (cm$^{-1}$, CHCl$_3$): 1376, 1735, 2856, 2926.

[α]$^{20}_{589}$=−35.0 (c 1.0 CHCl$_3$) for 80% ee.

Example 13—Preparation of (−)-(S)-Cyclohept-2-enylbenzene 14

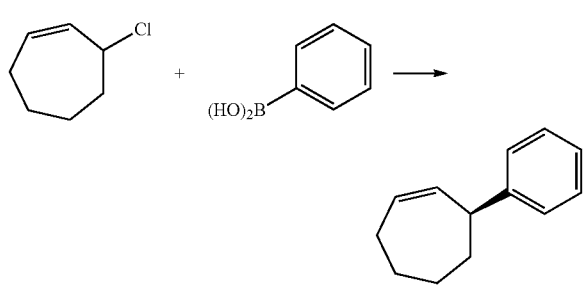

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of phenylboronic acid (97.5 mg, 0.80 mmol, 2.00 eq) and 3-chlorocycloheptene (52 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 48% yield (33.0 mg, 0.19 mmol) as a colorless oil.

Enantiomeric excess of 80% was determined by HPLC [Chiralpak® ID; flow: 0.6 mL/min; hexane 100; λ=210 nm; major enantiomer $t_R$=8.6 min; minor enantiomer $t_R$=9.3 min].

$^1$H NMR (400 MHz, CDCl$_3$) δ$_H$/ppm: 7.38-7.14 (m, 5H), 5.88 (m, 1H), 5.79 (m, 1H), 3.55 (m, 1H), 2.36-2.18 (m, 2H), 1.97 (m, 1H), 1.90-1.62 (m, 4H), 1.48 (m, 1H).

$^{13}$C NMR (101 MHz, CDCl$_3$) δ$_C$/ppm: 148.1, 137.2, 131.8, 128.6 (2C), 127.4 (2C), 125.9, 47.3, 36.4, 30.4, 29.0, 27.2.

HRMS (EI/FI) m/z calcd for C$_{13}$H$_{16}$ [M]$^+$: 172.1252, found: 172.1253.

IR (ATR) ν (cm$^{-1}$, CHCl$_3$): 1445, 1492, 2852, 2920, 3024.

[α]$^{20}_{589}$=−26.7 (c 0.82 CHCl$_3$) for 80% ee.

Example 14—Preparation of (−)-(S)-3-(2-Methylphenyl)cyclohexene 15

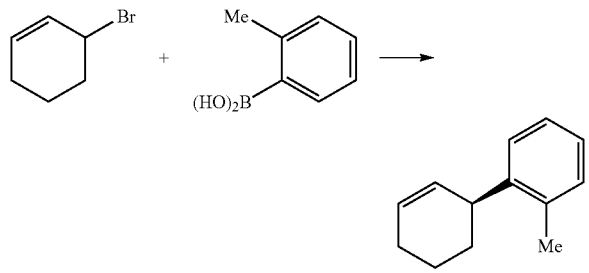

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 2-methylphenylboronic acid (108.8 mg, 0.80 mmol, 2.00 eq) and 3-bromocyclohexene (46 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 45% yield (30.3 mg, 0.18 mmol) as a colorless oil.

Enantiomeric excess of 99.1% was determined by HPLC [Chiralpak® ID; flow: 0.7 mL/min; hexane 100; λ=210 nm; minor enantiomer t$_R$=6.1 min; major enantiomer t$_R$=6.5 min].

$^1$H NMR (400 MHz, CDCl$_3$) δ$_H$/ppm: 7.26-7.00 (m, 4H), 5.93 (dq, J=9.9, 2.4 Hz, 1H), 5.68 (dd, J=10.1, 2.5 Hz, 1H), 3.63 (m, 1H), 2.36 (s, 3H), 2.16-2.05 (m, 2H), 2.05-1.94 (m, 1H), 1.75 (m, 1H), 1.69-1.58 (m, 1H), 1.48 (m, 1H).

$^{13}$C NMR (100 MHz, CDCl$_3$) δ$_C$/ppm: 144.5, 135.6, 130.6, 130.4, 128.5, 127.7, 126.1, 126.0, 37.9, 30.7, 25.2, 21.3, 19.4.

HRMS (ESI) m/z calcd for C$_{13}$H$_{16}$ [M]$^+$: 172.1252, found: 172.1255.

IR (ATR) ν (cm$^{-1}$, CHCl$_3$): 1487, 2856, 2929, 3019, 3061.

[α]$^{20}_{589}$=−47.5 (c 0.97 CHCl$_3$) for 99.1% ee.

Example 15—Preparation of (−)-(S)-3-(3-Nitrophenyl)cyclohexene 16

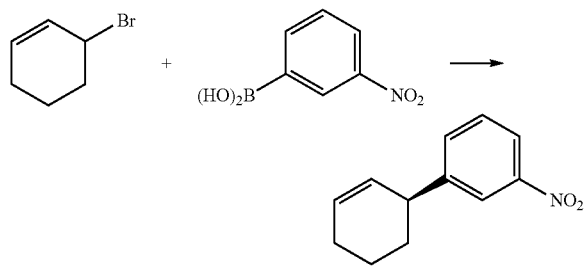

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 3-nitrophenylboronic acid (125.1 mg, 0.80 mmol, 2.00 eq) and 3-bromocyclohexene (46 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with hexane:EtOAc (92:8) to obtain the pure product in 51% yield (41.4 mg, 0.20 mmol) as a colorless oil.

Enantiomeric excess of 96% was determined by HPLC [Chiralpak® ID; flow: 1.0 mL/min; hexane:IPA 99:1 100; λ=210 nm; major enantiomer t$_R$=5.5 min; minor enantiomer t$_R$=5.8 min].

$^1$H NMR (400 MHz, CDCl$_3$) δ$_H$/ppm: 8.11-7.99 (m, 2H), 7.55 (m, 1H), 7.45 (m, 1H), 5.98 (dq, J=9.9, 2.3 Hz, 1H), 5.68 (dq, J=10.1, 2.4 Hz, 1H), 3.52 (m, 1H), 2.16-2.00 (m, 3H), 1.79-1.47 (m, 3H).

$^{13}$C NMR (100 MHz, CDCl$_3$) δ$_C$/ppm: 148.8, 148.5, 134.3, 130.1, 129.3, 128.6, 122.8, 121.3, 41.6, 32.6, 25.0, 20.9.

HRMS (EI/FI) m/z calcd for C$_{12}$H$_{13}$NO$_2$ [M]$^+$: 203.0946, found: 203.0947.

IR (ATR) ν (cm$^{-1}$, CHCl$_3$): 1350, 1529, 2930, 3054.

[α]$^{20}_{589}$=−78.1 (c 0.24 CHCl$_3$) for 96% ee.

Example 16—Preparation of (−)-(S)-3-(2-Methoxyphenyl)cyclohexene 17

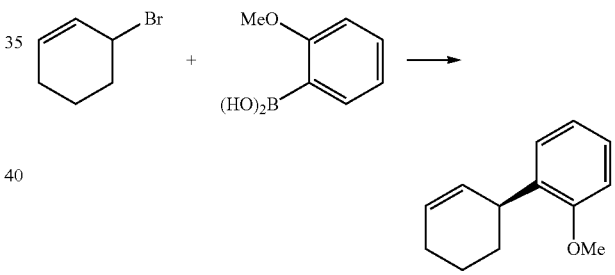

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 2-methoxyphenylboronic acid (150.6 mg, 0.80 mmol, 2.00 eq) and 3-bromocyclohexene (46 µL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane to obtain the pure product in 80% yield (60.2 mg, 0.32 mmol) as a colorless oil.

Enantiomeric excess of 74% was determined by HPLC [Chiralpak® IB; flow: 1.0 mL/min; hexane 100; λ=210 nm; minor enantiomer t$_R$=6.2 min; major enantiomer t$_R$=6.9 min].

$^1$H NMR (400 MHz, CDCl$_3$) δ$_H$/ppm: 7.25-7.02 (m, 4H), 5.93 (dq, J=9.9, 2.4 Hz, 1H), 5.68 (dd, J=10.1, 2.5 Hz, 1H), 3.63 (m, 1H), 2.36 (s, 3H), 2.19-2.07 (m, 2H), 2.07-1.90 (m, 1H), 1.75 (m, 1H), 1.70-1.57 (m, 1H), 1.48 (m, 1H).

$^{13}$C NMR (100 MHz, CDCl$_3$) δ$_C$/ppm: 144.4, 135.6, 130.6, 130.4, 128.5, 127.7, 126.1, 126.0, 37.9, 30.7, 25.2, 21.3, 19.4.

HRMS (EI/FI) m/z calcd for C$_{13}$H$_{16}$O [M]$^+$: 188.1201, found: 188.1204.

IR (ATR) ν (cm$^{-1}$, CHCl$_3$): 1238, 1490, 2857, 2929, 3019.

[α]$^{20}_{589}$=−41.2 (c 1.88 CHCl$_3$) for 74% ee.

Example 17—Preparation of (−)-(S)-3-(2,4-Difluorophenyl)cyclohexene 18

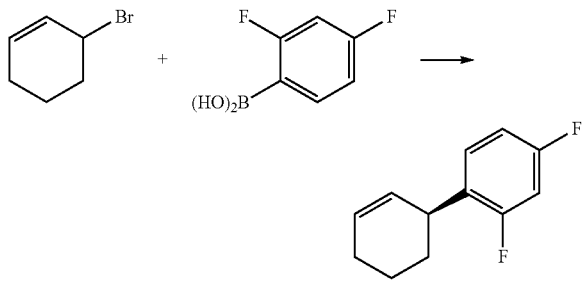

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 2,4-difluorophenylboronic acid (126.3 mg, 0.80 mmol, 2.00 eq) and 3-bromocyclohexene (46 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into onto the top of a flash chromatography column. The column was eluted with pentane to obtain the pure product in 53% yield (41.2 mg, 0.21 mmol) as a colorless oil.

Enantiomeric excess of 92% was determined by HPLC [Chiralpak® ID; flow: 0.7 mL/min; hexane 100; λ=210 nm; major enantiomer t$_R$=6.4 min; minor enantiomer t$_R$=6.8 min].

$^1$H NMR (500 MHz, CDCl$_3$) δ$_H$/ppm: 7.18 (m, 1H), 6.89-6.72 (m, 2H), 5.94 (dq, J=9.9, 3.4 Hz, 1H), 5.61 (dq, J=10.1, 2.5 Hz, 1H), 3.71 (m, 1H), 2.15-1.91 (m, 3H), 1.77-1.45 (m, 3H).

$^{13}$C NMR (126 MHz, CDCl$_3$) δ$_C$/ppm: 161.3 (dd, J=246.1, 12.2 Hz), 160.5 (dd, J=247.8, 11.7 Hz), 129.9 (dd, J=9.4, 6.5 Hz), 129.4, 128.83 (dd, J=14.8, 3.8 Hz), 128.6, 110.7 (dd, J=20.6, 3.7 Hz), 103.5 (dd, J=26.0, 25.3 Hz), 33.7 (d, J=2.3 Hz), 30.6, 24.9, 20.7.

HRMS (EI/FI) m/z calcd for C$_{12}$H$_{12}$F$_2$[M]$^+$: 194.0907, found: 194.0909.

IR (ATR) ν (cm$^{-1}$, CHCl$_3$): 1500, 2861, 2930, 3022.

[α]$^{20}_{589}$=−73.5 (c 0.89 CHCl$_3$) for 92% ee.

Example 18—Preparation of (−)-(S)-3-(4-Benzyloxyphenyl)cyclohexene 19

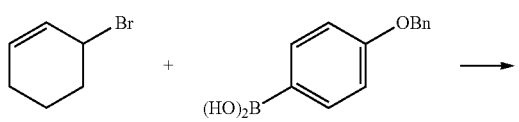

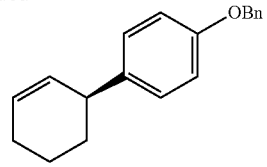

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 4-benzyloxyphenylboronic acid (182.4 mg, 0.80 mmol, 2.00 eq) and 3-bromocyclohexene (46 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded onto the top of a flash chromatography column. The column was eluted with pentane 100% to obtain the pure product in 61% yield (64.8 mg, 0.24 mmol) as a colorless oil.

Enantiomeric excess of 84% was determined by HPLC [Chiralpak® ID; flow: 1.0 mL/min; hexane:IPA 99:1 100; λ=210 nm; minor enantiomer t$_R$=4.4 min; major enantiomer t$_R$=5.0 min].

$^1$H NMR (400 MHz, CDCl$_3$) δ$_H$/ppm: 7.50-7.40 (m, 4H), 7.30 (s, 1H), 7.19 (s, 2H), 6.96 (d, J=8.7 Hz, 2H), 5.95-5.86 (m, 1H), 5.73 (m, 1H), 5.08 (s, 2H), 3.39 (m, 1H), 2.15-2.07 (m, 2H), 2.07-1.99 (m, 1H), 1.76 (m, 1H), 1.70-1.52 (m, 2H).

$^{13}$C NMR (101 MHz, CDCl$_3$) δ$_C$/ppm: 157.3, 139.2, 137.4, 130.6, 128.8 (2C), 128.7 (2C), 128.3, 128.0, 127.6 (2C), 114.7 (2C), 70.2, 41.1, 32.9, 25.2, 21.3.

HRMS (EI/FI) m/z calcd for C$_{19}$H$_{20}$O [M]$^+$: 264.1514, found: 264.1518.

IR (ATR) ν (cm$^{-1}$, CHCl$_3$): 3020, 2929, 2857, 1509, 1238.

[α]$^{20}_{589}$=−103.1 (c 1.96 CHCl$_3$) for 82% ee.

Example 19—Preparation of (−)-(S)-3-(4-tert-Butyldimethylsilyloxyphenyl)cyclohexene 20

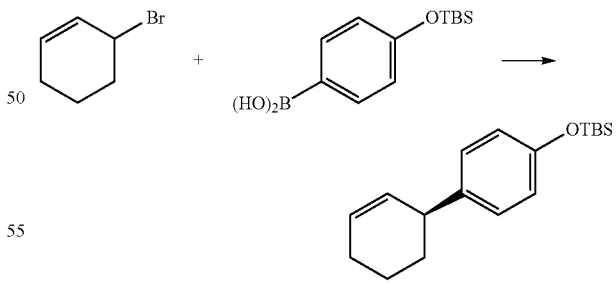

In a 10 mL round bottomed flask [Rh(cod)(OH)]$_2$ (4.6 mg, 0.01 mmol, 0.025 eq), (S)-Xyl-P—PHOS A (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of 4-tert-butyldimethylsilyloxyphenylboronic acid (201.8 mg, 0.80 mmol, 2.00 eq) and 3-bromocyclohexene (46 μL, 0.40 mmol, 1.00 eq) in THF (1.5 mL) was then added via syringe and the flask rinsed with THF (0.5 mL). The resulting mixture was then stirred for 1 h at 60° C. before the addition of SiO₂ (20 mg). The solvent was then carefully evaporated and the solid directly loaded onto the top of a flash chromatography column. The column was eluted with pentane 100% to obtain the pure product in 40% yield (46.2 mg, 0.16 mmol) as a colorless oil.

Enantiomeric excess of 99% was determined by HPLC [Chiralpak® ID; flow: 1.0 mL/min; hexane:IPA 99.9:0.1 100; λ=210 nm; minor enantiomer $t_R$=4.6 min; major enantiomer $t_R$=5.1 min].

¹H NMR (400 MHz, CDCl₃) $\delta_H$/ppm: 7.05 (d, J=8.4 Hz, 2H), 6.76 (d, J=8.5 Hz, 2H), 5.90-5.81 (m, 1H), 5.69 (m, 1H), 3.33 (m, 1H), 2.06 (m, 2H), 2.02-1.92 (m, 1H), 1.72 (m, 1H), 1.64-1.45 (m, 2H), 0.98 (s, 9H), 0.19 (s, 6H).

¹³C NMR (101 MHz, CDCl₃) $\delta_C$/ppm: 153.9, 139.4, 130.8, 128.7 (2C), 128.2, 119.8 (2C), 41.2, 32.9, 25.9 (3C), 25.2, 21.3, 18.3, −4.3 (2C).

HRMS (EI/FI) m/z calcd for C₁₈H₂₈OSi [M]⁺: 288.1909, found: 288.1909.

IR (ATR) ν (cm⁻¹, CHCl₃): 2955, 2930, 2858, 1509, 1256.

[α]²⁰₅₈₉=−17.6 (c 1.54 CHCl₃) for 99% ee.

Example 20—Preparation of (−)-(S)-3-Phenyl-3,6-dihydro-2H-pyran 21

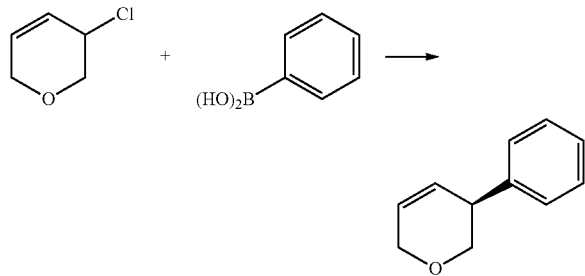

In a 10 mL round bottomed flask [Rh(cod)(OH)]₂ (6.8 mg, 0.015 mmol, 0.025 eq), (S)-Xyl-P—PHOS A (27.2 mg, 0.036 mmol, 0.06 eq) and Cs₂CO₃ (195.5 mg, 0.60 mmol, 1.00 eq) were stirred in THF (3 mL) at 60° C. for 30 min. A solution of phenylboronic acid (146.3 mg, 1.20 mmol, 2.00 eq) and 3-chloro-3,6-dihydro-2H-pyran (71.1 mg, 0.60 mmol, 1.00 eq) in THF (2.0 mL) was then added via syringe and the flask rinsed with THF (1.0 mL). The resulting mixture was then stirred for 3 h at 60° C. before the addition of NaOH 2M (0.2 mL). The aqueous phase was extracted with Et₂O (2×0.2 mL). The combined organic extracts were washed with water (0.4 mL), dried with MgSO₄, and filtered before adding SiO₂ (20 mg) and carefully concentrated under vacuum. The resulting solid was directly loaded into a column containing silica gel, and flash column chromatography (eluting with pentane:Et₂O (95:5)) was used to obtain the pure product in 99% yield (92.0 mg, 0.59 mmol) as a colorless oil.

Enantiomeric excess of 96% was determined by HPLC [Chiralpak® ID; flow: 0.8 mL/min; hexane:iPA 98:2; λ=210 nm; major enantiomer $t_R$=7.1 min; minor enantiomer $t_R$=7.5 min].

¹H NMR (400 MHz, CDCl₃) $\delta_H$/ppm: 7.38-7.28 (m, 2H), 7.27-7.20 (m, 3H), 5.94 (m, 2H), 4.23 (d, J=2.1 Hz, 2H), 4.10-3.99 (m, 1H), 3.62-3.50 (m, 2H).

¹³C NMR (101 MHz, CDCl₃) $\delta_C$/ppm: 141.9, 128.6 (2C), 128.2 (2C), 128.0, 127.1, 126.9, 71.3, 65.5, 41.5.

HRMS (EI/FI) m/z calcd for C₁₁H₁₂O [M]⁺: 160.0888, found: 160.0884.

IR (ATR) ν (cm⁻¹, CHCl₃): 1453, 1492, 2845, 2956, 3061.

[α]²⁰₅₈₉=−115.3 (c 0.76 CHCl₃) for 96% ee.

Example 21—Preparation of (−)-(S)-3-(Naphthalen-2-yl)-3,6-dihydro-2H-pyran 22

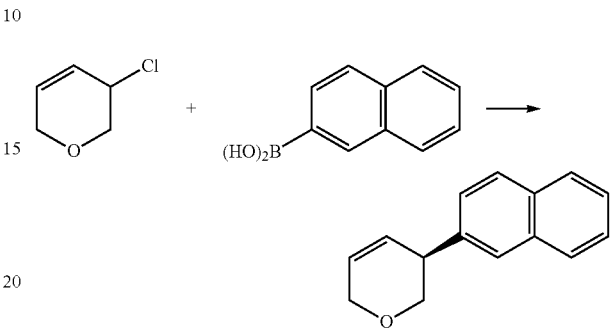

In a 10 mL round bottomed flask [Rh(cod)(OH)]₂ (5.7 mg, 0.013 mmol, 0.025 eq), (S)-Xyl-P—PHOS A (22.7 mg, 0.03 mmol, 0.06 eq) and Cs₂CO₃ (162.9 mg, 0.50 mmol, 1.00 eq) were stirred in THF (3 mL) at 60° C. for 30 min. A solution of 2-naphthylboronic acid (172.0 mg, 1.00 mmol, 2.00 eq) and 3-chloro-3,6-dihydro-2H-pyran (59.3 mg, 0.50 mmol, 1.00 eq) in THF (1.5 mL) was then added via syringe and the flask rinsed with THF (1.0 mL). The resulting mixture was then stirred for 3 h at 60° C. before the addition of NaOH 2M (0.2 mL). The aqueous phase was extracted with Et₂O (2×0.2 mL). The combined organic extracts were washed with water (0.4 mL), dried with MgSO₄, and filtered before adding SiO₂ (20 mg) and carefully evaporated. The resulting solid was directly loaded onto the top of a flash chromatography column, and eluting with pentane: Et₂O (95:5) to obtain the pure product in 90% yield (93.9 mg, 0.45 mmol) as a colorless oil.

Enantiomeric excess of 98% was determined by HPLC [Chiralpak® IB; flow: 1.0 mL/min; hexane:iPA 98:2; λ=210 nm; minor enantiomer $t_R$=6.2 min; major enantiomer $t_R$=6.6 min].

¹H NMR (400 MHz, CDCl₃) $\delta_H$/ppm: 7.89-7.79 (m, 3H), 7.72 (d, J=1.7 Hz, 1H), 7.54-7.38 (m, 3H), 6.03 (m, 2H), 4.30 (m, 2H), 4.15 (dd, J=10.0, 4.0 Hz, 1H), 3.78-3.65 (m, 2H).

¹³C NMR (101 MHz, CDCl₃) $\delta_C$/ppm: 139.4, 133.6, 132.6, 128.3, 128.0, 127.8, 127.7, 127.3, 126.6, 126.6, 126.2, 125.7, 71.2, 65.6, 41.6.

HRMS (EI/FI) m/z calcd for C₁₅H₁₄O [M]⁺: 210.1045, found: 210.1051.

IR (ATR) ν (cm⁻¹, CHCl₃): 1456, 1507, 2846, 2929, 3052.

[α]²⁰₅₈₉=−171.4 (c 0.83 CHCl₃) for 98% ee.

Example 22—Preparation of (−)-(S)-3-(m-Tolyl)-3,6-dihydro-2H-pyran 23

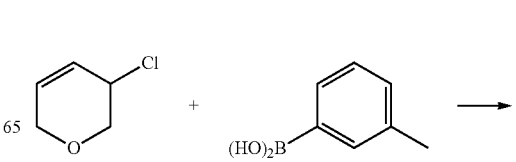

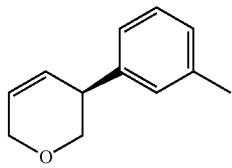

In a 10 mL round bottomed flask [Rh(cod)(OH)]$_2$ (5.7 mg, 0.013 mmol, 0.025 eq), (S)-Xyl-P—PHOS A (22.7 mg, 0.03 mmol, 0.06 eq) and Cs$_2$CO$_3$ (162.9 mg, 0.50 mmol, 1.00 eq) were stirred in THF (2.5 mL) at 60° C. for 30 min. A solution of m-tolylboronic acid (136.0 mg, 1.00 mmol, 2.00 eq) and 3-chloro-3,6-dihydro-2H-pyran (59.3 mg, 0.50 mmol, 1.00 eq) in THF (1.5 mL) was then added via syringe and the flask rinsed with THF (1.0 mL). The resulting mixture was then stirred for 3 h at 60° C. before the addition of NaOH 2M (0.2 mL). The aqueous phase was extracted with Et$_2$O (2×0.2 mL). The combined organic extracts were washed with water (0.4 mL), dried with MgSO$_4$, and filtered before adding SiO$_2$ (20 mg) and and carefully concentrated under vacuum. The resulting solid was directly loaded into a column containing silica gel, and flash column chromatography (eluting with pentane:Et$_2$O (95:5)) was used to obtain the pure product in 98% yield (85.7 mg, 0.49 mmol) as a colorless oil.

Enantiomeric excess of 99.1% was determined by HPLC [Chiralpak® IB; flow: 1.0 mL/min; hexane:iPA 98:2; λ=210 nm; minor enantiomer $t_R$=4.5 min; major enantiomer $t_R$=4.9 min].

$^1$H NMR (400 MHz, CDCl$_3$) δ$_H$/ppm: 7.29-7.17 (m, 1H), 7.10-7.01 (m, 3H), 5.93 (m, 2H), 4.23 (m, 2H), 4.04 (dd, J=10.1, 4.3 Hz, 1H), 3.61-3.47 (m, 2H), 2.35 (s, 3H).

$^{13}$C NMR (101 MHz, CDCl$_3$) δ$_C$/ppm: 141.9, 138.3, 128.9, 128.5, 128.2, 127.7, 127.0, 125.2, 71.4, 65.6, 41.5, 21.6.

HRMS (EI/FI) m/z calcd for C$_{12}$H$_{14}$O [M]$^+$: 174.1045, found: 174.1046.

IR (ATR) ν (cm$^{-1}$, CHCl$_3$): 1487, 1607, 2844, 2917, 3030.

[α]$^{20}_{589}$=−118.3 (c 0.68 CHCl$_3$) for 99.1% ee.

Example 23—Preparation of (−)-(S)-3-(4-Chlorophenyl)-3,6-dihydro-2H-pyran 24

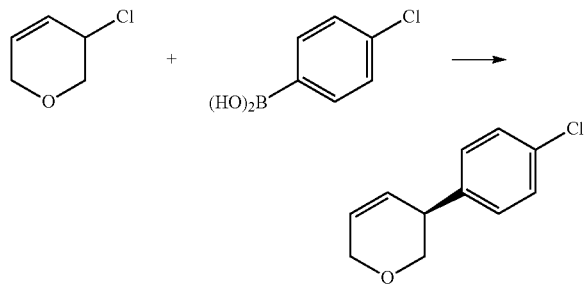

In a 10 mL round bottomed flask [Rh(cod)(OH)]$_2$ (5.7 mg, 0.013 mmol, 0.025 eq), (S)-Xyl-P—PHOS A (22.7 mg, 0.03 mmol, 0.06 eq) and Cs$_2$CO$_3$ (162.9 mg, 0.50 mmol, 1.00 eq) were stirred in THF (2.5 mL) at 60° C. for 30 min. A solution of (4-chlorophenyl)boronic acid (156.4 mg, 1.00 mmol, 2.00 eq) and 3-chloro-3,6-dihydro-2H-pyran (59.3 mg, 0.50 mmol, 1.00 eq) in THF (1.5 mL) was then added via syringe and the flask rinsed with THF (1.0 mL). The resulting mixture was then stirred for 3 h at 60° C. before the addition of NaOH 2M (0.2 mL). The aqueous phase was extracted with Et$_2$O (2×0.2 mL). The combined organic extracts were washed with water (0.4 mL), dried with MgSO$_4$, and filtered before adding SiO$_2$ (20 mg) and carefully concentrated under vacuum. The resulting solid was directly loaded into a column containing silica gel, and flash column chromatography (eluting with pentane:Et$_2$O (95:5)) was used to obtain the pure product in 83% yield (80.5 mg, 0.42 mmol) as a colorless oil.

Enantiomeric excess of 99% was determined by HPLC [Chiralpak® IB; flow: 1.0 mL/min; hexane:iPA 98:2; λ=210 nm; major enantiomer $t_R$=6.0 min; minor enantiomer $t_R$=7.4 min].

$^1$H NMR (400 MHz, CDCl$_3$) δ$_H$/ppm: 7.33-7.24 (m, 2H), 7.23-7.14 (m, 2H), 5.95 (dq, J=10.3, 2.4 Hz, 1H), 5.92-5.84 (m, 1H), 4.22 (q, J=2.5 Hz, 2H), 4.01 (dd, J=10.7, 4.7 Hz, 1H), 3.60-3.44 (m, 2H).

$^{13}$C NMR (101 MHz, CDCl$_3$) δ$_C$/ppm: 140.5, 132.7, 129.6 (2C), 128.8 (2C), 127.5, 127.5, 71.1, 65.5, 40.9.

HRMS (EI/FI) m/z calcd for C$_{11}$H$_{11}$ClO [M]$^+$: 194.0498, found: 190.0499.

IR (ATR) ν (cm$^{-1}$, CHCl$_3$): 1086, 1490, 2843, 2925, 3030.

[α]$^{20}_{589}$=−113.4 (c 2.80 CHCl$_3$) for 99% ee.

Example 24—Preparation of (−)-(S)-3-(4-Methoxyphenyl)-3,6-dihydro-2H-pyran 25

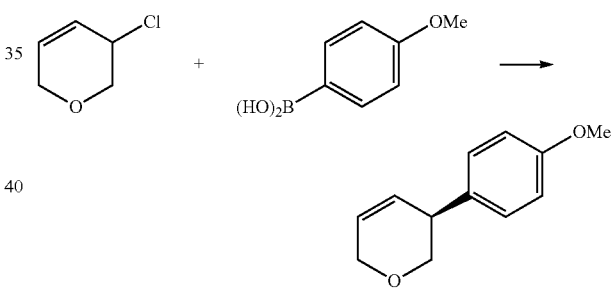

In a 10 mL round bottomed flask [Rh(cod)(OH)]$_2$ (5.7 mg, 0.013 mmol, 0.025 eq), (S)-Xyl-P—PHOS A (22.7 mg, 0.03 mmol, 0.06 eq) and Cs$_2$CO$_3$ (162.9 mg, 0.50 mmol, 1.00 eq) were stirred in THF (2.5 mL) at 60° C. for 30 min. A solution of (4-methoxyphenyl)boronic acid (152.0 mg, 1.00 mmol, 2.00 eq) and 3-chloro-3,6-dihydro-2H-pyran (59.3 mg, 0.50 mmol, 1.00 eq) in THF (1.5 mL) was then added via syringe and the flask rinsed with THF (1.0 mL). The resulting mixture was then stirred for 3 h at 60° C. before the addition of NaOH 2M (0.2 mL). The aqueous phase was extracted with Et$_2$O (2×0.2 mL). The combined organic extracts were washed with water (0.4 mL), dried with MgSO$_4$, and filtered before adding SiO$_2$ (20 mg) and carefully concentrated under vacuum. The resulting solid was directly loaded into a column containing silica gel, and flash column chromatography (eluting with pentane:Et$_2$O (95:5)) was used to obtain the pure product in 81% yield (77.3 mg, 0.41 mmol) as a white solid.

Enantiomeric excess of 99.5% was determined by HPLC [Chiralpak® IB; flow: 1.0 mL/min; hexane:iPA 98:2; λ=210 nm; major enantiomer $t_R$=9.0 min; minor enantiomer $t_R$=10.8 min].

$^1$H NMR (400 MHz, CDCl$_3$) δ$_H$/ppm: 7.21-7.13 (m, 2H), 6.92-6.82 (m, 2H), 5.91 (m, 2H), 4.22 (m, 2H), 4.08-3.96 (m, 1H), 3.80 (s, 3H), 3.61-3.45 (m, 2H).

$^{13}$C NMR (101 MHz, CDCl$_3$) δ$_C$/ppm: 158.6, 134.0, 129.1 (2C), 128.4, 126.9, 114.0 (2C), 71.5, 65.5, 55.4, 40.7.

HRMS (EI/FI) m/z calcd for C$_{12}$H$_{14}$O$_2$ [M]$^+$: 190.0994, found: 190.0998.

IR (ATR) ν (cm$^{-1}$, CHCl$_3$): 1512, 1611, 2844, 2926, 3029.

$[α]^{20}_{589}$=−94.2 (c 1.96 CHCl$_3$) for 99.5% ee.

Example 25—Preparation of (R)-3-(Cyclohex-2-en-1-yl)thiophene 28

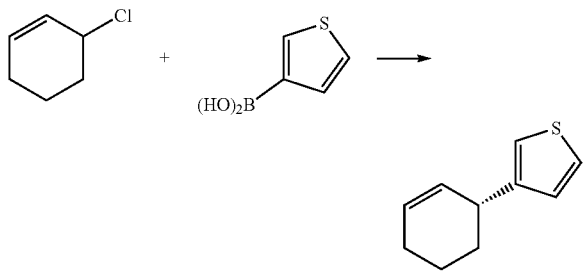

[Rh(cod)(OH)]$_2$ (4.6 mg, 0.02 mmol), (R)-BINAP (14.9 mg, 0.024 mmol) and Cs$_2$CO$_3$ (130.3 mg, 0.40 mmol) were stirred in tetrahydrofuran (2.0 mL) for 30 min under reflux. A solution of 3-chlorocyclohexene (45 μL, 0.4 mmol) and 3-thienylboronic acid (153.6 mg, 1.2 mmol) in tetrahydrofuran (1.5 mL) was then added the flask rinsed with additional tetrahydrofuran (0.5 mL). The reaction mixture was allowed to stir for 1.5 h under reflux before SiO$_2$ (ca. 20 mg) was added. After the solvent was carefully evaporated the solid was loaded directly onto a chromatographic column. Eluting with pentane gave the pure product as a colourless oil (37 mg, 56%).

Enantiomeric excess of 97% was determined by HPLC [Chiralpak® ID; flow: 1 mL/min; hexane/i-PrOH 99.9:0.1; λ=210 nm; minor enantiomer (S)-3-(cyclohex-2-en-1-yl)thiophene, t$_R$=5.38 min; major enantiomer (R)-3-(cyclohex-2-en-1-yl)thiophene, t$_R$=5.84 min].

TLC R$_f$=0.33 (hexane)

$^1$H NMR (400 MHz, CDCl$_3$) δ$_H$/ppm: 1.59-1.70 (m, 2H), 1.71-1.81 (m, 1H), 1.99-2.06 (m, 1H), 2.07-2.16 (m, 2H), 3.46-3.61 (m, 1H), 5.76-5.84 (m, 1H), 5.84-5.93 (m, 1H), 7.00 (d, J=2.9 Hz, 1H), 7.02 (d, J=5.0 Hz, 1H), 7.29 (dd, J=5.0, 2.9 Hz, 1H).

$^{13}$C NMR (100 MHz, CDCl$_3$) δ$_H$/ppm: 21.0, 25.2, 31.3, 37.1, 120.0, 125.3, 127.6, 128.0, 130.1, 147.3.

IR (ATR) ν (cm$^{-1}$): 2931m, 2858s, 2835s, 854s, 839s, 7771, 745s, 736s, 651m, 637s;

$[α]_D^{25}$=+46.5 (c 1.0, CHCl$_3$).

Example 26—Preparation of (R)-2-(Cyclohex-2-en-1-yl)benzofuran 29

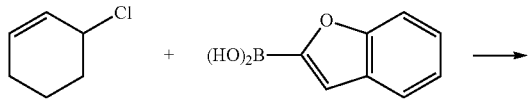

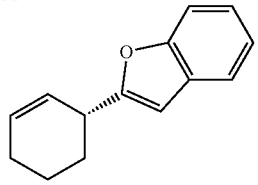

[Rh(cod)(OH)]$_2$ (4.6 mg, 0.02 mmol), (R)-BINAP (14.9 mg, 0.024 mmol) and Cs$_2$CO$_3$ (130.3 mg, 0.40 mmol) were stirred in tetrahydrofuran (2.0 mL) for 30 min under reflux. A solution of 3-chlorocyclohexene (45 μL, 0.4 mmol) and 2-benzofuranylboronic acid (194.3 mg, 1.2 mmol) in tetrahydrofuran (1.5 mL) was then added the flask rinsed with additional tetrahydrofuran (0.5 mL). The reaction mixture was allowed to stir for 1.5 h under reflux before SiO$_2$ (ca. 20 mg) was added. After the solvent was carefully evaporated the solid was loaded directly onto a chromatographic column. Eluting with pentane gave the pure product as a colourless oil (57 mg, 75%).

Enantiomeric excess of 95% was determined by HPLC [Chiralpak® IB; flow: 1.0 mL/min; hexane/i-PrOH 99.9:0.1; λ=210 nm; major enantiomer (R)-2-(cyclohex-2-en-1-yl)benzofuran, t$_R$=6.34 min; minor enantiomer (S)-2-(cyclohex-2-en-1-yl)benzofuran, t$_R$=6.88 min].

$^1$H NMR (400 MHz, CDCl$_3$) δ$_H$/ppm: 1.59-1.71 (m, 1H), 1.72-1.83 (m, 1H), 1.90 (dddd, J=12.8, 9.6, 7.0, 2.9 Hz, 1H), 2.02-2.15 (m, 3H), 3.55-3.68 (m, 1H), 5.81-5.90 (m, 1H), 5.90-5.99 (m, 1H), 6.40 (s, 1H), 7.20 (m, 2H), 7.43 (d, J=7.8 Hz, 1H), 7.47-7.53 (m, 1H).

$^{13}$C NMR (100 MHz, CDCl$_3$) δ$_H$/ppm: 20.3, 25.0, 27.9, 35.4, 101.7, 110.8, 120.3, 122.4, 123.2, 126.4, 128.8, 129.5, 154.7, 162.1.

IR (ATR) ν (cm$^{-1}$): 2933s, 1584s, 1454l, 1254l, 1164m, 949s, 873s, 795m, 7481, 725s.

Example 27—Preparation of (R)-6-(Cyclohex-2-en-1-yl)-1-methyl-1H-indazole 30

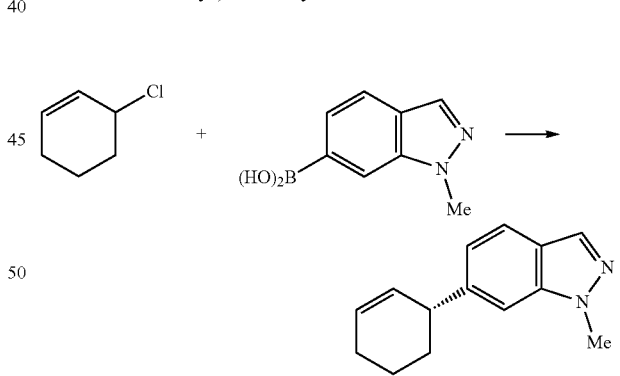

[Rh(cod)(OH)]$_2$ (4.6 mg, 0.01 mmol), (R)-Xylyl-P—PHOS (18.2 mg, 0.024 mmol) and Cs$_2$CO$_3$ (130.3 mg, 0.40 mmol) were stirred in tetrahydrofuran (2.0 mL) for 30 min at 60° C. A solution of 3-chlorocyclohexene (45 μL, 0.4 mmol) and 1-methyl-1H-indazole-6-boronic acid (105.6 mg, 0.6 mmol) in tetrahydrofuran (1.5 mL) was then added the flask rinsed with additional tetrahydrofuran (0.5 mL). The reaction mixture was allowed to stir for 2 h at 60° C. before SiO$_2$ (ca. 20 mg) was added. After the solvent was carefully evaporated the solid was loaded directly onto a chromatographic column. Eluting with pentane gave the pure product as a colourless oil (14 mg, 17%).

Enantiomeric excess of 96% was determined by HPLC [Chiralpak® IB; flow: 1.0 mL/min; hexane/i-PrOH 95:5; λ=210 nm; minor enantiomer (R)-6-(cyclohex-2-en-1-yl)-1-methyl-1H-indazole, $t_R$=10.82 min; major enantiomer (S)-6-(cyclohex-2-en-1-yl)-1-methyl-1H-indazole, $t_R$=11.55 min].

$^1$H NMR (400 MHz, CDCl$_3$) $\delta_H$/ppm: 1.49-1.64 (m, 2H), 1.69 (m, 1H), 1.94-2.11 (m, 3H), 3.49 (m, 1H), 3.98 (s, 3H), 5.71 (dd, J=10.2, 2.4 Hz, 1H), 5.82-5.95 (m, 1H), 6.96 (dd, J=8.4, 1.3 Hz, 1H), 7.12 (d, J=1.5 Hz, 1H), 7.56 (d, J=8.3 Hz, 1H), 7.84 (s, 1H).

$^{13}$C NMR (100 MHz, CDCl$_3$)$^6$H/ppm: 21.2, 25.1, 32.8, 35.4, 42.2, 107.2, 120.7, 121.5, 122.6, 128.8, 130.0, 132.4, 140.4, 145.4.

LRMS (ESI): m/z calcd for $C_{14}H_{17}N_2^+$ [M+H]$^+$: 213.1, found 213.1.

IR (ATR) ν (cm$^{-1}$): 29301, 2859s, 1622m, 1473m, 1440s, 1373s, 1223m, 947s, 839m, 769s;

Example 28—Preparation of (R,E)-(2-(cyclohex-2-en-1-yl)vinyl)benzene 31

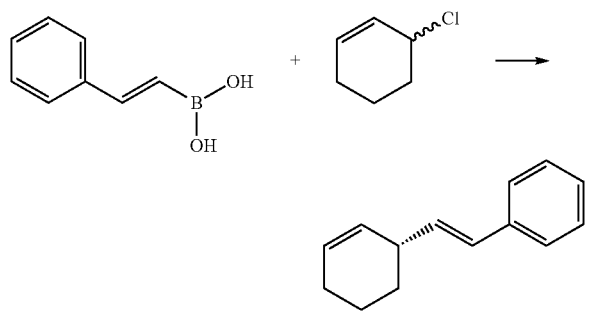

In a 10 mL round bottomed flask [Rh(cod)(OH)]$_2$ (4.6 mg, 0.01 mmol, 0.025 eq), (R)-BINAP A (14.9 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of (E)-styrylboronic acid (118.4 mg, 0.80 mmol, 2.00 eq) and the allyl chloride (45 μL, 0.40 mmol, 1.00 eq) in THF (1.5 mL) was then added via syringe and the flask rinsed with THF (0.5 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (R,E)-(2-(cyclohex-2-en-1-yl)vinyl)benzene in 61% yield (45.2 mg, 0.24 mmol).

Enantiomeric excess of 96% was determined by HPLC [Chiralpak® IE; flow: 0.7 mL/min; hexane; λ=210 nm; major enantiomer $t_R$=10.4 min; minor enantiomer $t_R$=11.2 min].

$^1$H NMR (400 MHz, CDCl$_3$) (7.30 (d, J=1.6 Hz, 1H), 7.28 (s, 1H), 7.22 (t, J=7.7 Hz, 2H), 7.16-7.07 (m, 1H), 6.31 (d, J=15.8 Hz, 1H), 6.12 (dd, J=15.8, 7.4 Hz, 1H), 5.78-5.68 (m, 1H), 5.57 (m, 1H), 2.89 (m, 1H), 1.95 (m, 2H), 1.81 (m, 1H), 1.74-1.61 (m, 1H), 1.59-1.46 (m, 2H).

$^{13}$C NMR (101 MHz, CDCl$_3$) (137.9, 134.8, 129.6, 129.2, 128.6 (2C), 128.2, 127.0, 126.2 (2C), 38.8, 29.4, 25.2, 20.7.

HRMS (EI) m/z calcd for $C_{14}H_{16}$ [M]$^+$: 184.1252, found: 184.1261.

IR (ATR) ν (cm$^{-1}$, CHCl$_3$): 1171, 1542, 2867, 3058.

[α]$^{20}_{589}$=+18.8 (c 0.65 CHCl$_3$) for 92% ee

Example 29—Preparation of (R,E)-3-(5-phenylpent-1-en-1-yl)cyclohex-2-ene 32

Preparation of (E)-5-Phenylpent-1-en-1-ylboronic acid

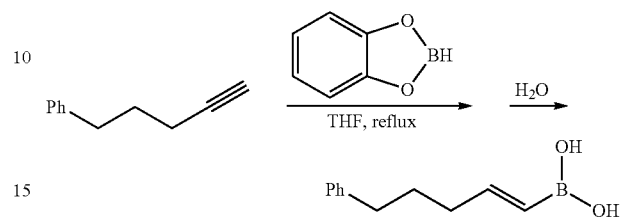

5-Phenyl-1-pentyne (6.23 mL, 41.05 mmol, 1.00 eq) and catecholborane (5.25 mL, 49.26 mmol, 1.20 eq) were dissolved in THF (15.2 mL) and the mixture was refluxed for 18 h. The solvent was evaporated and then H$_2$O (3 mL) was added. The suspension was vigorously stirred for 4 h at room temperature. The solid was filtered and recrystallized with water. (E)-5-phenylpent-1-en-1-ylboronic acid (5.0 g, 26.3 mmol, 64%) was then filtered and dried under vacuum.

$^1$H NMR (400 MHz, DMSO-d$_6$) $\delta_H$/ppm: 7.52 (br. s, 2H), 7.32-7.23 (m, 2H), 7.23-7.12 (m, 3H), 6.47 (dt, J=17.9, 6.4 Hz, 1H), 5.34 (dt, J=17.8, 1.6 Hz, 1H), 2.62-2.53 (m, 2H), 2.16-2.03 (m, 2H), 1.66 (p, J=7.5 Hz, 2H).

$^{13}$C NMR (101 MHz, DMSO) $\delta_C$/ppm: 149.6, 142.1, 128.4 (2C), 128.3 (2C), 125.7, 119.3, 34.6, 34.5, 30.0.

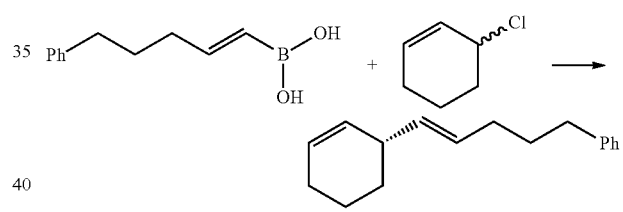

In a 10 mL round bottomed flask [Rh(cod)(OH)]$_2$ (4.6 mg, 0.01 mmol, 0.025 eq), (R)-BINAP A (14.9 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of (E)-(5-phenylpent-1-en-1-yl)boronic acid (152.0 mg, 0.80 mmol, 2.00 eq) and the allyl chloride (45 μL, 0.40 mmol, 1.00 eq) in THF (1.5 mL) was then added via syringe and the flask rinsed with THF (0.5 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (R,E)-3-(5-phenylpent-1-en-1-yl)cyclohex-2-ene in 76% yield (69.2 mg, 0.30 mmol).

Enantiomeric excess of 93% was determined by HPLC [Chiralpak® IA; flow: 0.2 mL/min; hexane; λ=210 nm; major enantiomer $t_R$=21.5 min; minor enantiomer $t_R$=22.5 min].

$^1$H NMR (500 MHz, CDCl$_3$) $\delta_H$/ppm 5.75-5.68 (m, 1H), 5.57 (d, J=2.5 Hz, 1H), 5.43-5.39 (m, 2H), 3.80 (m, 1H), 2.22-2.13 (m, 2H), 2.09 (m, 1H), 2.02-1.94 (m, 2H), 1.82-1.75 (m, 1H), 1.70 (m, 1H), 1.59-1.49 (m, 1H), 1.43-1.34 (m, 1H), 1.12 (d, J=6.1 Hz, 3H), 0.89 (s, 9H), 0.06 (s, 6H).

$^{13}$C NMR (100 MHz, CDCl$_3$) $\delta_C$/ppm 142.7, 134.8, 130.4, 129.2, 128.5 (2C), 128.3 (2C), 127.4, 125.6, 38.4, 35.4, 32.1, 31.3, 29.5, 25.1, 20.6.

HRMS (EI) m/z calcd for $C_{17}H_{22}Na$ [M+Na]$^+$: 249.1619, found: 249.1621.
IR ($v_{max}$/cm$^{-1}$): 1472.3, 2854.8, 2929.2.

Example 30—Preparation of (R,E)-1-(3-Cyclohexenyl)-1-hexene 33

Preparation of (E)-Hex-1-en-1-ylboronic acid

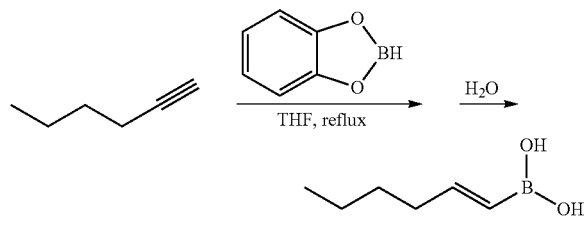

1-Hexyne (4.70 mL, 41.05 mmol, 1.00 eq) and catecholborane (5.25 mL, 49.26 mmol, 1.20 eq) were dissolved in THF (15.2 mL) and the mixture was refluxed for 18 h. The solvent was evaporated and then $H_2O$ (3 mL) was added. The suspension was vigorously stirred for 4 h at room temperature. The solid was filtered and recrystallized with water. (E)-Hex-1-en-1-ylboronic acid (2.80 g, 21.9 mmol, 85%) was then filtered and dried under vacuum.

$^1$H NMR (500 MHz, DMSO-d$_6$) $\delta_H$/ppm 7.48 (br. s, 2H), 6.43 (dt, J=17.8, 6.5 Hz, 1H), 5.31 (dt, J=17.8, 1.6 Hz, 1H), 2.11-2.03 (m, 2H), 1.39-1.23 (m, 4H), 0.87 (t, J=7.2 Hz, 3H).

$^{13}$C NMR (126 MHz, DMSO) $\delta_C$/ppm: 150.5, 125.2, 35.1, 30.7, 22.1, 14.3.

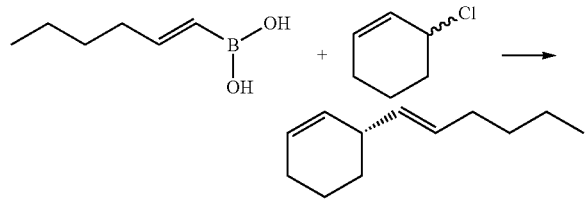

In a 10 mL round bottomed flask [Rh(cod)(OH)]$_2$ (4.6 mg, 0.01 mmol, 0.025 eq), (R)-BINAP A (14.9 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of (E)-hex-1-en-1-ylboronic acid (102.4 mg, 0.80 mmol, 2.00 eq) and the allyl chloride (45 µL, 0.40 mmol, 1.00 eq) in THF (1.5 mL) was then added via syringe and the flask rinsed with THF (0.5 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (R,E)-1-(3-cyclohexenyl)-1-hexene in 61% yield (40.1 mg, 0.24 mmol).

Enantiomeric excess of 98% was determined by GC [Hydrodex® β-3P 60° C. 0 min then 1° C./min to 160° C. Minor enantiomer t$_R$=35.0 min; major enantiomer t$_R$=38.5 min].

$^1$H NMR (400 MHz, CDCl$_3$) $\delta_H$/ppm 5.71 (dq, J=9.8, 3.7, 1H), 5.62-5.49 (m, 1H), 5.46-5.32 (m, 2H), 2.72 (m, 1H), 2.11-1.90 (m, 5H), 1.86-1.63 (m, 2H), 1.59-1.40 (m, 1H), 1.41-1.24 (m, 4H), 0.89 (t, J=7.0 Hz, 3H).

$^{13}$C NMR (101 MHz, CDCl$_3$) $\delta_C$/ppm 134.3, 130.7, 129.9, 127.3, 38.5, 32.4, 31.9, 29.7, 25.2, 22.3, 20.8, 14.1.
HRMS (EI) m/z calcd for $C_{12}H_{20}$ [M]$^+$: 164.1565, found: 164.1564.
IR ($v_{max}$/cm$^{-1}$): 1541, 2859, 2957, 3011.
$[\alpha]^{20}_{589}$=+93.6 (c 1.18 CHCl$_3$) for 98% ee.

Example 31—Preparation of (R,E)-1-(2-(Cyclohex-2-en-1-yl)vinyl)-4-fluorobenzene 34

Preparation of (E)-(4-Fluorostyryl)boronic acid

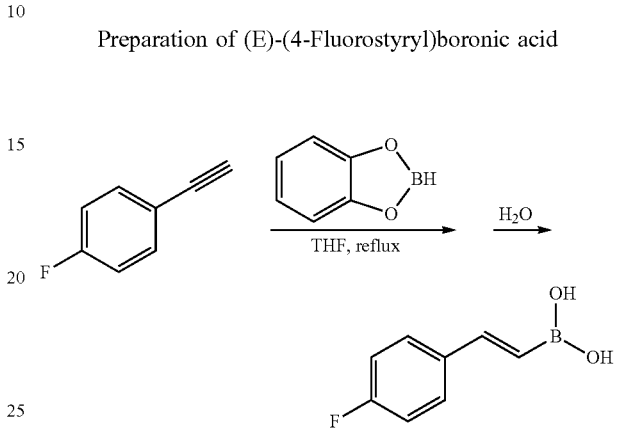

1-Ethynyl-4-fluorobenzene (0.50 g, 4.40 mmol, 1.00 eq) and catecholborane (0.56 mL, 5.20 mmol, 1.20 eq) were dissolved in THF (1.6 mL) and the mixture was refluxed for 18 h. The solvent was evaporated and then $H_2O$ (1 mL) was added. The suspension was vigorously stirred for 4 h at room temperature. The solid was filtered and recrystallized with water. (E)-5-phenylpent-1-en-1-ylboronic acid (452.3 mg, 2.72 mmol, 62%) was then filtered and dried under vacuum.

$^1$H NMR (500 MHz, DMSO-d$_6$) $\delta_H$/ppm 7.82 (s, 2H), 7.57-7.49 (m, 2H), 7.26 (s, 1H), 7.24-7.14 (m, 3H), 6.73 (dd, J=5.9, 3.6 Hz, 0.5H), 6.60 (dd, J=5.9, 3.6 Hz, 0.5H), 6.06 (d, J=18.4 Hz, 1H).

$^{13}$C NMR (126 MHz, DMSO) $\delta_C$/ppm: 163.6, 161.6, 145.7, 145.0, 134.7, 134.7, 129.1, 129.0, 123.6, 119.7, 116.1, 115.9, 115.6.

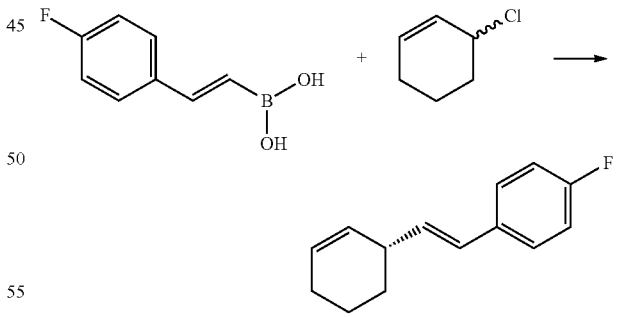

In a 10 mL round bottomed flask [Rh(cod)(OH)]$_2$ (4.6 mg, 0.01 mmol, 0.025 eq), (R)-BINAP A (14.9 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of (E)-(4-fluorostyryl)boronic acid (132.8 mg, 0.80 mmol, 2.00 eq) and the allyl chloride (451 L, 0.40 mmol, 1.00 eq) in THF (1.5 mL) was then added via syringe and the flask rinsed with THF (0.5 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (R,E)-1-(2-(cyclohex-2-en-1-yl)vinyl)-4-fluorobenzene in 62% yield (50.5 mg, 0.25 mmol).

Enantiomeric excess of 96% was determined by GC [Hydrodex® 6-TBDM 80° C. for 0 min then 2° C./min to 110° C., hold for 20 min then 1° C./min to 150° C. Minor enantiomer $t_R$=53.6 min; major enantiomer $t_R$=54.1 min].

$^1$H NMR (400 MHz, CDCl$_3$) $\delta_H$/ppm 7.37-7.27 (m, 2H), 6.98 (t, J=8.7 Hz, 2H), 6.35 (d, J=15.9 Hz, 1H), 6.10 (dd, J=15.9, 7.4 Hz, 1H), 5.81 (dq, J=9.8, 3.3 Hz, 1H), 5.63 (dq, J=10.1, 2.7 Hz, 1H), 2.95 (m, 1H), 2.03 (m, 2H), 1.94-1.82 (m, 1H), 1.75 (m, 1H), 1.68-1.45 (m, 2H).

$^{13}$C NMR (101 MHz, CDCl$_3$) $\delta_C$/ppm 162.1 (d, J=245.6 Hz), 134.6 (d, J=2.2 Hz), 134.1 (d, J=3.3 Hz), 129.5, 128.3, 128.0, 127.6 (d, J=7.8 Hz, 2C), 115.4 (d, J=21.5 Hz, 2C), 38.7, 29.4, 25.2, 20.7.

Example 32—Preparation of (R,E)-1-(2-(Cyclohex-2-en-1-yl)vinyl)-4-bromobenzene 35

Preparation of (E)-(4-Bromostyryl)boronic acid

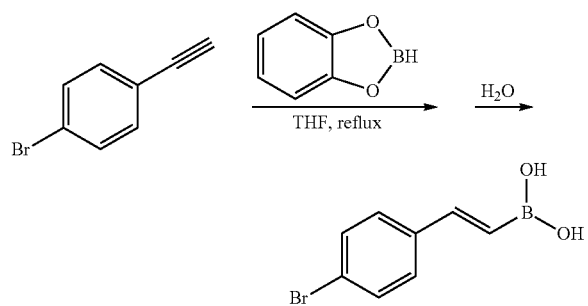

1-Ethynyl-4-bromobenzene (0.50 g, 2.76 mmol, 1.00 eq) and catecholborane (0.35 mL, 3.31 mmol, 1.20 eq) were dissolved in THF (1.0 mL) and the mixture was refluxed for 18 h. The solvent was evaporated and then H$_2$O (1 mL) was added. The suspension was vigorously stirred for 4 h at room temperature. The solid was filtered and recrystallized with water. (E)-5-phenylpent-1-en-1-ylboronic acid (515.0 mg, 2.27 mmol, 82%) was then filtered and dried under vacuum.

$^1$H NMR (400 MHz, DMSO-d$_6$) $\delta_H$/ppm 8.83 (s, OH), 7.87 (s, 2H), 7.59-7.51 (m, 2H), 7.47-7.40 (m, 2H), 7.21 (d, J=18.4 Hz, 1H), 6.73 (dd, J=5.9, 3.6 Hz, 0.5H), 6.64-6.52 (m, 0.5H), 6.15 (d, J=18.4 Hz, 1H).

$^{13}$C NMR (101 MHz, DMSO) $\delta_C$/ppm: 145.7, 144.9, 137.3, 132.1, 129.1, 124.9, 121.9, 119.7, 116.1.

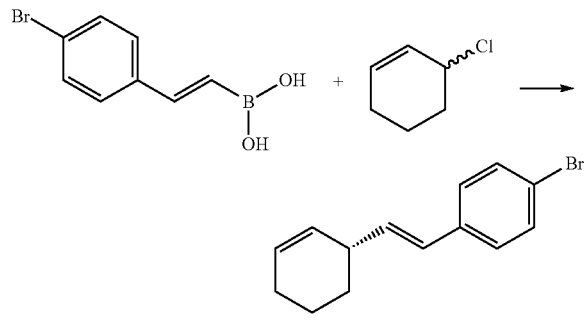

In a 10 mL round bottomed flask [Rh(cod)(OH)]$_2$ (4.6 mg, 0.01 mmol, 0.025 eq), (R)-BINAP A (14.9 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of (E)-(4-bromostyryl)boronic acid (181.4 mg, 0.80 mmol, 2.00 eq) and the allyl chloride (45 µL, 0.40 mmol, 1.00 eq) in THF (1.5 mL) was then added via syringe and the flask rinsed with THF (0.5 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (R,E)-1-(2-(cyclohex-2-en-1-yl)vinyl)-4-bomobenzene in 45% yield (47.3 mg, 0.18 mmol).

Enantiomeric excess of 84% was determined by HPLC [Chiralpak® ID; flow: 0.7 mL/min; hexane; λ=210 nm; major enantiomer $t_R$=10.4 min; minor enantiomer $t_R$=11.2 min].

$^1$H NMR (400 MHz, CDCl$_3$) $\delta_H$/ppm 7.41 (d, J=8.4 Hz, 2H), 7.22 (d, J=8.5 Hz, 2H), 6.32 (d, J=16.0 Hz, 1H), 6.18 (dd, J=15.9, 7.3 Hz, 1H), 5.81 (dq, J=9.8, 2.2 Hz, 1H), 5.62 (dq, J=10.1, 2.5 Hz, 1H), 3.00-2.89 (m, 1H), 2.03 (m, 2H), 1.87 (m, 1H), 1.73 (m, 1H), 1.69-1.44 (m, 2H).

$^{13}$C NMR (101 MHz, CDCl$_3$) $\delta_C$/ppm 136.9, 135.7, 131.7 (2C), 129.3, 128.5, 128.1, 127.7 (2C), 120.7, 38.8, 29.3, 25.2, 20.6.

Example 33—Preparation of (R,E)-1-(2-(Cyclohex-2-en-1-yl)vinyl)-4-methylbenzene 36

Preparation of (E)-(4-Methylstyryl)boronic acid

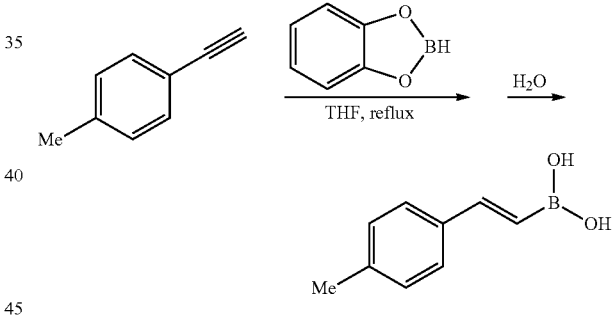

1-Ethynyl-4-methylbenzene (0.50 mL, 3.94 mmol, 1.00 eq) and catecholborane (0.50 mL, 4.73 mmol, 1.20 eq) were dissolved in THF (1.5 mL) and the mixture was refluxed for 18 h. The solvent was evaporated and then H$_2$O (1 mL) was added. The suspension was vigorously stirred for 4 h at room temperature. The solid was filtered and recrystallized with water. (E)-5-phenylpent-1-en-1-ylboronic acid (309.4 mg, 1.90 mmol, 48%) was then filtered and dried under vacuum.

$^1$H NMR (400 MHz, DMSO-d$_6$) $\delta_H$/ppm 7.73 (s, 2H), 7.36 (d, J=7.9 Hz, 2H), 7.18 (d, J=7.9 Hz, 2H), 6.05 (d, J=18.3 Hz, 1H), 2.31 (s, 3H).

$^{13}$C NMR (101 MHz, DMSO) $\delta_C$/ppm: 146.2, 138.4, 135.4, 129.8 (2C), 127.0 (2C), 21.3.

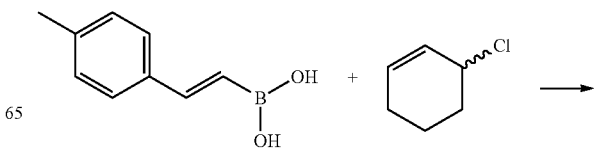

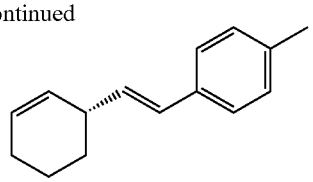

In a 10 mL round bottomed flask [Rh(cod)(OH)]$_2$ (4.6 mg, 0.01 mmol, 0.025 eq), (R)-BINAP A (14.9 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of (E)-(4-methylstyryl)boronic acid (129.6 mg, 0.80 mmol, 2.00 eq) and the allyl chloride (45 μL, 0.40 mmol, 1.00 eq) in THF (1.5 mL) was then added via syringe and the flask rinsed with THF (0.5 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (R,E)-1-(2-(cyclohex-2-en-1-yl)vinyl)-4-methylbenzene in 95% yield (75.0 mg, 0.38 mmol).

Enantiomeric excess of 88% was determined by HPLC [Chiralpak® ID; flow: 0.6 mL/min; hexane; λ=210 nm; major enantiomer t$_R$=16.1 min; minor enantiomer t$_R$=17.0 min].

$^1$H NMR (400 MHz, CDCl$_3$) δ$_H$/ppm 7.21-7.14 (m, 2H), 7.02 (d, J=7.7 Hz, 2H), 6.27 (d, J=15.9 Hz, 1H), 6.10-6.00 (m, 1H), 5.76-5.66 (m, 1H), 5.56 (m, 1H), 2.87 (m, 1H), 2.24 (s, 3H), 1.94 (m, 2H), 1.86-1.73 (m, 1H), 1.66 (m, 1H), 1.47 (m, 2H).

$^{13}$C NMR (101 MHz, CDCl$_3$) δ$_C$/ppm 136.7, 135.2, 133.8, 129.8, 129.3 (2C), 129.0, 128.1, 126.1 (2C), 38.8, 29.5, 25.3, 21.3, 20.7.

Example 34—Preparation of (R,E)-1-Chloro-4-(2-(cyclohex-2-en-1-yl)vinyl)benzene 37

Preparation of (E)-(4-Chlorostyryl)boronic acid

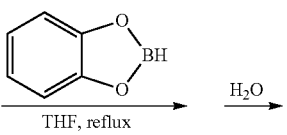

1-Chloro-4-ethynylbenzene (0.50 g, 3.66 mmol, 1.00 eq) and catecholborane (0.47 mL, 4.39 mmol, 1.20 eq) were dissolved in THF (1.4 mL) and the mixture was refluxed for 18 h. The solvent was evaporated and then H$_2$O (1 mL) was added. The suspension was vigorously stirred for 4 h at room temperature. The solid was filtered and recrystallized with water. (E)-(4-chlorostyryl)boronic acid (652.9 mg, 3.62 mmol, 99%) was then filtered and dried under vacuum.

$^1$H NMR (400 MHz, DMSO-d$_6$) δ$_H$/ppm 7.83 (s, 2H), 7.50 (d, J=8.4 Hz, 2H), 7.45-7.39 (m, 2H), 7.24 (d, J=18.4 Hz, 1H), 6.14 (d, J=18.3 Hz, 1H).

$^{13}$C NMR (101 MHz, DMSO) δ$_C$/ppm: 145.7, 144.8, 137.0, 133.3, 129.2 (2C), 128.7 (2C).

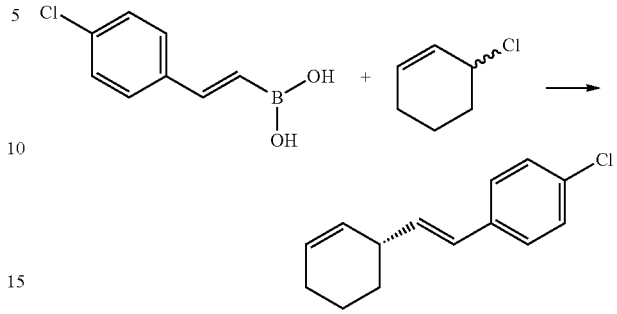

In a 10 mL round bottomed flask [Rh(cod)(OH)]$_2$ (4.3 mg, 0.01 mmol, 0.025 eq), (R)-BINAP A (14.2 mg, 0.023 mmol, 0.06 eq) and Cs$_2$CO$_3$ (123.8 mg, 0.38 mmol, 1.00 eq) were stirred in THF (1.9 mL) at 60° C. for 30 min. A solution of (E)-(4-chlorostyryl)boronic acid (139.5 mg, 0.76 mmol, 2.00 eq) and the allyl chloride (43 μL, 0.38 mmol, 1.00 eq) in THF (1.5 mL) was then added via syringe and the flask rinsed with THF (0.4 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (R,E)-1-chloro-4-(2-(cyclohex-2-en-1-yl)vinyl)benzene in 38% yield (31.6 mg, 0.14 mmol).

Enantiomeric excess of 82% was determined by HPLC [Chiralpak® ID; flow: 0.6 mL/min; hexane; λ=210 nm; major enantiomer t$_R$=12.4 min; minor enantiomer t$_R$=13.2 min].

$^1$H NMR (400 MHz, CDCl$_3$) δ$_H$/ppm 7.30-7.13 (m, 1H), 7.18 (s, 2H), 6.25 (d, J=15.9 Hz, 1H), 6.09 (dd, J=15.9, 7.4 Hz, 1H), 5.73 (m, 1H), 5.55 (m, 1H), 2.87 (m, 1H), 1.95 (m, 2H), 1.86-1.74 (m, 1H), 1.65 (m, 1H), 1.59-1.37 (m, 1H).

$^{13}$C NMR (101 MHz, CDCl$_3$) δ$_C$/ppm 136.5, 135.6, 132.6, 129.3, 128.7 (2C), 128.5, 128.0, 127.4 (2C), 38.8, 29.3, 25.2, 20.6.

Example 35—Preparation of (R)-2-(cyclohex-2-en-1-yl)benzofuran 29

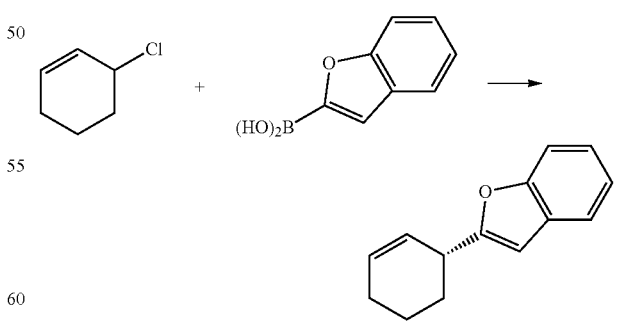

In a 10 mL round bottomed flask [Rh(cod)(OH)]$_2$ (4.6 mg, 0.01 mmol, 0.025 eq), (R)-Xyl-P—PHOS (18.2 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of benzofuran-2-ylboronic acid (129.6 mg, 0.80 mmol, 2.00 eq) and 3-chlorocyclohexene (45 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly loaded into a chromatographic column eluting with pentane to obtain the pure product in 75% yield (57.0 mg, 0.30 mmol) as a colorless oil.

Enantiomeric excess of 95% was determined by HPLC [Chiralpak® IB; flow: 1.0 mL/min; hexane/i-PrOH: 99.9:0.1; λ=210 nm; major enantiomer $t_R$=6.3 min; minor enantiomer $t_R$=6.9 min].

TLC $R_f$=0.29 (hexane).

$^1$H-NMR (400 MHz, CDCl$_3$): $\delta_H$/ppm=1.59-1.71 (m, 1H, H-5$_a$), 1.72-1.83 (m, 1H, H-5$_b$), 1.90 (dddd, J=12.8, 9.6, 7.0, 2.9 Hz, 1H, H-6$_a$), 2.02-2.15 (m, 3H, H-4$_a$, H-4$_b$, H-6$_b$), 3.55-3.68 (m, 1H, H-1), 5.81-5.90 (m, 1H, H-2), 5.90-5.99 (m, 1H, H-3), 6.40 (s, 1H, H-3'), 7.20 (m, 2H, H-5', H-6'), 7.43 (d, J=7.8 Hz, 1H, H-4'), 7.47-7.53 (m, 1H, H-7').

$^{13}$C-NMR (100 MHz, CDCl$_3$): $\delta_H$/ppm=20.34 (C-5), 24.99 (C-4), 27.93 (C-6), 35.35 (C-1), 101.74 (C-3'), 110.81 (C-4'), 120.33 (C-7'), 122.37, 123.17 (C-5', C-6'), 126.41 (C-2), 128.84 (C-3a' or C—C-8a'), 129.45 (C-3), 154.73 (C-3a' or C-7a'), 162.07 (C-2'). [α]$_D^{25}$=+167.5° (c 1.0, CHCl$_3$).

IR (ATR) $\nu_{max}$/cm$^{-1}$=2933s, 1584s, 1454l, 1254l, 1164m, 949s, 873s, 795m, 7481, 725s.

HRMS (EI): m/z calc. for C$_{14}$H$_{14}$O+[M]$^+$: 198.1045, found: 198.1047.

Example 36—Preparation of (−)-(S)-6-(Cyclohex-2-en-1-yl)-1-methyl-1H-indazole 38

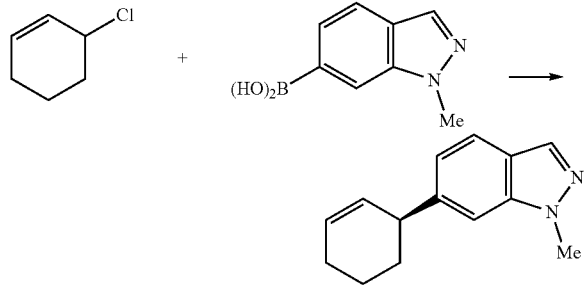

Rh(cod)(OH)]$_2$ (4.6 mg, 0.01 mmol), (S)-BINAP (18.2 mg, 0.024 mmol) and Cs$_2$CO$_3$ (130.3 mg, 0.40 mmol) were stirred in tetrahydrofuran (2.0 mL) for 30 min under reflux. A solution of 3-chlorocyclohexene (45 μL, 0.4 mmol) and 1-methyl-1H-indazole-6-boronic acid (211.2 mg, 1.2 mmol) in tetrahydrofuran (1.5 mL) was then added the flask rinsed with additional tetrahydrofuran (0.5 mL). The reaction mixture was allowed to stir for 2 h under reflux before SiO$_2$ (ca. 20 mg) was added. After the solvent was carefully evaporated the solid was loaded directly onto a chromatographic column. Eluting with petrol ether and ethyl acetate (6:1) gave the pure product as an off white solid (57 mg, 68%).

HPLC analysis indicated an enantiomeric excess of 99% [Chiralpak® IB; flow: 1.0 mL/min; hexane/i-PrOH 95:5; λ=210 nm; minor enantiomer (R)-6-(cyclohex-2-en-1-yl)-1-methyl-1H-indazole, $t_R$=10.82 min; major enantiomer (S)-6-(cyclohex-2-en-1-yl)-1-methyl-1H-indazole, $t_R$=11.55 min].

TLC $R_f$=0.44 (hexane/EtOAc 3:2).

$^1$H-NMR (400 MHz, CDCl$_3$): $\delta_H$/ppm=1.49-1.64 (m, 2H, H-5$_a$, H-6$_a$), 1.69 (m, 1H, H-5$_b$), 1.94-2.11 (m, 3H, H-6$_b$), 3.49 (m, 1H, H-4$_a$, H-4$_b$, H-6$_b$), 3.98 (s, 3H, NCH$_3$), 5.71 (dd, J=10.2, 2.4 Hz, 1H, H-2), 5.82-5.95 (m, 1H, H-3), 6.96 (dd, J=8.4, 1.3 Hz, 1H, H-5'), 7.12 (d, J=1.5 Hz, 1H, H-7'), 7.56 (d, J=8.3 Hz, 1H, H-4'), 7.84 (s, 1H, H-3').

$^{13}$C-NMR (100 MHz, CDCl$_3$): $\delta_H$/ppm=21.18 (C-5), 25.07 (C-4), 32.75 (C-6), 35.44 (NCH$_3$), 42.24 (C-1), 107.17 (C-7'), 120.70 (C-4'), 121.53 (C-5'), 122.62 (C-3a'), 128.75 (C-3), 130.02 (C-2), 132.44 (C-3'), 140.35 (C-7a'), 145.42 (C-6').

[α]$_D^{25}$=−166.7° (c 1.0, CHCl$_3$); T$_{mp}$=82° C.

IR (ATR) $\nu_{max}$/cm$^{-1}$=29301, 2859s, 1622m, 1473m, 1440s, 1373s, 1223m, 947s, 839m, 769s.

HRMS (EI/FI): m/z calc. for C$_{14}$H$_{16}$N$_2^+$ [M]$^+$: 212.1313, found: 212.1310.

Example 37—Preparation of (−)-(S)-2-Chloro-6-(cyclohex-2-en-1-yl)-pyridine 39

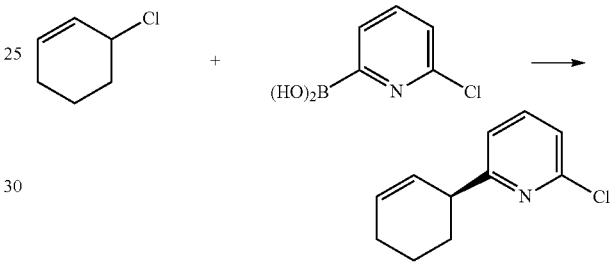

[Rh(cod)(OH)]$_2$ (4.6 mg, 0.01 mmol), (S)-BINAP (14.9 mg, 0.024 mmol) and Cs$_2$CO$_3$ (130.3 mg, 0.40 mmol) were stirred in tetrahydrofuran (2.0 mL) for 30 min under reflux. A solution of 3-chlorocyclohexene (45 μL, 0.4 mmol) and 6-chloro-2-pyridinylboronic acid (188.8 mg, 1.2 mmol) in tetrahydrofuran (1.5 mL) was then added and the flask rinsed with additional tetrahydrofuran (0.5 mL). The reaction mixture was allowed to stir for 12 h under reflux before SiO$_2$ (ca. 20 mg) was added. After the solvent was carefully evaporated the solid was loaded directly onto a chromatographic column. Eluting with petrol ether and ethyl acetate (97:3) gave the pure product as a colourless oil 28.1 mg, 37%).

HPLC analysis indicated an enantiomeric excess of 97% [Chiralpak® ID; flow: 1.0 mL/min; hexane/i-PrOH 99.7:0.3; λ=210 nm; minor enantiomer (+)-(R)-2-chloro-6-(cyclohex-2-en-1-yl)-pyridine, $t_R$=6.84 min; major enantiomer (−)-(S)-2-chloro-6-(cyclohex-2-en-1-yl)-pyridine, $t_R$=8.03 min].

TLC $R_f$=0.50 (hexane/EtOAc 9:1).

$^1$H-NMR (400 MHz, CDCl$_3$): $\delta_H$/ppm=1.59-1.75 (m, 3H, H-5$_a$, H-5$_b$, H-6$_a$), 2.03-2.13 (m, 3H, H-4$_a$, H-4$_b$, H-6$_b$), 3.56 (dddd, J=7.9, 5.4, 2.8, 2.8 Hz, 1H, H-1), 5.71-5.79 (m, 1H, H-2), 5.93 (dddd, J=9.8, 3.6, 3.6, 2.3 Hz, 1H, H-3), 7.11 (dd, J=7.6, 0.9 Hz, 1H, H-5'), 7.14 (dd, J=7.9, 0.9 Hz, 1H, H-3'), 7.56 (dd, J=7.9, 7.6 Hz, 1H, H-4').

$^{13}$C-NMR (100 MHz, CDCl$_3$): $\delta_H$/ppm=20.89 (C-5), 25.07 (C-4), 30.48 (C-6), 43.72 (C-1), 120.19 (C-5'), 121.72 (C-3'), 127.98 (C-2), 129.67 (C-3), 139.02 (C-4'), 150.77 (C-2'), 166.72 (C-5'). [α]$_D^{25}$=−72.0° (c 1.0, CHCl$_3$).

IR (ATR) $\nu_{max}$/cm$^{-1}$=2931s, 1581m, 1557m, 14351, 1156s, 1133m, 791m, 727m, 663s.

HRMS (ESI): m/z calc. for C$_{11}$H$_{13}$ClN$^+$[M+H]$^+$: 194.0731, found: 194.0733.

Example 38—Preparation of (−)-(R)-5-(Cyclohex-2-en-1-yl)-1H-indole 40

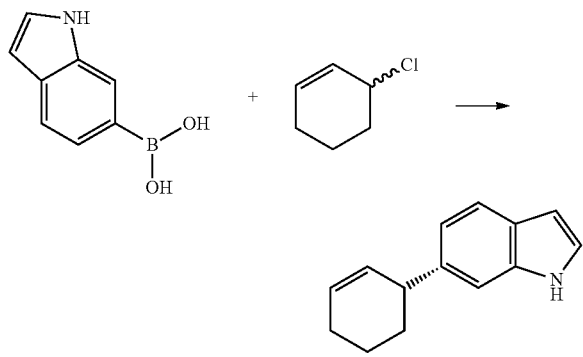

[Rh(cod)(OH)]$_2$ (4.6 mg, 0.01 mmol), (R)-BINAP (14.9 mg, 0.024 mmol) and Cs$_2$CO$_3$ (130.3 mg, 0.40 mmol) were stirred in tetrahydrofuran (2.0 mL) for 30 min under reflux. A solution of 3-chlorocyclohexene (45 µL, 0.4 mmol) and 5-indolylboronic acid (193.2 mg, 1.2 mmol) in tetrahydrofuran (1.5 mL) was then added the flask rinsed with additional tetrahydrofuran (0.5 mL). The reaction mixture was allowed to stir for 1.5 h under reflux before SiO$_2$ (ca. 20 mg) was added. After the solvent was carefully evaporated the solid was loaded directly onto a chromatographic column. Eluting with a mixture of petrol ether and ethyl acetate (9:1, 1% triethylamine) gave the pure product as a colourless oil (33 mg, 41%).

HPLC analysis indicated an enantiomeric excess of 96% [Chiralpak® IC; flow: 1.0 mL/min; hexane/i-PrOH 97:3; λ=210 nm; major enantiomer (−)-(R)-5-(cyclohex-2-en-1-yl)-1H-indole, $t_R$=9.14 min; minor enantiomer (−)-(S)-5-(cyclohex-2-en-1-yl)-1H-indole, $t_R$=9.81 min]

TLC R$_f$=0.33 (hexane/EtOAc 4:1).

$^1$H-NMR (400 MHz, CDCl$_3$): δ$_H$/ppm=1.59-1.73 (m, 2H, H-5$_a$, H-6$_a$), 1.74-1.86 (m, 1H, H-5$_b$), 2.02-2.19 (m, 3H, H-4$_a$, H-4$_b$, H-6$_b$), 3.53 (m, 1H, H-1), 5.76-5.87 (m, 1H, H-2), 5.87-5.96 (m, 1H, H-3), 6.53 (dd, J=2.5, 2.5 Hz, 1H, H-2'), 7.10 (dd, J=8.4, 1.6 Hz, 1H, H-6'), 7.18 (d, J=2.8 Hz, 1H, H-3'), 7.33 (d, J=8.3 Hz, 1H, H-7'), 7.51 (d, J=1.6 Hz, 1H, H-4'), 8.03 (br, 1H, NH).

$^{13}$C-NMR (100 MHz, CDCl$_3$): δ$_H$/ppm=21.47 (C-5), 25.29 (C-4), 33.36 (C-6), 42.08 (C-1), 102.58 (C-2'), 110.88 (C-7'), 119.40 (C-4'), 122.58 (C-6'), 124.40 (C-3'), 127.92 (C-3), 128.10 (C-7a'), 131.42 (C-2), 134.63 (C-3a'), 138.33 (C-5').

[α]$_D^{25}$=−161.4° (c 1.0, CHCl$_3$).

IR (ATR) ν$_{max}$/cm$^{-1}$=3410m, 2926m, 1474s, 1453s, 1415s, 1336s, 895s, 806s, 764m, 722l.

HRMS (EI/FI): m/z calc. for C$_{14}$H$_{15}$N$^+$ [M]$^+$: 197.1204, found: 197.1212.

Example 39—Preparation of (+)-(R)-(1-(cyclohex-2-en-1-yl)vinyl)benzene 41

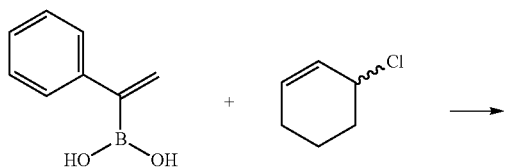

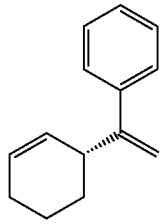

In a 10 mL round bottomed flask [Rh(cod)(OH)]$_2$ (4.6 mg, 0.01 mmol, 0.025 eq), (R)-BINAP A (14.9 mg, 0.024 mmol, 0.06 eq) and Cs$_2$CO$_3$ (130.3 mg, 0.40 mmol, 1.00 eq) were stirred in THF (2.0 mL) at 60° C. for 30 min. A solution of (1-phenylvinyl)boronic acid (118.4 mg, 0.80 mmol, 2.00 eq) and the allyl chloride (45 µL, 0.40 mmol, 1.00 eq) in THF (1.5 mL) was then added via syringe and the flask rinsed with THF (0.5 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (+)-(R)-(1-(cyclohex-2-en-1-yl)vinyl)benzene in 75% yield (55.3 mg, 0.30 mmol).

Enantiomeric excess of 94% was determined by HPLC [Chiralpak® ID; flow: 0.4 mL/min; hexane; λ=210 nm; major enantiomer $t_R$=15.2 min; minor enantiomer $t_R$=16.2 min].

$^1$H NMR (400 MHz, CDCl$_3$) δ$_H$/ppm 7.32-7.27 (m, 1H), 7.27-7.15 (m, 2H), 7.15-7.05 (m, 1H), 6.35-6.26 (d, J=15.9 Hz, 1H), 6.12 (dd, J=15.9, 7.4 Hz, 1H), 5.80-5.68 (m, 1H), 5.57 (dd, J=10.1, 2.6 Hz, 1H), 2.94-2.83 (m, 1H), 1.95 (dq, J=5.9, 3.1 Hz, 2H), 1.89-1.75 (m, 1H), 1.75-1.60 (m, 1H), 1.60-1.35 (m, 2H).

$^{13}$C NMR (101 MHz, CDCl$_3$) 137.9, 134.8, 129.6, 129.2, 128.6, 128.2 (2C), 127.0, 126.2 (2C), 38.8, 29.4, 25.2, 20.7.

HRMS (EI) m/z calcd for C$_{14}$H$_{16}$ [M]$^+$: 184.1252, found: 184.1250.

IR (ν$_{max}$/cm$^{-1}$): 1447, 1495, 1598, 2858, 2929, 3022.

[α]$^{25}_{589}$=+252.4 (c 1.10 CHCl$_3$) for 91% ee.

Example 40—Preparation of (+)-(R,E)-(2-(Cyclohex-2-en-1-yl)prop-1-en-1-yl)benzene 42

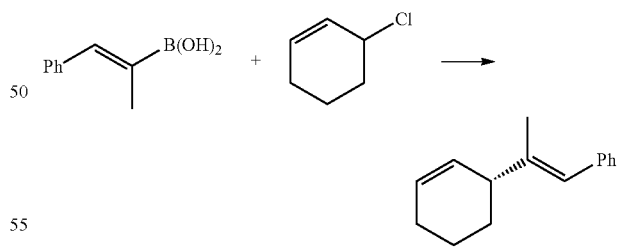

In a 10 mL round bottomed flask [Rh(cod)(OH)]$_2$ (3.4 mg, 0.007 mmol, 0.025 eq), (R)-BINAP A (11.2 mg, 0.018 mmol, 0.06 eq) and Cs$_2$CO$_3$ (97.7 mg, 0.30 mmol, 1.00 eq) were stirred in THF (1.5 mL) at 60° C. for 30 min. A solution of (Z)-(1-phenylprop-1-en-2-yl)boronic acid (97.2 mg, 0.60 mmol, 2.00 eq) and the allyl bromide (35 µL, 0.30 mmol, 1.00 eq) in THF (1.0 mL) was then added via syringe and the flask rinsed with THF (0.5 mL). The resulting mixture was then stirred for 4 h at 60° C. before the addition of SiO$_2$ (20 mg). The solvent was then carefully evaporated and the solid directly loaded onto a flash chromatography column and eluted with pentane to obtain (+)-(R,E)-(2-(cyclohex-2-en-1-yl)prop-1-en-1-yl)benzene in 75% yield (44.9 mg, 0.23 mmol).

Enantiomeric excess of 86% was determined by HPLC [Chiralpak® IB; flow: 1.0 mL/min; hexane; λ=210 nm; major enantiomer $t_R$=4.9 min; minor enantiomer $t_R$=5.4 min].

$^1$H NMR (400 MHz, CDCl$_3$) $\delta_H$/ppm 7.39-7.23 (m, 4H), 7.22-7.09 (m, 1H), 6.30 (s, 1H), 5.89-5.74 (m, 1H), 5.74-5.59 (m, 1H), 2.94-2.84 (m, 1H), 2.08-2.00 (m, 2H), 1.85 (s, 3H), 1.81-1.70 (m, 1H), 1.68-1.48 (m, 3H).

$^{13}$C NMR (101 MHz, CDCl$_3$) (142.5, 138.9, 130.1, 129.0, 128.6, 128.1, 128.0, 126.1, 126.0, 125.4, 45.6, 28.3, 25.3, 21.2, 16.7.

HRMS (EI) m/z calcd for $C_{15}H_{18}$ [M]$^+$: 198.1409, found: 198.1412.

IR ($v_{max}$/cm$^{-1}$): 1446, 1493, 1599, 2858, 2930.

$[\alpha]^{25}_{589}$=+98.1 (c 0.84 CHCl$_3$) for 86% ee.

Example 41—Preparation of (+)-(R)—N-tert-Butoxycarbonyl-5-phenyl-3-piperidene 43

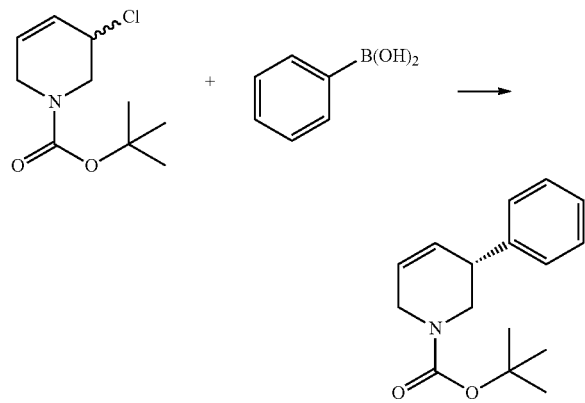

In a 10 mL round bottomed flask [Rh(cod)(OH)]$_2$ (4.6 mg, 0.01 mmol, 0.025 eq), (R)-5,5'-Dichloro-2,2'-bis(diphenylphosphino)-6,6-dimethoxy-1,1'-biphenyl (15.6 mg, 0.024 mmol, 0.06 eq) and Cs$_2$CO$_3$ (130.3 mg, 0.40 mmol, 1.00 eq) were stirred in THF (2 mL) at 60° C. for 30 min. A solution of N-tert-butoxycarbonyl-5-chloro-3-piperidene (86.8 mg, 0.40 mmol, 1.00 eq) in THF (0.75 mL) was then added via syringe and the flask rinsed with THF (0.25 mL) followed by a second solution of phenylboronic acid (97.5 mg, 0.80 mmol, 2.00 eq), which was also added via syringe and the flask rinsed with THF (0.25 mL). The resulting mixture was then stirred for 16 h at reflux before the addition of SiO$_2$ (20 mg). The solvent was then carefully evaporated and the solid directly loaded into a chromatographic column eluting with pentane/ether (9/1) to obtain the pure product in 76% yield (79.1 mg, 0.31 mmol) as a colorless oil.

Enantiomeric excess of 96% was determined by HPLC [Chiralpak® IA; flow: 1.0 mL/min; hexane/i-PrOH: 99.4: 0.6; λ=210 nm; major enantiomer $t_R$=6.9 min; minor enantiomer $t_R$=7.5 min].

TLC R$_f$=0.42 (hexane/ethyl acetate (9/1)).

$^1$H-NMR (400 MHz, Chloroform-d) δ 1.29 (s, 6H), 1.46 (s, 3H), 3.46 (d, J=38.9 Hz, 2H), 3.76 (s, 1H), 4.05 (t, J=16.2 Hz, 2H), 5.90 (s, 2H), 7.22 (tt, J=5.8, 1.8 Hz, 2H), 7.25 (d, J=1.5 Hz, 1H), 7.31 (dd, J=8.0, 6.5 Hz, 2H).

$^{13}$C-NMR (101 MHz, Chloroform-d) δ 28.29 (3C, 41.55 (1C), 42.94 (1C), 48.54 (1C), 77.25 (1C), 79.47 (1C), 125.91 (1C), 126.71 (1C), 127.89 (1C), 128.21 (1C), 128.48 (1C), 129.24 (1C), 142.21 (1C), 154.71 (1C).

IR (ATR) $v_{max}$/cm$^{-1}$=2975s, 1696l, 1452m, 1420m, 1366s, 1299m, 1237l, 1168s, 1113m HRMS (ESI): m/z calc. for $C_{16}H_{21}O_2N^{23}Na^+$ [M]$^+$: 282.14645, found: 282.14658.

$[\alpha]^{25}_{589}$=+112.9 (c 1.00, CHCl$_3$).

Example 42—Non-Linear Effects

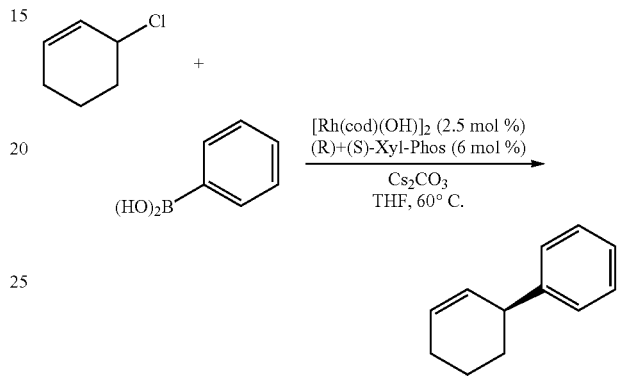

A set of reactions were performed where the enantiomeric ratio of chiral ligand A was varied.

Common Procedure: In a 10 mL round bottomed flask [Rh(cod)(OH)]$_2$ (4.6 mg, 0.01 mmol, 0.025 eq), a mixture of (R) and (S)-Xyl-P—PHOS (18.2 mg in total, 0.024 mmol, 0.06 eq) and Cs$_2$CO$_3$ (130.3 mg, 0.40 mmol, 1.00 eq) were stirred in THF (2 mL) at 60° C. for 30 min. A solution of phenylboronic acid (97.5 mg, 0.80 mmol, 2.00 eq) and 3-chlorocyclohexene (45 μL, 0.40 mmol, 1.00 eq) in THF (1.5 mL) was then added via syringe and the flask rinsed with THF (0.5 mL). The resulting mixture was then stirred for 1 h at 60° C. before the addition of SiO$_2$ (20 mg). The solvent was then carefully evaporated and the solid directly analysed by HPLC.

Enantiomeric excess was determined by HPLC [Chiralpak® ID; flow: 0.6 mL/min; hexane/i-PrOH: 99.9:0.1; λ=210 nm; major enantiomer $t_R$=8.3 min; minor enantiomer $t_R$=8.9 min].

The results showed a very good linear relationship between the ee of ligand A and product 2, suggesting that the active species in the catalytic cycle is a monomeric Rh(I)-ligand complex.

Example 43—Optimising Reagent Loading

Experiments were conducted to determine if the reaction could be scaled-up and if the catalyst loading could be lowered. Using the standard conditions on a 4.0 mmol scale, more than 600 mg of 2 can be prepared with no fine-tuning of the reaction conditions. Dropping the catalyst loading to 1.25 mol % of [Rh(cod)(OH)]$_2$ (which is a total of 2.5 mol % Rh) and 3 mol % of ligand A ((S)-Xyl-P—PHOS), gave 2 with comparable yield and enantioselectivity (Table 1, entry 1; 96%, 99.1% ee). When the catalyst loading was decreased to 0.5 mol % of [Rh(cod)(OH)]$_2$ and 1.2 mol % of ligand A there was no loss of enantioselectivity (99.7% ee) but lower yield (48%) was obtained after 4 h (Entry 2).

Reducing the catalyst loading to 0.25 mol % of [Rh(cod)(OH)]$_2$, completely inhibited the reaction (entry 3) even at extended (18 h) reaction times. Using the same catalyst loading (0.25 mol %) at 4 times the concentration (0.4 M) also gave no product (not shown).

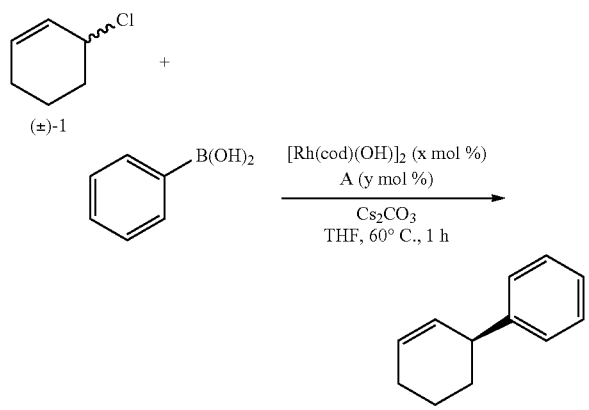

TABLE 1

Conditions: 4.0 mmol of 3-chlorocyclohex-1-ene, 8.0 mmol of benzeneboronic acid, [Rh(cod)(OH)]$_2$(x mol %), ligand A (y mol %), Cs$_2$CO$_3$ (1.00 eq) in THF at 60° C.

| Entry | x (mol %) | y (mol %) | time (h) | Yield (%) | ee (%) |
|---|---|---|---|---|---|
| 1 | 1.25 | 3.0 | 1 | 96 | 99.1 |
| 2 | 0.5 | 1.2 | 4 | 48 | 99.7 |
| 3 | 0.25 | 0.6 | 18 | — | — |

Example 44—Mechanistic Studies

To shed light on the regiochemical outcome of these DYKAT reactions, the AAA of 3-chloro-5-phenylcyclohex-1-ene 26 with phenylboronic acid was examined (see scheme below).

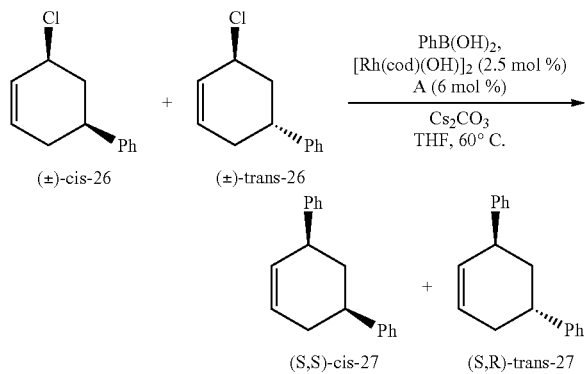

Different cis- and trans-ratios of racemic 26 were prepared and subjected to the reaction conditions. In order to reach completion it was necessary to stir these reactions for 18 h. These experiments show that DYKAT occurs with overall inversion of configuration. When using a cis:trans ratio of 1:25 starting material 26 was converted into 27 (100% conversion, 96% isolated yield) with a cis:trans ratio of 25:1 (Table 2, entry 1), where the relative stereochemistry of the starting material and product have been completely inverted and cis-27 and trans-27 were obtained with >98% ee. When a different starting cis:trans ratio of 26 is used (1:5.3), 27 was again obtained with complete relative inversion (Entry 2; a 5.3:1 ratio in favour of the cis-biaryl product) after 100% conversion and both products were obtained with very high (99.2% ee) enantiomeric excess. These observations suggest that both racemic isomers undergo overall enantioselective inversion processes to give the respective isomers of product 27. The absolute configuration of both cis- and trans-27 was tentatively assigned by analogy to the asymmetric reaction with unsubstituted allyl halides, so that ligand (S)-A ((S)-Xyl-P—PHOS) would favour the formation of the (S,S)-3,5-disubstituted cyclohexene derivative. The observed enantioselectivity in both cis- and trans-27 is practically identical and uniformly high is quite remarkable.

TABLE 2

Conditions: 1.0 eq of 3-chlorocyclohex-1-ene, 2.0 eq of benzeneboronic acid, [Rh(cod)(OH)]$_2$(2.5 mol %), ligand A (6 mol %), Cs$_2$CO$_3$ (1.00 eq) in THF at 60° C. stirring 18 h.

| Entry | 26 cis:trans$^a$ | Conversion (%) | 27 cis:trans$^a$ | cis-27 ee$^b$ (%) | trans-27 ee$^b$ (%) |
|---|---|---|---|---|---|
| 1 | 1:25 | 100 | 25:1 | 99.4 | 98 |
| 2 | 1:5.3 | 100 | 5.3:1 | 99.2 | 99.2 |

$^a$Determined by $^1$H NMR spectroscopy.
$^b$Determined by chiral HPLC.

While specific embodiments of the invention have been described herein for the purpose of reference and illustration, various modifications will be apparent to a person skilled in the art without departing from the scope of the invention as defined by the appended claims.

REFERENCES

1. Armin de Meijere, Stefan Brase, M. O. *Metal Catalyzed Cross-Coupling Reactions and More*. (Wiley-VCH, Weinheim, 2014).
2. Cooper, T. W. J., Campbell, I. B. & MacDonald, S. J. F. Factors determining the selection of organic reactions by medicinal chemists and the use of these reactions in arrays (Small Focused Libraries). *Angew. Chemie Int. Ed.* 49, 8082-8091 (2010).
3. Nadin, A., Hattotuwagama, C. & Churcher, I. Lead-oriented synthesis: A new opportunity for synthetic chemistry. *Angew. Chemie—Int. Ed.* 51, 1114-1122 (2012).
4. Roughley, S. D. & Jordan, A. M. The medicinal chemist's toolbox: An analysis of reactions used in the pursuit of drug candidates. *J. Med. Chem.* 54, 3451-3479 (2011).
5. Jacobsen, E. N., Pfaltz, A. & Yamamoto, H. *Comprehensive Asymmetric Catalysis: Suppl.* 2. (Springer, 2004).
6. Takaya, Y., Ogasawara, M. & Hayashi, T. Rhodium-Catalyzed Asymmetric 1, 4-Addition of Aryl- and Alkenylboronic Acids to Enones. *J. Am. Chem. Soc.* 3, 5579-5580 (1998).
7. Hayashi, T. & Yamasaki, K. Rhodium-catalyzed asymmetric 1,4-addition and its related asymmetric reactions. *Chem. Rev.* 103, 2829-2844 (2003).

8. Evans, P. A. Modern Rhodium-Catalyzed Organic Reactions. Modern Rhodium-Catalyzed Organic Reactions (Wiley-VCH, 2005). doi:10.1002/3527604693
9. Evans, P. a & Kennedy, L. J. Enantiospecific and regioselective rhodium-catalyzed allylic alkylation: diastereoselective approach to quaternary carbon stereogenic centers. *Org. Lett.* 2, 2213-2215 (2000).
10. Evans, P. A. & Leahy, D. K. Regioselective and enantiospecific rhodium-catalyzed allylic alkylation reactions using copper(I) enolates: Synthesis of (−)-sugiresinol dimethyl ether. *J. Am. Chem. Soc.* 125, 8974-8975 (2003).
11. Evans, P. A. & Uraguchi, D. Regio- and enantiospecific rhodium-catalyzed arylation of unsymmetrical fluorinated acyclic allylic carbonates: inversion of absolute configuration. *J. Am. Chem. Soc.* 125, 7158-7159 (2003).
12. Huerta, F. F., Minidis, A. B. E. & Baickvall, J. Racemisation in asymmetric synthesis. Dynamic kinetic resolution and related processes in enzyme and metal catalysis. *Chem. Soc. Rev.* 30, 321-331 (2001).
13. Vedejs, E. & Jure, M. Efficiency in nonenzymatic kinetic resolution. *Angew. Chem. Int. Ed. Engl.* 44, 3974-4001 (2005).
14. Trost, Barry M., Fandrick, D. R. Palladium-catalyzed dynamic kinetic asymmetric allylic alkylation with the DPPBA ligands. *Aldrichimica Acta* 40, 59-72 (2007).
15. Trost, B. M. & Thaisrivongs, D. a. Strategy for employing unstabilized nucleophiles in palladium-catalyzed asymmetric allylic alkylations. *J. Am. Chem. Soc.* 130, 14092-14093 (2008).
16. Misale, A., Niyomchon, S., Luparia, M. & Maulide, N. Asymmetric palladium-catalyzed allylic alkylation using dialkylzinc reagents: a remarkable ligand effect. *Angew. Chem. Int. Ed. Engl.* 53, 7068-7073 (2014).
17. Langlois, J.-B., Emery, D., Mareda, J. & Alexakis, A. Mechanistic identification and improvement of a direct enantioconvergent transformation in copper-catalyzed asymmetric allylic alkylation. *Chem. Sci.* 3, 1062-1069 (2012).
18. Ito, H., Kunii, S. & Sawamura, M. Direct enantioconvergent transformation of racemic substrates without racemization or symmetrization. *Nat. Chem.* 2, 972-976 (2010).
19. Boronic Acids: Preparation and Applications in Organic Synthesis, Medicine and Materials, Second Edition. Edited by Dennis G. Hall. 2011 Wiley-VCH Verlag GmbH & Co. KGaA. Published 2011 by Wiley-VCH Verlag GmbH & Co. KGaA.

The invention claimed is:
1. A process for the formation of a $C_{sp3}$—$C_{sp2}$ bond at the allylic carbon of a cyclic allylic compound, the process comprising the step of:
a) reacting a racemic mixture of a cyclic allylic compound having a leaving group attached to the allylic carbon with a compound having a nucleophilic carbon atom, wherein step a) is conducted in the presence of:
i) a pre-catalyst based on Rh(I); and
ii) a chiral ligand
and wherein the formation of the $C_{sp3}$—$C_{sp2}$ bond results in the generation of a product compound in a stereoisomeric excess.
2. The process of claim 1, wherein in step a), the cyclic allylic compound having a leaving group attached to the allylic carbon also has a hydrogen attached to the allylic carbon.

3. The process of claim 1, wherein the chiral ligand is non-racemic.
4. The process of claim 1, wherein the chiral ligand is a phosphorus containing ligand or a diene ligand.
5. The process of claim 1, wherein the chiral ligand is a monodentate ligand, a bidentate ligand, or a tridentate ligand.
6. The process of claim 1, wherein the chiral ligand is selected from monophosphines, monophosphites, monophosphinites, monophosphonites, bisphosphines, bisphosphites, bisphosphinites, bisphosphonites, phosphoramidites and dienes.
7. The process of claim 1, wherein the pre-catalyst based on Rh(I) is selected from [Rh(COD)(OH)]$_2$, wherein COD denotes cyclooctadiene, or Rh(acac)(C$_2$H$_4$)$_2$, wherein acac denotes acetylacetone.
8. The process of claim 1, wherein the product compound produced in a stereoisomeric excess has a structure according to formula (I) shown below:

(I)

wherein
ring A is a 4-8 membered carbocyclyl or heterocyclyl ring optionally fused to one or more rings B, wherein rings A and B are each independently optionally substituted with one or more groups selected from oxo, (1-8C) alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, NR$_a$R$_b$, OR$_a$, C(O)R$_a$, C(O)OR$_a$, OC(O)R$_a$, C(O)N(R$_b$)R$_a$, N(R$_b$)C(O)R$_a$, S(O)$_x$R$_a$, SO$_2$N(R$_b$)R$_a$, N(R$_b$)SO$_2$R$_a$, (CH$_2$)$_y$NR$_a$R$_b$, (O)$_z$Si(R$_a$)$_3$, (O)$_z$Si(OR$_a$)$_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C)alkoxy;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-8C)alkyl, (2-8C)alkenyl, (2-8C)alkynyl, halo, trifluoromethyl, trifluoromethoxy, cyano, nitro, hydroxyl, amino, (1-8C) haloalkyl, (1-8C)alkoxy, (1-8C)haloalkoxy, carboxyl, carbamoyl, sulphamoyl, NR$_a$R$_b$, OR$_a$, C(O) R$_a$, C(O)OR$_a$, OC(O)R$_a$, C(O)N(R$_b$)R$_a$, N(R$_b$)C(O) R$_a$, S(O)$_x$R$_a$, SO$_2$N(R$_b$)R$_a$, N(R$_b$)SO$_2$R$_a$, (CH$_2$)$_y$ NR$_a$R$_b$, (O)$_z$Si(R$_a$)$_3$,(O)$_z$Si(OR$_a$)$_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C) alkoxy; and R$_1$ is selected from aryl or heteroaryl, either of which may be optionally fused to one or more rings C, and optionally substituted with one or more substituents selected from oxo, (1-8C)alkyl, (2-8C)alkenyl, (2-8C) alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, NR$_a$R$_b$, OR$_a$, C(O)R$_a$, C(O)OR$_a$, OC(O)R$_a$, C(O)N(R$_b$)R$_a$, N(R$_b$)C(O)R$_a$, S(O)$_x$R$_a$, SO$_2$N(R$_b$)R$_a$, N(R$_b$)SO$_2$R$_a$, (CH$_2$)$_y$NR$_a$R$_b$, (O)$_z$Si(R$_a$)$_3$, (O)$_z$Si(OR$_a$)$_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C) alkyl, and 5-6 membered heteroaryl(1-3C)alkoxy;
wherein
each ring C is monocyclic or bicyclic aryl or heteroaryl, any of which is optionally substituted with one or more groups selected from oxo, (1-8C)alkyl, (2-8) alkenyl, (2-8C)alkynyl, halo, trifluoromethyl, trifluoromethoxy, cyano, nitro, hydroxyl, amino, (1-8C) haloalkyl, (1-8C)alkoxy, (1-8C)haloalkoxy, carboxyl, carbamoyl, sulphamoyl, NR$_a$R$_b$, OR$_a$, C(O)R$_a$, C(O)OR$_a$, OC(O)R$_a$, C(O)N(R$_b$)R$_a$, N(R$_b$) C(O)R$_a$, S(O)$_x$R$_a$, SO$_2$N(R$_b$)R$_a$, N(R$_b$)SO$_2$R$_a$, (CH$_2$)$_y$NR$_a$R$_b$, (O)$_z$Si(R$_a$)$_3$, (O)$_z$Si(OR$_a$)$_3$, 4-6 membered carbocyclyl, 4-6 membered carbocyclyl(1-3C) alkyl, 4-6 membered carbocyclyl(1-3C)alkoxy, 4-6 membered heterocyclyl, 4-6 membered heterocyclyl (1-3C)alkyl, 4-6 membered heterocyclyl(1-3C) alkoxy, phenyl, phenyl(1-3C)alkyl, phenyl(1-3C) alkoxy, 5-6 membered heteroaryl, 5-6 membered heteroaryl(1-3C)alkyl, and 5-6 membered heteroaryl (1-3C)alkoxy;
or R$_1$ is a group

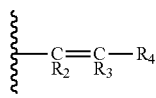

wherein
R$_2$, R$_3$ and R$_4$ are independently selected from
i) H, (1-8C)alkyl, (2-8C)alkenyl, (2-8C)alkynyl, halo, trifluoromethyl, trifluoromethoxy, cyano, nitro, (1-8C) haloalkyl, (1-8C)alkoxy, (1-8C)haloalkoxy, carboxyl, carbamoyl, sulphamoyl, NR$_a$R$_b$, OR$_a$, C(O)R$_a$, C(O)OR$_a$, OC(O)R$_a$, C(O)N(R$_b$)R$_a$, N(R$_b$)C(O)R$_a$, S(O)$_x$R$_a$, SO$_2$N(R$_b$)R$_a$, N(R$_b$)SO$_2$R$_a$, (CH$_2$)$_y$NR$_a$R$_b$, (O)$_z$Si(R$_a$)$_3$ and (O)$_z$Si(OR$_a$)$_3$; or
ii) 4-6 membered carbocyclyl, 4-6 membered carbocyclyl (1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C) alkoxy, phenyl, phenyl(1-3C)alkyl, phenyl(1-3C) alkoxy, 5-6 membered heteroaryl, 5-6 membered heteroaryl(1-3C)alkyl, and 5-6 membered heteroaryl(1-3C)alkoxy, the cyclic moieties of which may be optionally substituted with one or more substituents selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, NR$_a$R$_b$, OR$_a$, C(O)R$_a$, C(O)OR$_a$, OC(O)R$_a$, C(O)N(R$_b$)R$_a$, N(R$_b$)C(O)R$_a$, S(O)$_x$R$_a$, SO$_2$N(R$_b$)R$_a$, N(R$_b$) SO$_2$R$_a$, (CH$_2$)$_y$NR$_a$R$_b$, (O)$_z$Si(R$_a$)$_3$, (O)$_z$Si(OR$_a$)$_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C) alkyl, and 5-6 membered heteroaryl(1-3C)alkoxy;
wherein
each of R$_a$ and R$_b$ are independently selected from H, (1-6C)alkyl, (2-6C)alkenyl and (2-6C)alkynyl;
each x is independently 0, 1 or 2;
each y is independently 1, 2, or 3; and
each z is independently 0 or 1.

9. The process of claim 1, wherein, in step a), the cyclic allylic compound having a leaving group attached to the allylic carbon has a structure according to formula (II) shown below:

wherein
ring A is a 4-8 membered carbocyclyl or heterocyclyl ring optionally fused to one or more rings B, wherein rings A and B are each independently optionally substituted with one or more groups selected from oxo, (1-8C) alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, NR$_a$R$_b$, OR$_a$, C(O)R$_a$, C(O)OR$_a$, OC(O)R$_a$, C(O)N(R$_b$)R$_a$, N(R$_b$)C(O)R$_a$, S(O)$_x$R$_a$, SO$_2$N(R$_b$)R$_a$, N(R$_b$)SO$_2$R$_a$, (CH$_2$)$_y$NR$_a$R$_b$, (O)$_z$Si(R$_a$)$_3$, (O)$_z$Si(OR$_a$)$_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C)alkoxy;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-8C)alkyl, (2-8C)alkenyl, (2-8C)alkynyl, halo, trifluoromethyl, trifluoromethoxy, cyano, nitro, hydroxyl, amino, (1-8C) haloalkyl, (1-8C)alkoxy, (1-8C)haloalkoxy, carboxyl, carbamoyl, sulphamoyl, NR$_a$R$_b$, OR$_a$, C(O) R$_a$, C(O)OR$_a$, OC(O)R$_a$, C(O)N(R$_b$)R$_a$, N(R$_b$)C(O) R$_a$, S(O)$_x$R$_a$, SO$_2$N(R$_b$)R$_a$, N(R$_b$)SO$_2$R$_a$, (CH$_2$)$_y$ NR$_a$R$_b$, (O)$_z$Si(R$_a$)$_3$, (O)$_z$Si(OR$_a$)$_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-

3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C)alkoxy; and X is the leaving group.

10. The process of claim 1, wherein, in step a), the compound having a nucleophilic carbon atom has a structure according to formula (III) shown below:

$$Z-R_1 \quad (III)$$

wherein $R_1$ is selected from aryl or heteroaryl, either of which may be optionally fused to one or more rings C, and optionally substituted with one or more substituents selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$, $SO_2N(R_b)R_a$, $N(R_b)SO_2R_a$, $(CH_2)_yNR_aR_b$, $(O)_zSi(R_a)_3$, $(O)_zSi(OR_a)_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C)alkoxy;

wherein each ring C is monocyclic or bicyclic aryl or heteroaryl, any of which is optionally substituted with one or more groups selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$, $SO_2N(R_b)R_a$, $N(R_b)SO_2R_a$, $(CH_2)_yNR_aR_b$, $(O)_zSi(R_a)_3$, $(O)_zSi(OR_a)_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl (1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl (1-3C)alkoxy;

or $R_1$ is a group

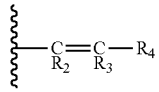

wherein $R_2$, $R_3$ and $R_4$ are independently selected from i) H, (1-8C)alkyl, (2-8C)alkenyl, (2-8C)alkynyl, halo, trifluoromethyl, trifluoromethoxy, cyano, nitro, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$, $SO_2N(R_b)R_a$, $N(R_b)SO_2R_a$, $(CH_2)_yNR_aR_b$, $(O)_zSi(R_a)_3$ and $(O)_zSi(OR_a)_3$; or ii) 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C)alkoxy, the cyclic moieties of which may be optionally substituted with one or more substituents selected from oxo, (1-8C)alkyl, (2-8C)alkenyl, (2-8C)alkynyl, halo, trifluoromethyl, trifluoromethoxy, cyano, nitro, hydroxyl, amino, (1-8C)haloalkyl, (1-8C)alkoxy, (1-8C)haloalkoxy, carboxyl, carbamoyl, sulphamoyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_xR_a$, $SO_2N(R_b)R_a$, $N(R_b)SO_2R_a$, $(CH_2)_yNR_aR_b$, $(O)_zSi(R_a)_3$, $(O)_zSi(OR_a)_3$, 4-6 membered carbocyclyl, 4-6 membered carbocyclyl(1-3C)alkyl, 4-6 membered carbocyclyl(1-3C)alkoxy, 4-6 membered heterocyclyl, 4-6 membered heterocyclyl(1-3C)alkyl, 4-6 membered heterocyclyl(1-3C)alkoxy, phenyl, phenyl(1-3C)alkyl, phenyl(1-3C)alkoxy, 5-6 membered heteroaryl, 5-6 membered heteroaryl(1-3C)alkyl, and 5-6 membered heteroaryl(1-3C)alkoxy;

wherein each of $R_a$ and $R_b$ are independently selected from H, (1-6C)alkyl, (2-6C)alkenyl and (2-6C)alkynyl;

each x is independently 0, 1 or 2;

each y is independently 1, 2, or 3; and each z is independently 0 or 1; and

Z is selected from one of the following options:

(i) Z is H;

(ii) when taken with $R_1$, Z forms a boronic acid, or a boronic acid derivative;

(iii) Z is a metal selected from Si, Zn, Bi, Mg, Ti or Sn, said metal being optionally associated with one or more groups selected from halo, hydroxyl, (1-4C)alkyl, (1-4C)alkoxy, and aryl, such that the compound of formula III is an organometallic nucleophile; or (iv) Z is a group $B(Y_3)_3^-M^+$, wherein $Y_3$ is selected from halo and (1-4C)alkoxy; and M is a cation selected from $Na^+$, $K^+$ and $Li^+$.

11. The process of claim 1, wherein the leaving group is selected from halo, phosphate, sulfonate, sulfinate, sulphonamide, carboxylate, carbonate, thiolate and nitrate.

12. The process of claim 1, wherein the leaving group is selected from I, Br and Cl.

13. The process of claim 8, wherein ring A is a 4-8 membered carbocyclyl or heterocyclyl ring optionally fused to one or more rings B, wherein rings A and B are each independently optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$, $(O)_zSi(R_a)_3$, $(O)_zSi(OR_a)_3$, 4-6 membered carbocyclyl, 4-6 membered heterocyclyl, phenyl and 5-6 membered heteroaryl;

wherein each ring B is independently 5-8 membered carbocyclyl, 6-8 membered aryl, 5-8 membered heterocyclyl or 5-8 membered heteroaryl, any of which may be optionally substituted with one or more groups selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$, $(O)_zSi(R_a)_3$, $(O)_zSi(OR_a)_3$, 4-6 membered carbocyclyl, 4-6 membered heterocyclyl, phenyl and 5-6 membered heteroaryl.

14. The process of claim 8, wherein
ring A is a 5-7 membered carbocyclyl or heterocyclyl ring optionally fused to one or more rings B, wherein rings A and B are each independently optionally substituted with one or more groups selected from oxo, (1-6C) alkyl, (2-6C)alkenyl, (2-6C)alkynyl, halo, trifluoromethyl, cyano, nitro, hydroxyl, amino, (1-6C)alkoxy, carboxyl, $NR_aR_b$, $OR_a$, $C(O)R_a$, $C(O)OR_a$, $OC(O)R_a$, $(CH_2)_yNR_aR_b$, $(O)_zSi(R_a)_3$, $(O)_zSi(OR_a)_3$, 4-6 membered carbocyclyl, 4-6 membered heterocyclyl, phenyl and 5-6 membered heteroaryl;
wherein
each ring B is independently 5-8 membered carbocyclyl, 6-8 membered aryl, 5-8 membered heterocyclyl or 5-8 membered heteroaryl, any of which may be optionally substituted with one or more groups selected from oxo, (1-6C)alkyl, (2-6C)alkenyl, (2-6C)alkynyl, halo, trifluoromethyl, cyano, nitro, hydroxyl, amino, (1-6C)alkoxy, carboxyl, $NR_aR_b$, $OR_a$, $C(O)R_a$, $C(O)OR_a$, $OC(O)R_a$, $(CH_2)_yNR_aR_b$, $(O)_zSi(R_a)_3$, $(O)_zSi(OR_a)_3$, 4-6 membered carbocyclyl, 4-6 membered heterocyclyl, phenyl and 5-6 membered heteroaryl.

15. The process of claim 8, wherein
$R_1$ is selected from aryl or heteroaryl, either of which may be optionally fused to one or more rings C, and optionally substituted with one or more substituents selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_yNR_aR_b$, $(O)_zSi(R_a)_3$, $(O)_zSi(OR_a)_3$, 4-6 membered carbocyclyl, 4-6 membered heterocyclyl, phenyl, phenyl(1-3C)alkyl, phenyl (1-3C)alkoxy and 5-6 membered heteroaryl;
wherein
each ring C is monocyclic or bicyclic aryl or heteroaryl, any of which is optionally substituted with one or more groups selected from oxo, (1-8C)alkyl, (2-8C) alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_y$ $NR_aR_b$, $(O)_zSi(R_a)_3$, $(O)_zSi(OR_a)_3$, 4-6 membered carbocyclyl, 4-6 membered heterocyclyl, phenyl and 5-6 membered heteroaryl;
or $R_1$ is a group

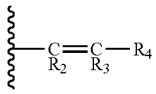

wherein
$R_2$, $R_3$ and $R_4$ are independently selected from
i) H, (1-8C)alkyl, (2-8C)alkenyl, (2-8C)alkynyl, halo, trifluoromethyl, cyano, nitro, (1-8C)alkoxy, carboxyl, $NR_aR_b$, $OR_a$, $C(O)R_a$, $C(O)OR_a$, $OC(O)R_a$, $(CH_2)_y$ $NR_aR_b$, $(O)_zSi(R_a)_3$ and $(O)_zSi(OR_a)_3$; or
ii) 4-6 membered carbocyclyl, 4-6 membered heterocyclyl, phenyl, phenyl(1-3C)alkyl and 5-6 membered heteroaryl, the cyclic moieties of which may be optionally substituted with one or more substituents selected from oxo, (1-8C)alkyl, (2-8C)alkenyl, (2-8C)alkynyl, halo, trifluoromethyl, cyano, nitro, hydroxyl, amino, (1-8C)alkoxy, carboxyl, $NR_aR_b$, $OR_a$, $C(O)R_a$, $C(O)$ $OR_a$, $OC(O)R_a$, $(CH_2)_yNR_aR_b$, $(O)_zSi(R_a)_3$, $(O)_zSi$ $(OR_a)_3$, 4-6 membered carbocyclyl, 4-6 membered heterocyclyl, phenyl and 5-6 membered heteroaryl.

16. The process of claim 8, wherein
$R_1$ is selected from phenyl or 5-6 membered heteroaryl, either of which may be optionally fused to one or more rings C, and optionally substituted with one or more substituents selected from oxo, (1-6C)alkyl, (2-6C) alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_y$ $NR_aR_b$, $(O)_zSi(R_a)_3$, $(O)_zSi(OR_a)_3$, 4-6 membered carbocyclyl, 4-6 membered heterocyclyl, phenyl, phenyl (1-3C)alkyl, phenyl(1-3C)alkoxy and 5-6 membered heteroaryl;
wherein
each ring C is monocyclic or bicyclic aryl or heteroaryl, any of which is optionally substituted with one or more groups selected from oxo, (1-6C)alkyl, (2-6C) alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)OR_a$, $OC(O)R_a$, $(CH_2)_y$ $NR_aR_b$, $(O)_zSi(R_a)_3$, $(O)_zSi(OR_a)_3$, 4-6 membered carbocyclyl, 4-6 membered heterocyclyl, phenyl and 5-6 membered heteroaryl;
or $R_1$ is a group

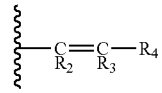

wherein
$R_2$, $R_3$ and $R_4$ are independently selected from
i) H, (1-6C)alkyl, (2-6C)alkenyl, (2-6C)alkynyl, halo, trifluoromethyl, cyano, nitro, (1-8C)alkoxy, carboxyl, $NR_aR_b$, $OR_a$, $C(O)R_a$, $C(O)OR_a$, $OC(O)R_a$, $(CH_2)_y$ $NR_aR_b$, $(O)_zSi(R_a)_3$ and $(O)_zSi(OR_a)3$; or
ii) 4-6 membered carbocyclyl, 4-6 membered heterocyclyl, phenyl, phenyl(1-3C)alkyl and 5-6 membered heteroaryl, the cyclic moieties of which may be optionally substituted with one or more substituents selected from oxo, (1-6C)alkyl, (2-6C)alkenyl, (2-6C)alkynyl, halo, trifluoromethyl, cyano, nitro, hydroxyl, amino, (1-8C)alkoxy, carboxyl, $NR_aR_b$, $OR_a$, $C(O)R_a$, $C(O)$ $OR_a$, $OC(O)R_a$, $(CH_2)_yNR_aR_b$, $(O)_zSi(R_a)_3$, $(O)_zSi$ $(OR_a)_3$, 4-6 membered carbocyclyl, 4-6 membered heterocyclyl, phenyl and 5-6 membered heteroaryl.

17. The process of claim 10, wherein when taken with $R_1$, Z forms a boronic acid, or a boronic acid derivative.

18. The process of claim 1, wherein step a) is also conducted in the presence of a base.

19. The process of claim 18, wherein the base is selected from $Cs_2CO_3$, CsOH, $K_2CO_3$, $NaHCO_3$, NaOtBu, MTBD, KOH, NaOH, LiOH, $Ba(OH)_2$, $Et_3N$ and $K_3PO_4$.

20. The process of claim 18, wherein the base is $Cs_2CO_3$.

* * * * *

UNITED STATES PATENT AND TRADEMARK OFFICE
CERTIFICATE OF CORRECTION

PATENT NO. : 10,464,861 B2
APPLICATION NO. : 15/580838
DATED : November 5, 2019
INVENTOR(S) : Stephen Patrick Fletcher et al.

Page 1 of 1

It is certified that error appears in the above-identified patent and that said Letters Patent is hereby corrected as shown below:

In the Claims

At Column 71, Lines 24-25:
"(2-8)alkenyl"

Should read:
-- (2-8C)alkenyl --.

Signed and Sealed this
Twenty-first Day of January, 2020

Andrei Iancu
*Director of the United States Patent and Trademark Office*